US012661039B2

(12) United States Patent
Vo et al.

(10) Patent No.: US 12,661,039 B2
(45) Date of Patent: **\*Jun. 23, 2026**

(54) NONINVASIVE PHYSIOLOGICAL SENSOR

(71) Applicant: Willow Laboratories, Inc., Irvine, CA (US)

(72) Inventors: Hung The Vo, Fountain Valley, CA (US); Kevin Hughes Pauley, Lake Forest, CA (US); Cristiano Dalvi, Lake Forest, CA (US); Sean Merritt, Lake Forest, CA (US); Jesse Chen, Foothill Ranch, CA (US); Jeroen Poeze, Rancho Santa Margarita, CA (US); Ferdyan Lesmana, Irvine, CA (US); Ruiqi Long, Irvine, CA (US)

(73) Assignee: Willow Laboratories, Inc., Irvine, CA (US)

(\*) Notice: Subject to any disclaimer, the term of this patent is extended or adjusted under 35 U.S.C. 154(b) by 0 days.

This patent is subject to a terminal disclaimer.

(21) Appl. No.: 18/746,671

(22) Filed: Jun. 18, 2024

(65) Prior Publication Data

US 2024/0407677 A1 Dec. 12, 2024

Related U.S. Application Data

(63) Continuation of application No. 18/158,388, filed on Jan. 23, 2023, now Pat. No. 12,064,240, which is a (Continued)

(51) Int. Cl.
*A61B 5/1455* (2006.01)
*A61B 5/00* (2006.01)

(52) U.S. Cl.
CPC .......... *A61B 5/1455* (2013.01); *A61B 5/6826* (2013.01); *A61B 5/6838* (2013.01); *A61B 2562/0242* (2013.01)

(58) Field of Classification Search
CPC ... A61B 5/1455; A61B 5/6826; A61B 5/6838; A61B 2562/0242; A61B 2562/223; A61B 2562/0233; A61B 5/0261
(Continued)

(56) References Cited

U.S. PATENT DOCUMENTS 4,960,128 A 10/1990 Gordon et al.
4,964,408 A 10/1990 Hink et al.
(Continued)

OTHER PUBLICATIONS

US 2022/0192529 A1, 06/2022, Al-Ali et al. (withdrawn)
US 2024/0016391 A1, 01/2024, Lapotko et al. (withdrawn)

*Primary Examiner* — Md M Rahman
(74) *Attorney, Agent, or Firm* — Knobbe, Martens, Olson & Bear, LLP

(57) ABSTRACT

A noninvasive physiological sensor can include a first body portion and a second body portion coupled to each other and configured to at least partially enclose a user's finger. The sensor can further include a first probe coupled to one or more emitters and a second probe coupled to a detector. The first probe can direct light emitted from the one or more emitters toward tissue of the user's finger and the second probe can direct light attenuated through the tissue to the detector. The first and second probes can be coupled to the first and second body portions such that when the first and second body portions are rotated with respect to one another, ends of the first and second probes can be moved in a direction towards one another to compress the tissue of the user's finger.

15 Claims, 34 Drawing Sheets

Related U.S. Application Data continuation of application No. 16/721,527, filed on Dec. 19, 2019, now Pat. No. 11,684,296.

(60) Provisional application No. 62/839,454, filed on Apr. 26, 2019, provisional application No. 62/784,068, filed on Dec. 21, 2018.

(58) Field of Classification Search
USPC ........................................................ 356/300
See application file for complete search history.

(56) References Cited

U.S. PATENT DOCUMENTS

| | | | |
|---|---|---|---|
| 5,319,355 | A | 6/1994 | Russek |
| 5,337,744 | A | 8/1994 | Branigan |
| 5,341,805 | A | 8/1994 | Stavridi et al. |
| 5,377,676 | A | 1/1995 | Vari et al. |
| 5,431,170 | A | 7/1995 | Mathews |
| 5,436,499 | A | 7/1995 | Namavar et al. |
| 5,456,252 | A | 10/1995 | Vari et al. |
| 5,479,934 | A | 1/1996 | Imran |
| 5,482,036 | A | 1/1996 | Diab et al. |
| 5,494,043 | A | 2/1996 | O'Sullivan et al. |
| 5,533,511 | A | 7/1996 | Kaspari et al. |
| 5,590,649 | A | 1/1997 | Caro et al. |
| 5,602,924 | A | 2/1997 | Durand et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,671,914 | A | 9/1997 | Kalkhoran et al. |
| 5,726,440 | A | 3/1998 | Kalkhoran et al. |
| D393,830 | S | 4/1998 | Tobler et al. |
| 5,743,262 | A | 4/1998 | Lepper, Jr. et al. |
| 5,747,806 | A | 5/1998 | Khalil et al. |
| 5,750,994 | A | 5/1998 | Schlager |
| 5,758,644 | A | 6/1998 | Diab et al. |
| 5,760,910 | A | 6/1998 | Lepper, Jr. et al. |
| 5,890,929 | A | 4/1999 | Mills et al. |
| 5,919,134 | A | 7/1999 | Diab |
| 5,987,343 | A | 11/1999 | Kinast |
| 5,997,343 | A | 12/1999 | Mills et al. |
| 6,002,952 | A | 12/1999 | Diab et al. |
| 6,010,937 | A | 1/2000 | Karam et al. |
| 6,027,452 | A | 2/2000 | Flaherty et al. |
| 6,040,578 | A | 3/2000 | Malin et al. |
| 6,066,204 | A | 5/2000 | Haven |
| 6,115,673 | A | 9/2000 | Malin et al. |
| 6,124,597 | A | 9/2000 | Shehada et al. |
| 6,128,521 | A | 10/2000 | Marro et al. |
| 6,129,675 | A | 10/2000 | Jay |
| 6,144,868 | A | 11/2000 | Parker |
| 6,152,754 | A | 11/2000 | Gerhardt et al. |
| 6,184,521 | B1 | 2/2001 | Coffin, IV et al. |
| 6,232,609 | B1 | 5/2001 | Snyder et al. |
| 6,241,683 | B1 | 6/2001 | Macklem et al. |
| 6,253,097 | B1 | 6/2001 | Aronow et al. |
| 6,255,708 | B1 | 7/2001 | Sudharsanan et al. |
| 6,280,381 | B1 | 8/2001 | Malin et al. |
| 6,285,896 | B1 | 9/2001 | Tobler et al. |
| 6,308,089 | B1 | 10/2001 | von der Ruhr et al. |
| 6,317,627 | B1 | 11/2001 | Ennen et al. |
| 6,321,100 | B1 | 11/2001 | Parker |
| 6,334,065 | B1 | 12/2001 | Al-Ali et al. |
| 6,360,114 | B1 | 3/2002 | Diab et al. |
| 6,368,283 | B1 | 4/2002 | Xu et al. |
| 6,411,373 | B1 | 6/2002 | Garside et al. |
| 6,415,167 | B1 | 7/2002 | Blank et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,487,429 | B2 | 11/2002 | Hockersmith et al. |
| 6,505,059 | B1 | 1/2003 | Kollias et al. |
| 6,525,386 | B1 | 2/2003 | Mills et al. |
| 6,526,300 | B1 | 2/2003 | Kiani et al. |
| 6,534,012 | B1 | 3/2003 | Hazen et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,587,196 | B1 | 7/2003 | Stippick et al. |
| 6,587,199 | B1 | 7/2003 | Luu |
| 6,597,932 | B2 | 7/2003 | Tian et al. |
| 6,606,511 | B1 | 8/2003 | Ali et al. |
| 6,635,559 | B2 | 10/2003 | Greenwald et al. |
| 6,639,668 | B1 | 10/2003 | Trepagnier |
| 6,640,116 | B2 | 10/2003 | Diab |
| 6,640,117 | B2 | 10/2003 | Makarewicz et al. |
| 6,658,276 | B2 | 12/2003 | Kiani et al. |
| 6,661,161 | B1 | 12/2003 | Lanzo et al. |
| 6,697,656 | B1 | 2/2004 | Al-Ali |
| 6,697,658 | B2 | 2/2004 | Al-Ali |
| RE38,476 | E | 3/2004 | Diab et al. |
| RE38,492 | E | 4/2004 | Diab et al. |
| 6,738,652 | B2 | 5/2004 | Mattu et al. |
| 6,760,607 | B2 | 7/2004 | Al-Ali |
| 6,788,965 | B2 | 9/2004 | Ruchti et al. |
| 6,816,241 | B2 | 11/2004 | Grubisic |
| 6,822,564 | B2 | 11/2004 | Ai-Ali |
| 6,850,787 | B2 | 2/2005 | Weber et al. |
| 6,850,788 | B2 | 2/2005 | Al-Ali |
| 6,876,931 | B2 | 4/2005 | Lorenz et al. |
| 6,920,345 | B2 | 7/2005 | Al-Ali et al. |
| 6,934,570 | B2 | 8/2005 | Kiani et al. |
| 6,943,348 | B1 | 9/2005 | Coffin IV |
| 6,956,649 | B2 | 10/2005 | Acosta et al. |
| 6,961,598 | B2 | 11/2005 | Diab |
| 6,970,792 | B1 | 11/2005 | Diab |
| 6,985,764 | B2 | 1/2006 | Mason et al. |
| 6,990,364 | B2 | 1/2006 | Ruchti et al. |
| 6,998,247 | B2 | 2/2006 | Monfre et al. |
| 7,003,338 | B2 | 2/2006 | Weber et al. |
| 7,015,451 | B2 | 3/2006 | Dalke et al. |
| 7,027,849 | B2 | 4/2006 | Al-Ali |
| D526,719 | S | 8/2006 | Richie, Jr. et al. |
| 7,096,052 | B2 | 8/2006 | Mason et al. |
| 7,096,054 | B2 | 8/2006 | Abdul-Hafiz et al. |
| D529,616 | S | 10/2006 | Deros et al. |
| 7,133,710 | B2 | 11/2006 | Acosta et al. |
| 7,142,901 | B2 | 11/2006 | Kiani et al. |
| 7,225,006 | B2 | 5/2007 | Al-Ali et al. |
| RE39,672 | E | 6/2007 | Shehada et al. |
| 7,254,429 | B2 | 8/2007 | Schurman et al. |
| 7,254,431 | B2 | 8/2007 | Al-Ali et al. |
| 7,254,434 | B2 | 8/2007 | Schulz et al. |
| 7,274,955 | B2 | 9/2007 | Kiani et al. |
| D554,263 | S | 10/2007 | Al-Ali et al. |
| 7,280,858 | B2 | 10/2007 | Al-Ali et al. |
| 7,289,835 | B2 | 10/2007 | Mansfield et al. |
| 7,292,883 | B2 | 11/2007 | De Felice et al. |
| 7,341,559 | B2 | 3/2008 | Schulz et al. |
| 7,343,186 | B2 | 3/2008 | Lamego et al. |
| D566,282 | S | 4/2008 | Al-Ali et al. |
| 7,356,365 | B2 | 4/2008 | Schurman |
| 7,371,981 | B2 | 5/2008 | Abdul-Hafiz |
| 7,373,193 | B2 | 5/2008 | Al-Ali et al. |
| 7,377,794 | B2 | 5/2008 | Al-Ali et al. |
| 7,395,158 | B2 | 7/2008 | Monfre et al. |
| 7,415,297 | B2 | 8/2008 | Al-Ali et al. |
| 7,438,683 | B2 | 10/2008 | Al-Ali et al. |
| 7,483,729 | B2 | 1/2009 | Al-Ali et al. |
| D587,657 | S | 3/2009 | Al-Ali et al. |
| 7,500,950 | B2 | 3/2009 | Al-Ali et al. |
| 7,509,494 | B2 | 3/2009 | Al-Ali |
| 7,510,849 | B2 | 3/2009 | Schurman et al. |
| 7,514,725 | B2 | 4/2009 | Wojtczuk et al. |
| 7,519,406 | B2 | 4/2009 | Blank et al. |
| D592,507 | S | 5/2009 | Wachman et al. |
| 7,530,942 | B1 | 5/2009 | Diab |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,620,674 | B2 | 11/2009 | Ruchti et al. |
| D606,659 | S | 12/2009 | Kiani et al. |
| 7,629,039 | B2 | 12/2009 | Eckerbom et al. |

(56) References Cited

U.S. PATENT DOCUMENTS

| | | | |
|---|---|---|---|
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Ai-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,976,472 B2 | 7/2011 | Kiani |
| 7,990,382 B2 | 8/2011 | Kiani |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,130,105 B2 | 3/2012 | Al-Ali et al. |
| 8,182,443 B1 | 5/2012 | Kiani |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,265,723 B1 | 9/2012 | McHale et al. |
| 8,274,360 B2 | 9/2012 | Sampath et al. |
| 8,280,473 B2 | 10/2012 | Al-Ali |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish et al. |
| 8,374,665 B2 | 2/2013 | Lamego |
| 8,388,353 B2 | 3/2013 | Kiani et al. |
| 8,401,602 B2 | 3/2013 | Kiani |
| 8,414,499 B2 | 4/2013 | Al-Ali et al. |
| 8,418,524 B2 | 4/2013 | Al-Ali |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish et al. |
| 8,715,206 B2 | 5/2014 | Telfort et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Ai-Ali |
| 8,897,850 B2 | 11/2014 | Jochim |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,622,692 B2 | 4/2017 | Lamego et al. |
| 9,635,349 B2 * | 4/2017 | Godavarty ........... A61B 5/0073 |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Ai-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B2 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |

(56) References Cited

U.S. PATENT DOCUMENTS

| | | | |
|---|---|---|---|
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Ai-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Ai-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Ai-Ali |
| 11,684,296 B2 | 6/2023 | Vo et al. |
| 11,692,934 B2 | 7/2023 | Normand et al. |
| 11,701,043 B2 | 7/2023 | Al-Ali et al. |
| D997,365 S | 8/2023 | Hwang |
| 11,721,105 B2 | 8/2023 | Ranasinghe et al. |

(56)     References Cited

U.S. PATENT DOCUMENTS

| | | | |
|---|---|---|---|
| 11,730,379 | B2 | 8/2023 | Ahmed et al. |
| D998,625 | S | 9/2023 | Indorf et al. |
| D998,630 | S | 9/2023 | Indorf et al. |
| D998,631 | S | 9/2023 | Indorf et al. |
| D999,244 | S | 9/2023 | Indorf et al. |
| D999,245 | S | 9/2023 | Indorf et al. |
| D999,246 | S | 9/2023 | Indorf et al. |
| 11,766,198 | B2 | 9/2023 | Pauley et al. |
| D1,000,975 | S | 10/2023 | Al-Ali et al. |
| 11,803,623 | B2 | 10/2023 | Kiani et al. |
| 11,832,940 | B2 | 12/2023 | Diab et al. |
| D1,013,179 | S | 1/2024 | Al-Ali et al. |
| 11,872,156 | B2 | 1/2024 | Telfort et al. |
| 11,879,960 | B2 | 1/2024 | Ranasinghe et al. |
| 11,883,129 | B2 | 1/2024 | Olsen |
| D1,022,729 | S | 4/2024 | Forrest et al. |
| 11,951,186 | B2 | 4/2024 | Krishnamani et al. |
| 11,974,833 | B2 | 5/2024 | Forrest et al. |
| 11,986,067 | B2 | 5/2024 | Al-Ali et al. |
| 11,986,289 | B2 | 5/2024 | Dalvi et al. |
| 11,986,305 | B2 | 5/2024 | Al-Ali et al. |
| D1,031,729 | S | 6/2024 | Forrest et al. |
| 12,004,869 | B2 | 6/2024 | Kiani et al. |
| 12,014,328 | B2 | 6/2024 | Wachman et al. |
| D1,036,293 | S | 7/2024 | Al-Ali |
| D1,037,462 | S | 7/2024 | Al-Ali et al. |
| 12,029,844 | B2 | 7/2024 | Pauley et al. |
| 12,048,534 | B2 | 7/2024 | Vo et al. |
| 12,064,217 | B2 | 8/2024 | Ahmed et al. |
| 12,064,240 | B2 | 8/2024 | Vo et al. |
| 12,066,426 | B1 | 8/2024 | Lapotko et al. |
| D1,041,511 | S | 9/2024 | Indorf et al. |
| D1,042,596 | S | 9/2024 | DeJong et al. |
| D1,042,852 | S | 9/2024 | Hwang |
| 12,076,159 | B2 | 9/2024 | Belur Nagaraj et al. |
| 12,082,926 | B2 | 9/2024 | Sharma et al. |
| D1,044,828 | S | 10/2024 | Chandran et al. |
| D1,048,571 | S | 10/2024 | Yu et al. |
| D1,048,908 | S | 10/2024 | Al-Ali et al. |
| 12,106,752 | B2 | 10/2024 | Campbell et al. |
| 12,114,974 | B2 | 10/2024 | Al-Ali et al. |
| 12,126,683 | B2 | 10/2024 | Koo et al. |
| 12,127,838 | B2 | 10/2024 | Olsen et al. |
| 12,128,213 | B2 | 10/2024 | Kiani et al. |
| 12,131,661 | B2 | 10/2024 | Pauley et al. |
| D1,050,910 | S | 11/2024 | Al-Ali et al. |
| 12,178,572 | B1 | 12/2024 | Pauley et al. |
| 12,178,581 | B2 | 12/2024 | Telfort et al. |
| 12,178,852 | B2 | 12/2024 | Kiani et al. |
| D1,057,159 | S | 1/2025 | DeJong et al. |
| D1,057,160 | S | 1/2025 | DeJong et al. |
| 12,198,790 | B1 | 1/2025 | Al-Ali |
| 12,200,421 | B2 | 1/2025 | Campbell et al. |
| 12,207,901 | B1 | 1/2025 | Lapotko et al. |
| D1,060,680 | S | 2/2025 | Al-Ali et al. |
| D1,061,585 | S | 2/2025 | Indorf |
| D1,063,893 | S | 2/2025 | DeJong et al. |
| 12,220,207 | B2 | 2/2025 | Telfort et al. |
| 12,235,941 | B2 | 2/2025 | Kiani et al. |
| 12,236,767 | B2 | 2/2025 | Muhsin et al. |
| D1,066,244 | S | 3/2025 | Lim et al. |
| D1,066,672 | S | 3/2025 | Al-Ali et al. |
| D1,068,656 | S | 4/2025 | Trevisan et al. |
| D1,071,195 | S | 4/2025 | Seung |
| D1,072,836 | S | 4/2025 | Indorf |
| D1,072,837 | S | 4/2025 | Ahmed et al. |
| 12,272,445 | B1 | 4/2025 | Kiani |
| D1,078,689 | S | 6/2025 | Hwang |
| D1,079,020 | S | 6/2025 | Hwang |
| 12,336,796 | B2 | 6/2025 | Al-Ali |
| D1,083,653 | S | 7/2025 | DeJong et al. |
| D1,085,102 | S | 7/2025 | Indorf et al. |
| 12,362,596 | B2 | 7/2025 | Barker et al. |
| 12,390,114 | B2 | 8/2025 | Novak, Jr. et al. |
| D1,092,244 | S | 9/2025 | DeJong et al. |
| D1,093,406 | S | 9/2025 | Indorf et al. |
| D1,094,735 | S | 9/2025 | DeJong et al. |
| D1,095,288 | S | 9/2025 | Lim |
| D1,095,483 | S | 9/2025 | DeJong et al. |
| 12,433,524 | B2 | 10/2025 | Al-Ali et al. |
| 12,440,128 | B2 | 10/2025 | Al-Ali et al. |
| D1,102,622 | S | 11/2025 | Al-Ali et al. |
| 12,478,272 | B2 | 11/2025 | Telfort et al. |
| 12,478,293 | B1 | 11/2025 | Al-Ali et al. |
| D1,106,466 | S | 12/2025 | Avendaño et al. |
| 12,495,967 | B2 | 12/2025 | Muhsin et al. |
| 12,495,999 | B2 | 12/2025 | Al-Ali et al. |
| 12,507,952 | B2 | 12/2025 | Al-Ali et al. |
| 12,521,021 | B2 | 1/2026 | Al-Ali et al. |
| 12,521,506 | B2 | 1/2026 | Yu et al. |
| 2001/0034477 | A1 | 10/2001 | Mansfield et al. |
| 2001/0039483 | A1 | 11/2001 | Brand et al. |
| 2002/0010401 | A1 | 1/2002 | Bushmakin et al. |
| 2002/0058864 | A1 | 5/2002 | Mansfield et al. |
| 2002/0133080 | A1 | 9/2002 | Apruzzese et al. |
| 2003/0013975 | A1 | 1/2003 | Kiani |
| 2003/0018243 | A1 | 1/2003 | Gerhardt et al. |
| 2003/0144582 | A1 | 7/2003 | Cohen et al. |
| 2003/0156288 | A1 | 8/2003 | Barnum et al. |
| 2003/0212312 | A1 | 11/2003 | Coffin, IV et al. |
| 2004/0106163 | A1 | 6/2004 | Workman, Jr. et al. |
| 2005/0055276 | A1 | 3/2005 | Kiani et al. |
| 2005/0234317 | A1 | 10/2005 | Kiani |
| 2006/0073719 | A1 | 4/2006 | Kiani |
| 2006/0114457 | A1 | 6/2006 | Schmitz et al. |
| 2006/0189871 | A1 | 8/2006 | Al-Ali et al. |
| 2007/0073116 | A1 | 3/2007 | Kiani et al. |
| 2007/0180140 | A1 | 8/2007 | Welch et al. |
| 2007/0244377 | A1 | 10/2007 | Cozad et al. |
| 2008/0064965 | A1 | 3/2008 | Jay et al. |
| 2008/0094228 | A1 | 4/2008 | Welch et al. |
| 2008/0103375 | A1 | 5/2008 | Kiani |
| 2008/0221418 | A1 | 9/2008 | Al-Ali et al. |
| 2009/0036759 | A1 | 2/2009 | Ault et al. |
| 2009/0093687 | A1 | 4/2009 | Telfort et al. |
| 2009/0095926 | A1 | 4/2009 | MacNeish, III |
| 2009/0247984 | A1 | 10/2009 | Lamego et al. |
| 2009/0275844 | A1 | 11/2009 | Al-Ali |
| 2010/0004518 | A1 | 1/2010 | Vo et al. |
| 2010/0030040 | A1 | 2/2010 | Poeze et al. |
| 2010/0081912 | A1* | 4/2010 | McKenna ........... A61B 5/1455 |
| | | | 600/368 |
| 2010/0099964 | A1 | 4/2010 | O'Reilly et al. |
| 2010/0234718 | A1 | 9/2010 | Sampath et al. |
| 2010/0270257 | A1 | 10/2010 | Wachman et al. |
| 2011/0028806 | A1 | 2/2011 | Merritt et al. |
| 2011/0028809 | A1 | 2/2011 | Goodman |
| 2011/0040197 | A1 | 2/2011 | Welch et al. |
| 2011/0082711 | A1 | 4/2011 | Poeze et al. |
| 2011/0087081 | A1 | 4/2011 | Kiani et al. |
| 2011/0118561 | A1 | 5/2011 | Tari et al. |
| 2011/0137297 | A1 | 6/2011 | Kiani et al. |
| 2011/0172498 | A1 | 7/2011 | Olsen et al. |
| 2012/0123231 | A1 | 5/2012 | O'Reilly |
| 2012/0165629 | A1 | 6/2012 | Merritt et al. |
| 2012/0209084 | A1 | 8/2012 | Olsen et al. |
| 2012/0226117 | A1 | 9/2012 | Lamego et al. |
| 2012/0283524 | A1 | 11/2012 | Kiani et al. |
| 2013/0023775 | A1 | 1/2013 | Lamego et al. |
| 2013/0060147 | A1 | 3/2013 | Welch et al. |
| 2013/0096405 | A1 | 4/2013 | Garfio |
| 2013/0296672 | A1 | 11/2013 | O'Neil et al. |
| 2013/0317326 | A1 | 11/2013 | Balberg et al. |
| 2013/0345921 | A1 | 12/2013 | Al-Ali et al. |
| 2014/0166076 | A1 | 6/2014 | Kiani et al. |
| 2014/0180160 | A1 | 6/2014 | Brown et al. |
| 2014/0187973 | A1 | 7/2014 | Brown et al. |
| 2014/0275871 | A1 | 9/2014 | Lamego et al. |
| 2014/0275872 | A1 | 9/2014 | Merritt et al. |
| 2014/0316217 | A1 | 10/2014 | Purdon et al. |
| 2014/0316218 | A1 | 10/2014 | Purdon et al. |
| 2014/0323897 | A1 | 10/2014 | Brown et al. |
| 2014/0323898 | A1 | 10/2014 | Purdon et al. |
| 2015/0005600 | A1 | 1/2015 | Blank et al. |

(56) References Cited

U.S. PATENT DOCUMENTS

| | | | |
|---|---|---|---|
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0157247 A1 | 6/2015 | Weinstein |
| 2016/0196388 A1 | 7/2016 | Lamego |
| 2016/0367173 A1 | 12/2016 | Dalvi et al. |
| 2017/0024748 A1 | 1/2017 | Haider |
| 2017/0173632 A1 | 6/2017 | Al-Ali |
| 2017/0251974 A1 | 9/2017 | Shreim et al. |
| 2018/0242926 A1 | 8/2018 | Muhsin et al. |
| 2018/0247712 A1 | 8/2018 | Muhsin et al. |
| 2019/0239787 A1 | 8/2019 | Pauley et al. |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113520 A1 | 4/2020 | Abdul-Hafiz et al. |
| 2020/0138368 A1 | 5/2020 | Kiani et al. |
| 2020/0163597 A1 | 5/2020 | Dalvi et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Ai-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Ai-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |
| 2025/0037836 A1 | 1/2025 | Kiani |
| 2025/0100482 A1 | 3/2025 | Al-Ali et al. |
| 2025/0118415 A1 | 4/2025 | Olsen |
| 2025/0255764 A1 | 8/2025 | Stead |
| 2025/0278512 A1 | 9/2025 | Koo et al. |
| 2025/0281059 A1 | 9/2025 | Avendano |
| 2025/0288250 A1 | 9/2025 | Al-Ali et al. |
| 2025/0295366 A1 | 9/2025 | Al-Ali et al. |
| 2025/0302426 A1 | 10/2025 | Ha et al. |
| 2025/0311949 A1 | 10/2025 | Al-Ali et al. |
| 2025/0318761 A1 | 10/2025 | Al-Ali et al. |
| 2025/0322950 A1 | 10/2025 | Al-Ali et al. |
| 2025/0323417 A1 | 10/2025 | Rey |
| 2025/0329240 A1 | 10/2025 | Kiani |
| 2025/0344010 A1 | 11/2025 | Al-Ali et al. |
| 2026/0014333 A1 | 1/2026 | Fernkvist et al. |
| 2026/0014334 A1 | 1/2026 | Danwihl |

* cited by examiner

11

NONINVASIVE PHYSIOLOGICAL SENSOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present disclosure relates to physiological monitoring devices, systems, and methods.

BACKGROUND

Hospitals, nursing homes, and other user care facilities typically include user monitoring devices at one or more bedsides in the facility. User monitoring devices generally include sensors, processing equipment, and displays for obtaining and analyzing a medical user's physiological parameters such as blood oxygen saturation level, respiratory rate, pulse, and a myriad of other parameters. Clinicians, including doctors, nurses, and other medical personnel, use the physiological parameters and trends of those parameters obtained from user monitors to diagnose illnesses and to prescribe treatments. Clinicians also use the physiological parameters to monitor users during various clinical situations to determine whether to increase the level of medical care given to users.

Examples of non-invasive user monitoring devices include pulse oximeters. Pulse oximetry is a widely accepted noninvasive procedure for measuring the oxygen saturation level of arterial blood, an indicator of a person's oxygen supply. A pulse oximeter generally includes one or more light sources that transmit optical radiation into a portion of the body, for example a digit such as a finger, a hand, a foot, a nose, an earlobe, or a forehead. After attenuation by tissue and fluids of the portion of the body, one or more photodetection devices detect the attenuated light and output one or more detector signals responsive to the detected attenuated light. The oximeter may, in various embodiments, calculate oxygen saturation (SpO2), pulse rate, a plethysmograph waveform, perfusion index (PI), pleth variability index (PVI), methemoglobin (HbMet), carboxyhemoglobin (HbCO), total hemoglobin (HbT), glucose, among other physiological parameters, and the oximeter may display on one or more monitors the foregoing parameters individually, in groups, in trends, as combinations, or as an overall wellness or other index.

SUMMARY

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

A noninvasive physiological sensor can comprise: a first body portion and a second body portion coupled to the first body portion, the first and second body portions configured to at least partially enclose a finger of a user; and a first probe and a second probe at least partially aligned with the first probe, the first probe coupled to one or more emitters and to at least one of the first and second body portions, the first probe configured to direct optical radiation emitted from the one or more emitters toward tissue of the user's finger, the second probe coupled to one or more detectors and to at least one of the first and second body portions, the second probe configured to direct light attenuated through pulsatile blood flowing through the tissue to the one or more detectors. When the first and second body portions are rotated with respect to one another, a distance between ends of the first and second probes can be changed. When the first and second body portions are rotated with respect to one another to a first position, ends of the first and second probes can be configured to compress at least a portion of the tissue of the user, and wherein the distance between the ends of the first and second probes can define an optical radiation transmission path length. The optical radiation transmission path length can be less than ¼ inch (0.64 cm). When the first and second body portions are rotated with respect to one another to a second position, the ends of the first and second probes can be configured to move further away from one another, and wherein, at the second position, the distance between the ends can be equal to a maximum distance. At least one of the first and second body portions of the noninvasive physiological sensor can comprise: a first hole configured to receive the first probe, the first hole having a first axis running therethrough; and a second hole configured to receive the second probe, the second hole having a second axis running therethrough; wherein the first axis of the first hole and the second axis of the second hole are substantially aligned such that, when the first probe passes through the first hole into an interior space defined by the first and second body portions and the second probe passes through the second hole into the interior space, the ends of the first and second probes oppose one another and compress the tissue on the finger of the user. The first hole can extend through a first side of the first body portion and wherein the second hole extends through a second side of the first body portion, the second side opposite to the first side, and wherein the first body portion can be shaped to conform to the finger of the user. The noninvasive physiological sensor can further comprise a first probe guide and a second probe guide, and wherein the first probe can be at least partially retained by the first probe guide and the second probe can be at least partially retained by the second probe guide, wherein the first probe guide can comprise a first through-hole sized to receive the first probe and wherein the second probe guide can comprise a second through-hole sized to receive the second probe. The noninvasive physiological sensor can further comprise a joint configured to rotatably couple the first body portion to the second body portion and allow the first body portion to rotate about a transverse axis of the sensor, the transverse axis being generally perpendicular to a longitudinal axis of the sensor extending along a length of the sensor. The joint can comprise a first hinge extending from the first body portion, a second hinge extending from the second body portion, and a pin configured to extend through holes in the first and second hinges and couple the first and second hinges to one another. The end of at least one of the first and second probes can be angled.

A method of measuring a physiological parameter of a user can comprise: moving a first end of a first probe towards a first end of a second probe to compress tissue of a user; emitting optical radiation from at least one emitter through a second end of the first probe, the second end of the first probe being opposite to the first end of the first probe; directing the emitted optical radiation to the compressed tissue of the user with the first probe; permitting at least a portion of the emitted optical radiation to pass through a second end of the second probe after attenuation by pulsatile blood flowing in the compressed tissue, the second end of the second probe being opposite the first end of the second probe; directing the at least a portion of the emitted optical radiation to a detector with the second probe; and determining the physiological parameter based on the optical radiation detected by the detector. The method can further comprise detecting a first amount of optical radiation emitted by the at least one emitter with an $I_0$ detector. The method can further comprise comparing the first amount of optical radiation detected by the $I_0$ detector with a second amount of optical radiation detected by the detector, wherein the physiological parameter is determined based on said comparison. The step of moving the first end of the first probe towards the first end of the second probe to compress the tissue of the user can comprise moving the first ends of the first and second probes toward one another such that the first ends substantially align with one another, and wherein a distance between the first ends of the first and second probes defines an optical radiation transmission path length. The optical radiation transmission path length can be less than ¼ inch (0.64 cm). The first probe can comprise a first optical fiber and the second probe can comprise a second optical fiber.

A noninvasive physiological monitoring system can comprise: a noninvasive physiological sensor comprising a first body portion and a second body portion coupled to the first body portion, the first and second body portions configured to enclose a portion of a user's body and rotate relative to one another; a first probe and a second probe, each of the first and second probes coupled to at least one of the first and second body portions such that rotation of the first body portion with respect to the second body portion in a first rotational direction causes first ends of the first and second probes to move in a direction towards each other to compress tissue of the portion of the user's body; an emitter assembly comprising one or more emitters and one or more emitter fibers coupled to the one or more emitters, the one or more emitter fibers coupled to a second end of the first probe and configured to direct light emitted from the one or more emitters to the first probe, wherein the first probe is configured to direct the emitted light towards the tissue of the user; and a first detector coupled to a second end of the second probe, wherein the second probe is configured to collect at least a portion of the light after attenuation through the tissue of the user and guide the attenuated light to the first detector. The noninvasive physiological monitoring system can further comprise an $I_0$ detector configured to detect an amount of light emitted from the one or more emitters through the one or more emitter fibers. The noninvasive physiological monitoring system can further comprise: a third probe coupled to at least one of the first and second body portions such that rotation of the first body portion with respect to the second body portion in the first rotational direction causes a first end of the third probe to move along with the first end of the first probe in the direction towards the second probe to compress the tissue of the portion of the user's body; and a second detector coupled to a second end of the third probe, wherein the third probe is configured to collect at least a portion of the light after attenuation through the tissue of the user and guide the attenuated light to the second detector. At least one of the first ends of the first and second probes can be angled.

A noninvasive physiological sensor configured to be secured to a finger of a user can comprise an upper sensor body including a top surface and a bottom surface facing a direction opposite to the top surface and a lower sensor body. The lower sensor body can include a top surface configured to face the bottom surface of the upper sensor body when the noninvasive physiological sensor is in use and a bottom surface facing a direction opposite to the top surface of the lower sensor body. A portion of the top surface can be shaped to conform to a finger of the user. The lower sensor body can comprise a first hole on a first side of the lower sensor body configured to allow a first optical fiber to pass therethrough to an interior space defined by the lower sensor body and a second hole on a second side of the lower sensor body configured to allow a second optical fiber to pass therethrough to the interior space. The noninvasive physiological sensor can further comprise a joint configured to rotatably couple the upper sensor body to the lower sensor body and allow the upper sensor body to rotate about a transverse axis of the device, the transverse axis being generally perpendicular to a longitudinal axis that extends through a length of the device. The joint can include: a first coupling portion extending from the bottom surface of the upper sensor body towards the top surface of the lower sensor body, the first coupling portion comprising a first hole; a second coupling portion extending from the top surface of the lower sensor body towards the bottom surface of the upper sensor body, the second coupling portion comprising a second hole; and a pin configured to extend through the first hole of the first coupling portion and the second hole of the second coupling portion. The noninvasive physiological sensor can further comprise a swivel mechanism including a first arm extending from a first side of the upper sensor body and a second arm extending from a second side of the upper sensor body. The first arm can comprise a first slot configured to permit the first optical fiber to pass therethrough and the second arm can comprise a second slot configured to permit the second optical fiber to pass therethrough, the first and second arms extending outside of the first and second sides of the lower sensor body. The noninvasive physiological sensor can further comprise a first fiber guide including a first through-hole configured to permit the first optical fiber to pass therethrough, the first fiber guide positioned adjacent to the first side of the lower sensor body so as to align the first through-hole with the first hole of the lower sensor body, the first fiber guide configured to at least partially secure the first optical fiber. The noninvasive physiological sensor can further comprise a second fiber guide including a second through-hole configured to permit the second optical fiber to pass therethrough, the second fiber guide positioned adjacent to the second side of the lower sensor body so as to align the second through-hole with the second hole of the lower sensor body, the second fiber guide configured to at least partially secure the second optical fiber. The swivel mechanism can be configured such that, when the upper sensor body rotates about the transverse axis in a direction towards the lower sensor body, the first and second arms of the swivel mechanism apply a force to the first and second fiber guides so as to move the first and second optical fibers toward each other within the interior space of the lower sensor body and compress a portion of the finger of the user. The first and second arms of the swivel mechanism can each comprise a top end secured to the upper sensor body and a bottom end opposite the top end, wherein the first and second arms flare outward in a direction parallel to the transverse axis from the top end to the bottom end. The force applied by the first and second arms of the swivel mechanism to the first and second fiber guides can be caused by rotation of the upper sensor body from a first position, where the fiber guides are contacting the bottom ends of the first and second arms, to a second position, where the fiber guides are contacting a segment of the first and second arms between the top and bottom ends. The first optical fiber can be configured to couple to one or more emitters, the one or more emitters configured to emit light at one or more wavelengths, and wherein the second optical fiber can be configured to couple to one or more detectors, the one or more detectors configured to detect light attenuated by the portion of the user's finger. The portion of the top surface of the lower sensor body shaped to conform to the finger of the user can be sloped from a first flat edge along the first side of the lower sensor body to a middle portion of the top surface of the lower sensor body and can be sloped from a second flat edge along the second side of the lower sensor body to the middle portion. The first and second holes of the lower sensor body can generally align with each other. The lower sensor body can further comprise an opening positioned between the first and second holes of the lower sensor body and configured to permit inspection of the compressed portion of the user's finger. The lower sensor body can further comprise one or more legs on the bottom surface, the one or more legs can be configured to allow the device to sit upright when placed atop a surface. The lower sensor body can further comprise a recess located on the first side of the lower sensor body configured to allow a portion of the first arm of the swivel mechanism to fit therewithin. A plane of the recess of the lower sensor body can be inclined with respect to a plane of the top surface of the lower sensor body so as to conform to the shape and orientation of the first arm of the swivel mechanism. The lower sensor body can further comprise a recess located on the first side of the lower sensor body and configured to allow a portion of the first fiber guide to fit therewithin. A cross-section of the first fiber guide can be cylindrical along at least a portion of a length of the first fiber guide. Cross-sections of the first and second fiber guides can be cylindrical along at least a portion of lengths of the first and second fiber guides. The noninvasive physiological sensor can further comprise a biasing member having a first end configured to fit within a first recess in the bottom surface of the upper sensor body and a second end configured to fit within a second recess in the top surface of the lower sensor body. The biasing member can be a spring. Each of the first and second arms of the swivel mechanism can comprise a stopper on an interior-facing surface of the arms configured to contact edges of the top surface of the lower body when the device is in a closed position, the stoppers configured to prevent the upper sensor body from rotating beyond a limit so as to protect the user's finger from injury. The stoppers can have a rectangular cross-section and have bottom surfaces that lay flush against surfaces of the edges of the top surface of the lower body when the device is in the closed position, the stoppers. The first and second arms of the swivel mechanism can extend from the upper sensor body and curve towards a back portion of the device. The first and second arms of the swivel mechanism can extend below the bottom surface of the lower sensor body when the device is in a closed position. The first coupling portion can comprise a first and second hinge. The second coupling portion can comprise a third and fourth hinge. The first and second hinges of the first coupling portion can be positioned between the third and fourth hinges of the second coupling portion when the noninvasive physiological sensor is in use. The bottom surface of the upper sensor body can comprise a recessed portion shaped to correspond with a shape of a top end of the second coupling portion so as to facilitate rotation of the upper sensor body with respect to the second coupling portion. The top surface of the lower sensor body can comprise a recessed portion shaped to correspond with a shape of a bottom end of the first coupling portion so as to facilitate rotation of the lower sensor body with respect to the first coupling portion. The first and second slots of the first and second arms of the swivel mechanism have slot lengths corresponding to an optimal rotation of the upper sensor body with respect to the lower sensor body. The slot lengths can be at least 50% of lengths of the first and second arms of the swivel mechanism.

A noninvasive physiological sensor configured to be secured to a user can comprise: an upper sensor body; a lower sensor body; and a joint configured to rotatably couple the upper sensor body to the lower sensor body and allow the upper sensor body to rotate about a transverse axis of the device generally perpendicular to a longitudinal axis of the device. At least one of the upper sensor body and lower sensor body can be shaped to conform to a finger of the user. The lower sensor body can comprise a first hole configured to allow a first optical fiber to pass there through to an interior space defined by the lower sensor body and a second hole configured to allow a second optical fiber to pass there through to the interior space, and wherein the first hole and the second hole are aligned. The upper sensor body and lower sensor body can be configured such that, when, rotated about the transverse axis of the device, the first and second optical fibers are moved toward each other within the interior space defined by the lower sensor body to compress a portion of the user's finger when the finger is placed within the device. The upper sensor body can comprise a top surface and a bottom surface facing a direction opposite to the top surface, and wherein the lower sensor body can comprise a top surface configured to face the bottom surface of the upper sensor body when the noninvasive physiological sensor is in use and a bottom surface facing a direction opposite to the top surface of the lower sensor body. The top surface can be shaped to conform to the finger of the user, and wherein the first hole can be positioned on a first side of the lower sensor body and the second hole can be positioned on a second side of the lower sensor body. The noninvasive physiological sensor can further comprise a swivel mechanism comprising a first arm extending from a first side of the upper sensor body and a second arm extending from a second side of the upper sensor body. The first arm can comprise a first slot configured to permit the first optical fiber to pass therethrough and the second arm can comprise a second slot configured to permit the second optical fiber to pass therethrough. The noninvasive physiological sensor can further comprise a first fiber guide coupled to the first optical fiber and positioned adjacent to the first side of the lower sensor body and a second fiber guide coupled to the second optical fiber and positioned adjacent to the second side of the lower sensor body. When the upper sensor body rotates about the transverse axis towards the lower sensor body, the arms of the swivel mechanism can engage the first and second fiber guides to move the first and second optical fibers toward each other and compress the tissue of the user. The first fiber guide can comprise a first through-hole configured to permit the first optical fiber to pass therethrough, the first fiber guide can be positioned adjacent to the first side of the lower sensor body so as to align the first through-hole with the first hole of the lower sensor body, the first fiber guide can be configured to at least partially secure the first optical fiber. The second fiber guide can comprise a second through-hole configured to permit the second optical fiber to pass therethrough, the second fiber guide positioned adjacent to the second side of the lower sensor body so as to align the second through-hole with the second hole of the lower sensor body, the second fiber guide configured to at least partially secure the second optical fiber. The first and second arms of the swivel mechanism can apply a force to the first and second fiber guides so as to move the first and second optical fibers toward each other within the interior space of the lower sensor body and compress the portion of the finger of the user. The joint can comprise: a first coupling portion extending from the bottom surface of the upper sensor body towards the top surface of the lower sensor body, the first coupling portion comprising a first hole; a second coupling portion extending from the top surface of the lower sensor body towards the bottom surface of the upper sensor body, the second coupling portion comprising a second hole; and a pin configured to extend through the first hole of the first coupling portion to the second hole of the second coupling portion. The order by which the pin extends through the first and second holes can be changed.

A method of measuring a physiological parameter of a user can comprise: positioning a finger of the user within a noninvasive physiological measurement sensor, wherein the noninvasive physiological sensor comprises an upper sensor body and a lower sensor body, and wherein at least one of the upper sensor body and lower sensor body is shaped to conform to the finger of the user, the lower sensor body comprising a first hole configured to allow a first optical fiber to pass there through to an interior space defined by the lower sensor body and a second hole configured to allow a second optical fiber to pass therethrough to the interior space; moving the first and second optical fibers through the first and second holes of the lower sensor body toward each other within the interior space to compress a portion of the finger of the user; transmitting light, by an emitter through the first optical fiber through the portion of the user's finger; and detecting, with a detector, light attenuated by the portion of the user's finger. The upper sensor body can include a top surface and a bottom surface facing a direction opposite to the top surface. The lower sensor body can include a top surface configured to face the bottom surface of the upper sensor body when the noninvasive physiological sensor is in use and a bottom surface facing a direction opposite to the top surface of the lower sensor body, the top surface shaped to conform to the finger of the user. The first hole can be located on a first side of the lower sensor body and the second hole can be located on a second side of the lower sensor body. Moving the first and second optical fibers can comprise at least partially closing the noninvasive physiological sensor on the user's finger by rotating the upper sensor body with respect to the lower sensor body, wherein, when the upper sensor body rotates with respect to the lower sensor body, a swivel mechanism of the noninvasive physiological sensor engages with a first fiber guide coupled to the first optical fiber and with a second fiber guide coupled to the second optical fiber to move the first and second optical fibers through the first and second holes. Rotating the upper sensor body with respect to the lower sensor body can comprise rotating the upper sensor body relative to the lower sensor body about a joint of the noninvasive physiological measurement sensor. The joint can comprise: a first coupling portion extending from the bottom surface of the upper sensor body towards the top surface of the lower sensor body, the first coupling portion comprising a third hole; a second coupling portion extending from the top surface of the lower sensor body towards the bottom surface of the upper sensor body, the second coupling portion comprising a fourth hole; and a pin configured to extend through the first hole of the first coupling portion and the second hole of the second coupling portion. The method can further comprise generating an output signal based on the light detected at the portion of the user's finger.

A method of measuring a physiological parameter of a user can comprise: providing a first probe, the first probe coupled to one or more emitters configured to emit optical radiation having one or more wavelengths toward tissue at a tissue measurement site on the user; providing a second probe, the second probe coupled to one or more detectors configured to detect light emitted by the one or more emitters after attenuation by pulsatile blood flowing through the tissue at the tissue measurement site; moving ends of the first and second probes toward one another at the tissue measurement site so as to compress the tissue; emitting the optical radiation having one or more wavelengths from the one or more emitters and guiding the emitted optical radiation to the compressed tissue with the first probe; and guiding the optical radiation after attenuation by the pulsatile blood flowing through the compressed tissue with the second probe to the one or more detectors; wherein, when the ends of the first and second probes compress the tissue at the tissue measurement site, the ends of the first and second probes substantially align with one another, a distance between the ends of the first and second probes defining an optical radiation transmission path length. The first probe can comprise a first optical fiber and the second probe can comprise a second optical fiber. The one or more emitters can comprise: a first emitter configured to emit optical radiation at a first wavelength; a second emitter configured to emit optical radiation at a second wavelength; and a third emitter configured to emit optical radiation at a third wavelength; wherein the first wavelength, second wavelength, and third wavelength can be different from each other. The tissue measurement site of the user can be located on a finger of the user and the method can further comprise positioning the finger of the user within a noninvasive physiological measurement sensor to at least partially secure to the finger. The method can further comprise inserting the first probe through a first hole in the noninvasive physiological measurement sensor and inserting the second probe through a second hole in the noninvasive physiological measurement sensor. The first and second probes can be at least partially secured by the noninvasive physiological measurement sensor. The noninvasive physiological measurement sensor can comprise a first probe guide and a second probe guide, and wherein the first probe can be at least partially secured by the first fiber guide and the second probe can be at least partially secured by the second fiber guide. The noninvasive physiological measurement sensor can further comprise a first body portion and a second body portion, and the first body portion and the second body portion can be coupled to one another and configured to rotate with respect to one another, and wherein moving the ends of the first and second probes toward one another at the tissue measurement site so as to compress the tissue can comprise rotating the first body portion with respect to the second body portion. At least one of the first body portion and the second body portion can comprise a surface shaped to conform to the finger of the user. Moving the ends of the first and second probes toward one another at the tissue measurement site so as to compress the tissue can comprise moving the ends together so that the optical radiation transmission path length is between ¼ inch (0.64 cm) and 1/12 inch (0.21 cm). Moving the ends of the first and second probes toward one another at the tissue measurement site so as to compress the tissue can comprise moving the ends together so that the optical radiation transmission path length is between ⅙ inch (0.42 cm) and ⅒ inch (0.25 cm).

A noninvasive physiological sensor can comprise: a first body portion and a second body portion coupled to the first body portion, the first and second body portions configured to at least partially enclose and secure a finger of a user; a first hole configured to receive a first probe, the first probe coupled to one or more emitters configured to emit optical radiation having one or more wavelengths toward tissue on the finger of the user, the first hole having a first axis running therethrough; a second hole configured to receive a second probe coupled to one or more detectors configured to detect light emitted by the one or more emitters after attenuation by pulsatile blood flowing through the tissue on the finger of the user, the second hole having a second axis running therethrough; wherein the first axis of the first hole and the second axis of the second hole are substantially aligned such that, when the first probe is inserted through the first hole into an interior space defined between the first and second body portions and the second probe is inserted through the second hole into the interior space, ends of the first and second probes oppose one another and compress the tissue on the finger of the user, a distance between the ends of the first and second probes defining an optical radiation transmission path length. The noninvasive physiological sensor can further comprise: a first probe guide and a second probe guide, and the first probe can be at least partially secured by the first probe guide and the second probe can be at least partially secured by the second probe guide. The noninvasive physiological sensor can further comprise a joint configured to rotatably couple the first body portion to the second body portion and allow the first body portion to rotate about a transverse axis of the sensor generally perpendicular to a longitudinal axis of the sensor running between the first body portion and the second body portion. The sensor can be configured such that rotation of the first body portion with respect to the second body portion causes the first and second probe guides to move the first and second probes toward one another to compress the tissue of the user. The first hole can extend through a first side of the first body portion and the second hole can extend through a second side of the first body portion. The second side can be opposite to the first side and the first body portion can be shaped to conform to the finger of the user. The optical radiation transmission path length can be between ¼ inch (0.64 cm) and 1/12 inch (0.21 cm). The optical radiation transmission path length can be between ⅙ inch (0.42 cm) and ⅒ inch (0.25 cm).

A noninvasive physiological sensor can comprise: a first body portion and a second body portion coupled to the first body portion, the first and second body portions configured to at least partially enclose a finger of a user; and a first probe and a second probe at least partially aligned with the first probe, the first probe coupled to one or more emitters configured to emit optical radiation toward tissue of the patient and the second probe coupled to one or more detectors configured to detect light emitted by the one or more emitters after attenuation by pulsatile blood flowing through the tissue; wherein, when the first and second body portions are rotated with respect to one another, a distance between ends of the first and second probes is changed. When the first and second body portions are rotated with respect to one another to a first position, ends of the first and second probes can be configured to compress at least a portion of the tissue of the user, and the distance between the ends of the first and second probes can define an optical radiation transmission path length. The optical radiation transmission path length can be less than ¼ inch (0.64 cm). When the first and second body portions are rotated with respect to one another to a second position, the ends of the first and second probes can be configured to move further away from one another, and, at the second position, the distance between the ends can be equal to a maximum distance. The first position can be a position in which the sensor is closed or partially closed. The second position can be a position in which the sensor is open or partially open. The noninvasive physiological sensor can further comprise: a first hole configured to receive the first probe, the first hole having a first axis running therethrough; a second hole configured to receive the second probe, the second hole having a second axis running therethrough; wherein the first axis of the first hole and the second axis of the second hole are substantially aligned such that, when the first probe passes through the first hole into an interior space defined by the first and second body portions and the second probe passes through the second hole into the interior space, the ends of the first and second probes oppose one another and compress the tissue on the finger of the user. Each of the first and second probes can be coupled to at least one of the first and second body portions. Each of the first and second probes can be indirectly coupled to at least one of the first and second body portions. Each of the first and second probes can be at least partially retained within spacers, and the spacers can be configured to contact portions of sides of the first and second body portions. The portions of the sides of the first and second body portions can comprise arms extending from the first body portion and recessed portions of the sides of the second body portion. The spacers can comprise apertures sized to allow the first and second probes to extend therethrough. The noninvasive physiological sensor can comprise a first probe guide and a second probe guide. The first probe can be at least partially retained by the first probe guide and/or the second probe can be at least partially retained by the second probe guide. The noninvasive physiological sensor can further comprise a joint configured to rotatably couple the first body portion to the second body portion and allow the first body portion to rotate about a transverse axis of the sensor, the transverse axis being generally perpendicular to a longitudinal axis of the sensor running between the first body portion and the second body portion, the longitudinal axis extending along a length of the sensor. The first hole can extend through a first side of the first body portion and/or the second hole can extend through a second side of the first body portion. The second side can be opposite to the first side and the first body portion can be shaped to conform to the finger of the user.

A method of measuring a physiological parameter of a user can comprise: providing a first probe configured to couple to at least one emitter, the at least one emitter configured to emit optical radiation toward tissue of a user; providing a second probe configured to couple to at least one detector, the at least one detector configured to detect light emitted by the at least one emitter after attenuation by pulsatile blood flowing through the tissue; moving ends of the first and second probes toward one another to compress the tissue; emitting the optical radiation from the at least one emitter and guiding the emitted optical radiation to the compressed tissue with the first probe; and guiding the optical radiation after attenuation through the compressed tissue with the second probe to the at least one detector. When the ends of the first and second probes compress the tissue of the user, the ends of the first and second probes can substantially align with one another and a distance between the ends of the first and second probes can define an optical radiation transmission path length. The optical radiation transmission path length can be less than ¼ inch (0.64 cm). The first probe can comprise a first optical fiber and the second probe can comprise a second optical fiber. The at least one emitter can comprise: a first emitter configured to emit optical radiation at a first wavelength; a second emitter configured to emit optical radiation at a second wavelength; and a third emitter configured to emit optical radiation at a third wavelength. The first wavelength, second wavelength, and/or third wavelength can be different from each other. The tissue can be located on a finger of the user and the method can further comprise positioning the finger within a noninvasive physiological measurement sensor configured to at least partially secure to the finger. The method can further comprise inserting the first probe at least partially through a first hole in the noninvasive physiological measurement sensor and inserting the second probe at least partially through a second hole in the noninvasive physiological measurement sensor. The first and second probes can be at least partially retained by the noninvasive physiological measurement sensor. The noninvasive physiological measurement sensor can comprise a first probe guide and a second probe guide, and the first probe can be at least partially secured by the first fiber guide and the second probe can be at least partially secured by the second fiber guide. The noninvasive physiological measurement sensor can further comprise a first body portion and a second body portion. The first body portion and the second body portion can be coupled to one another and configured to rotate with respect to one another. Moving the ends of the first and second probes toward one another to compress the tissue can comprise rotating the first body portion with respect to the second body portion. At least one of the first body portion and the second body portion can comprise a surface shaped to conform to the finger of the user.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIG. 1O illustrates a block diagram depicting an embodiment of a computer hardware system configured to run software for implementing one or more embodiments of the physiological measurement system described herein.

FIG. 2I illustrates a top perspective view of a lower sensor body of the noninvasive physiological sensor of FIG. 2A with a finger placed therewithin.

DETAILED DESCRIPTION

Embodiments of the present disclosure will now be described with reference to the accompanying figures, wherein like numerals refer to like elements throughout. The following description is merely illustrative in nature and is in no way intended to limit the disclosure, its application, or uses. It should be understood that steps within a method may be executed in different order without altering the principles of the present disclosure. Furthermore, embodiments disclosed herein can include several novel features, no single one of which is solely responsible for its desirable attributes or which is essential to practicing the systems, devices, and methods disclosed herein. Additionally, aspects and features of the various embodiments of the devices, systems, and methods disclosed herein can be combined and/or integrated with one another without departing from the scope of the present disclosure.

Figure 1A:
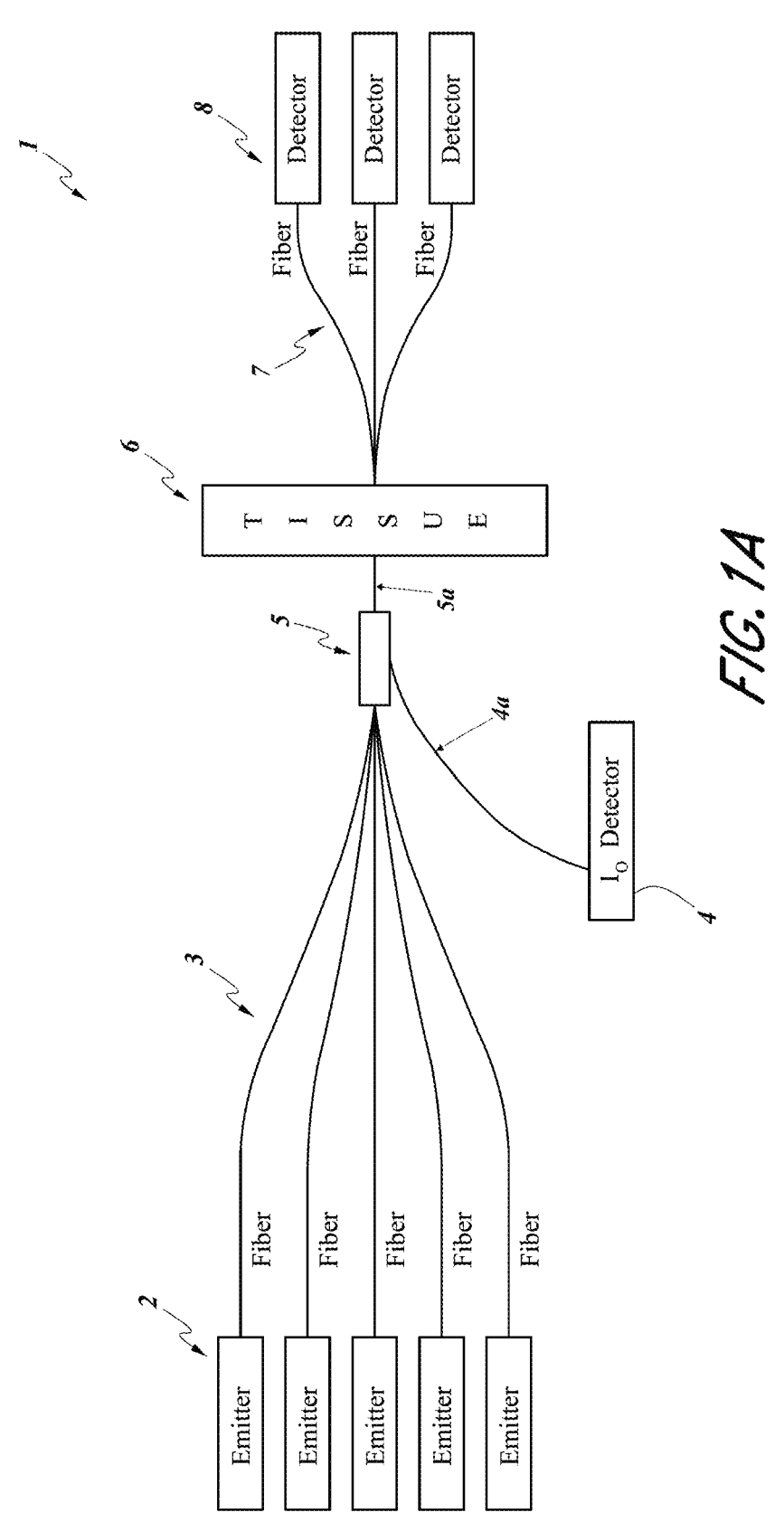
FIG. 1A illustrates a schematic diagram depicting a physiological measurement system configured to generate a plethysmograph through a tissue of a user that can be used in combination with a noninvasive physiological sensor in accordance with aspects of this disclosure.

FIG. 1A illustrates a schematic diagram depicting a physiological measurement system 1 configured to generate a plethysmograph through a tissue 6 of a user that can be used alone or in combination with a noninvasive physiological measurement device, such as noninvasive physiological sensor 10 described herein. The physiological measurement system 1 can include one or more emitters 2 and/or one or more detectors 8. The one or more emitters 2 can be light-emitting diodes (LED), for example. The one or more detectors 8 can be photodetectors, photodiodes, phototransistors, and/or the like. As shown, each of the one or more emitters 2 can be coupled to a fiber 3 (such as an optical fiber) to help collect, guide, and/or transmit the emitted light. As also shown, fibers 3 can be coupled together (for example, bundled together) by a coupler 5 and can join and/or meet an end of a fiber 5a, which can contact (for example, probe) tissue 6 of a user as discussed in more detail below. The physiological measurement system 1 can include an incident light ($I)_o$ detector 4 that can detect the light emitted by the one or more emitters 2 via fibers 3 before such light is transmitted to and/or through the tissue 6. Thus, the light detected by the $I_0$ detector 4 can act as a reference point by which light detected by the one or more detectors 8 can be compared. Such comparison can allow for a more refined analysis of physiological parameters determined based on light attenuated through the tissue 6. In some embodiments, $I_0$ detector 4 is connected to a fiber 4a which can connect and/or pass through coupler 5 (also referred to herein as "adapter"). Coupler 5 can join fibers 3 and fiber 4a therewithin, and can allow an end of fiber 5a to meet an end of the joined fibers 3 and 4a. Fiber 5a can receive the light transmitted via fibers 3 and can transmit such light to the tissue 6, for example, when fiber 5a contacts tissue 6 as discussed herein. Alternatively, in some embodiments, $I_0$ detector 4 is integrated into coupler 5. In some embodiments, $I_0$ detector 4 is separate from coupler 5. The tissue 6 can be any portion of a user's body. For example, the tissue 6 can be a portion of a user's finger, toe, nose, or other portion of the user's body. As shown in FIGS. 1A, each of the one or more detectors 8 can be coupled to fibers 7 (such as optical fibers) which can collect light after attenuation through tissue 6. While FIG. 1A shows the fibers 7 joined together proximate tissue 6, the fibers 7 can alternatively be spaced apart from each other when placed at the tissue 6. For example, each of the fibers 7 shown in FIG. 1A can be spaced apart and positioned adjacent tissue 6. Such spacing of the fibers 7 can allow the fibers 7 to contact different portions of the tissue 6 (for example, finger) and/or probe different path length of the tissue 6. Fibers 7 can collect attenuated light after transmission through tissue 6 and guide the attenuated light to the one or more detectors 8. While not shown in FIG. 1, in some embodiments, system 1 includes a coupler similar to coupler 5 which is on the detector side of tissue 6 that couples end of fibers 7 with each other and/or to a separate fiber that probes tissue 6, similar to fiber 5a.

The coupling of the one or more emitters 2 with fibers 3 can advantageously allow light emitted from the one or more emitters 2 at a wide, divergent angle and/or direction to be guided, focused, and/or directed as a point source (for example, via an end of a fiber 3). Such coupling can allow physical path length to be constant during transmission of light via the one or more fibers 3, which can allow the emitters 2 to transmit light at and/or through highly absorbing mediums at a single or multiplicity of wavelengths and/or wavelength regions. Such wavelengths can include any visible, near infrared (NIR), mid infrared (MIR) or any other spectroscopic band measurements, for example. In some embodiments, system 1 includes a plurality of emitters 2 (such as two, three, four, five, six, seven, or eight or more emitters 2) and each of the plurality of emitters 2 emit light at a different wavelength or wavelength region. Additionally, the joining or meeting of the fibers 3 in the coupler 5 with fiber 5a can allow for a smaller amount of contact area with tissue 6 since only fiber 5a contacts the tissue 6, which can reduce user discomfort. The coupling of the one or more emitters 2 with fibers 3 can also provide reduction in light leakage. The use of fibers 3 and/or fiber 5a can also allow a beam angle of the emitted light from the emitters 2 to be adjusted as desired. The integration of fiber 4a within coupler 5 can advantageously allow real time measurement of the amount of light emitted by the emitters 2 and/or transmitted by fibers 3 by the $I_0$ detector 4 in an efficient and convenient manner.

As shown in FIG. 1A, the coupling of the one or more emitters 2 and/or the one or more detectors 8 with fibers 3, fibers 7, and/or fiber 5a can allow the system to be configured such that fiber 5a and one or more of the fibers 7 can face each other. For example, fiber 5a and one or more of the fibers 7 can at least partially align along a longitudinal axis running through the fibers 5, 7 and/or can be parallel to one another so that light can be transmitted through the tissue 6 and efficiently collected by fibers 7. Such alignment can allow a greater portion of transmitted and attenuated light to be collected by the fibers 7 and passed to the one or more detectors 8, thus increasing the accuracy of physiological measurements. Further, as discussed below, the fiber(s) 3, 5a and fiber(s) 7 can be pressed against tissue 6 so as to compress a portion of the tissue 6 and/or partially isolate the portion of tissue 6 to increase accuracy of physiological measurements. For example, as discussed below, the compressed and/or isolated portion of tissue 6 can be a portion of a user's finger that does not include bone. Transmitting and detecting attenuated light through such compressed and/or isolated portion of tissue 6 can allow physiological measurements to be taken without transmitting light through the user's bone, which can increase the accuracy of such measurements. In addition, fibers 5a can probe (for example, press into) different portions of tissue 6 in order to increase the ability of the transmitted light to penetrate beyond the epidermis layer of skin to deeper regions of the tissue 6 where the blood vessels reside so as to obtain more accurate physiological measurements. For example, such probing with fibers 5a can reduce the tendency for the transmitted light to remain in the epidermis layer without traveling through the blood vessels in the deeper regions of the tissue 6.

Figure 1B:
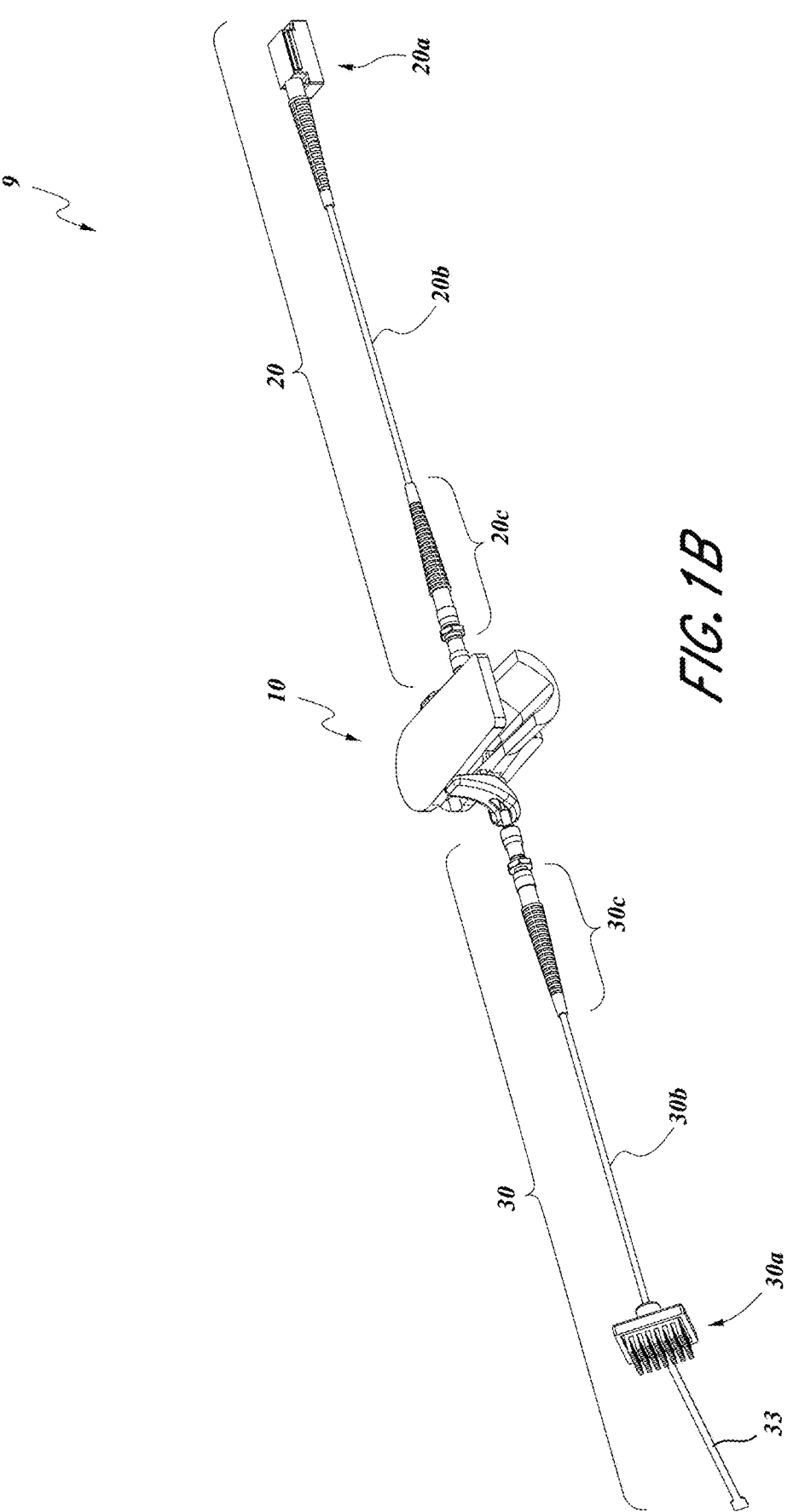
FIG. 1B illustrates an embodiment of a physiological measurement system in accordance with aspects of this disclosure.

Any or all of the above-described components of the physiological measurement system 1 can be used alongside the noninvasive physiological sensor 10 discussed below. FIG. 1B illustrates an embodiment of a physiological measurement system 9 that can be used alongside a noninvasive physiological sensor 10. Physiological measurement system 9 can include some or many of the features described with respect to physiological measurement system 1. As shown, physiological measurement system 9 includes an emitter assembly 20 which can include an emitter package 20a, a fiber 20b (which can be an optical fiber), and a coupler 20c. Emitter package 20a can include one or a plurality of emitters (such as two, three, four, five, six, seven, or eight or more emitters) which emit light at the same or different wavelengths or wavelength regions, similar to that discussed above. The emitter(s) within the emitter package 20a can be light emitting diodes (LEDs), for example. Where the emitter package 20a includes a plurality of emitters, each of the plurality of emitters can be coupled to a fiber (similar to fiber 3) which can be bundled inside fiber 20b. Coupler 20c can join the fiber 20b to a single fiber (that can be similar or identical to fiber 5a) which can be held by a portion of sensor 10 and can contact a portion of tissue of a user. Coupler 20c can include a mating sleeve connector discussed in more detail below with reference to FIGS. 1D and 1F. An end of the bundled fiber 20b and an end of the single fiber (that can be similar or identical to fiber 5a) can be positioned within the mating sleeve connector and spaced apart by a distance (such as distance di discussed with reference to FIG. 1F) such that light transmitted by the plurality of fibers within fiber bundle 20b passes to the single fiber and to tissue of a user when the single fiber contacts the tissue. As also shown, physiological measurement system 9 includes a detector assembly 30, which can include a detector 30a, a fiber 30b (such as an optical fiber), and a coupler 30c. Coupler 30c can be similar or identical to coupler 20c. Coupler 30c can include a mating sleeve connector that positions fiber 30b with respect to a single fiber similar to that described with reference to coupler 20c above.

Figure 1C:
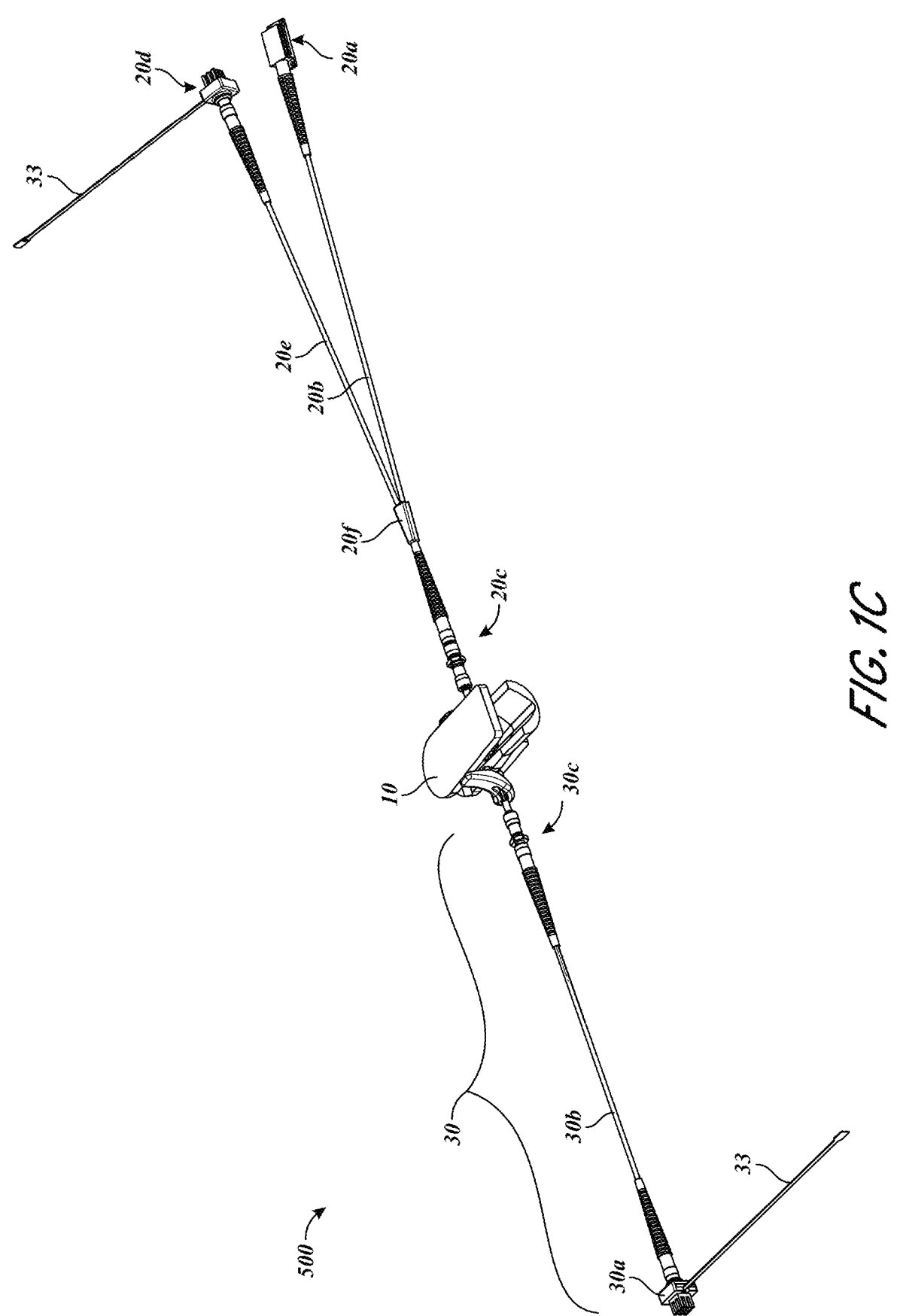
FIG. 1C illustrates another embodiment of a physiological measurement system in accordance with aspects of this disclosure.
Figure 1D:
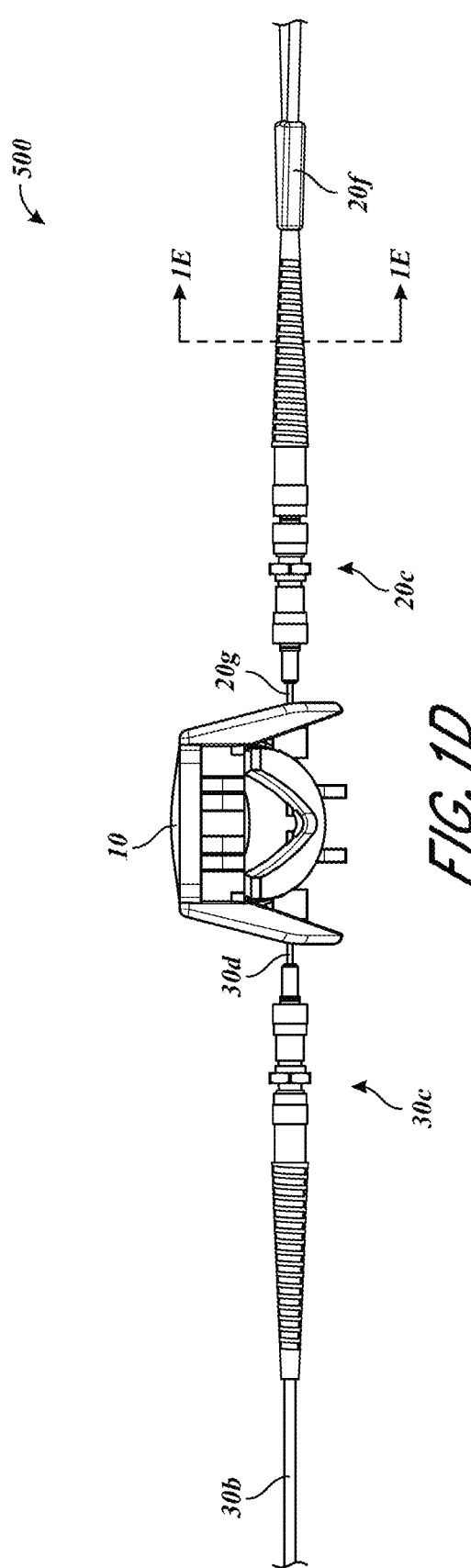
FIG. 1D illustrates a side view of the embodiment of the physiological measurement system of FIG. 1C.
Figure 1E:
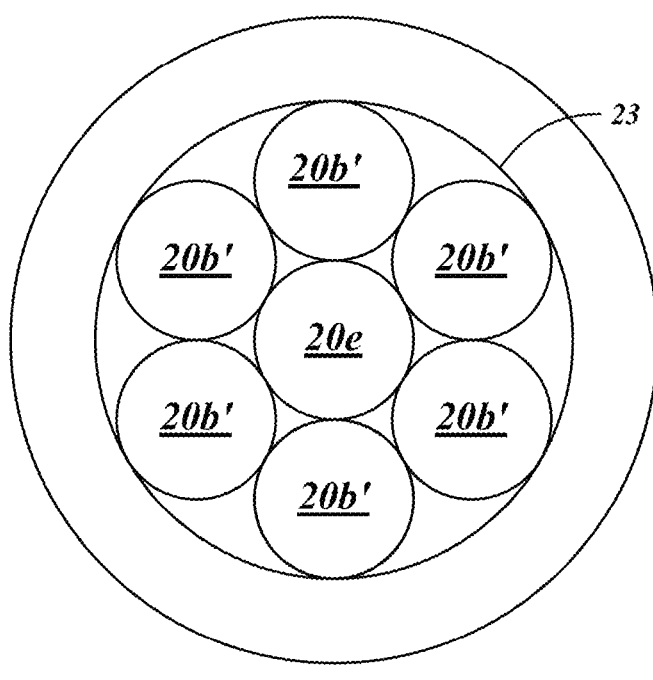
FIG. 1E illustrates an exemplary cross-section of a fiber bundle in accordance with aspects of this disclosure.
Figure 1F:
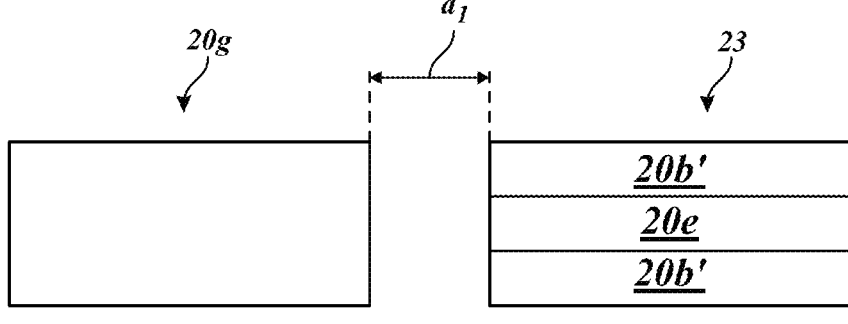
FIG. 1F illustrates an exemplary side cross-sectional view inside a fiber mating sleeve connector in accordance with aspects of this disclosure.

FIG. 1C illustrates a physiological measurement system 500 which is the same as physiological measurement system 9 in many respects. For example, system 500 includes detector assembly 30, detector 30a, fiber 30b, coupler 30c, emitter package 20a, fiber 20b, coupler 20c, and sensor 10. Additionally, system 500 includes an $I_O$ detector 20d (which can be the same in some or all respects as $I_0$ detector 4 discussed above), a fiber 20e (such as an optical fiber) connected to $I_0$ detector 20d, and an adapter 20f. As discussed previously, fiber 20b can house one or more fibers 20b' coupled to one or more emitters within emitter package 20a. Adapter 20f can join fiber 20b with fiber 20e into a fiber 23 (see FIGS. 1D-1E). FIG. 1E illustrates an exemplary cross-section through fiber 23. As shown, the one or more fibers 20b' connected to the one or more emitters of the emitter package 20a can be positioned within fiber 23 adjacent, proximate, and/or surrounding fiber 20c. With reference to FIG. 1D, coupler 20c can include a mating sleeve connector (such as an FC/APC mating sleeve commercially sold by Thorlabs, Inc.) that can join fiber 23 with a single fiber 20g. FIG. 1F shows an exemplary schematic side cross-sectional view of an inside of such mating sleeve connector of coupler 20c where an end of fiber 20g is separated by an end of fiber 23 (and ends of fibers 20b', 20e) by distance $d_1$. Distance $d_1$ can be 1 mm (0.040 inch), 2 mm (0.080 inch), 3 mm (0.12 inch), 4 mm (0.16 inch), 5 mm (0.20 inch), between 0 mm and 5 mm (0.20 inch), or any value or range bounded by any combination of these values or range, although the distance can be outside these values or range in some cases. While FIG. 1E illustrates six fibers 20b', the number of fibers 20b' can be different than six. For example, the number of fibers 20b' can be one, two, three, four, five, six, seven, or eight or more and can correspond to the amount of emitters in the emitter package 20a. With reference to FIG. 1D, the detector assembly 30 can include a coupler 30c which can be similar or identical to coupler 20c. Coupler 30c can join fiber 30b with a fiber 30d in a similar manner as that described with reference to fiber 23 and fiber 20g above.

Figure 1G:
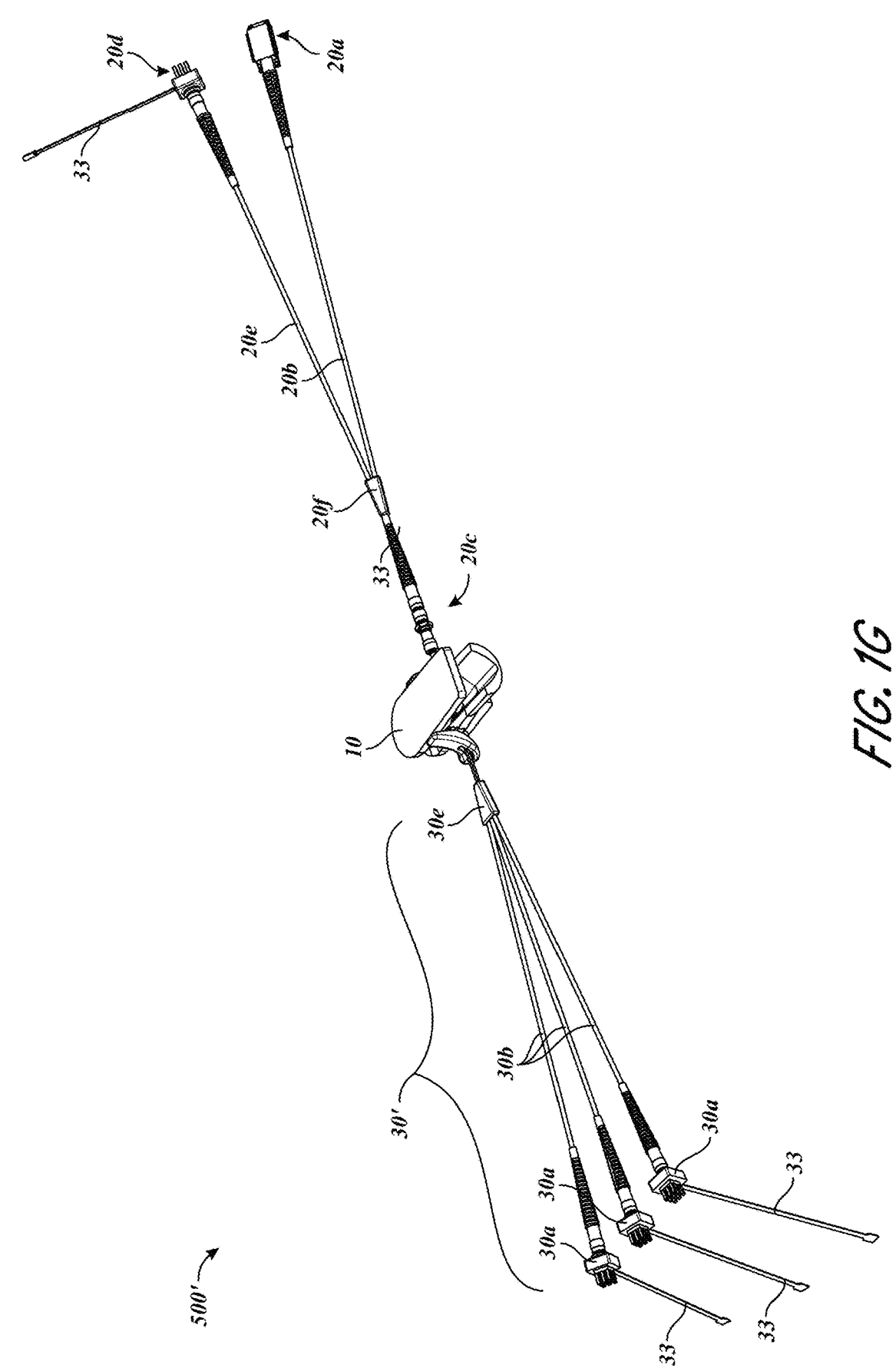
FIG. 1G illustrates another embodiment of a physiological measurement system in accordance with aspects of this disclosure.
Figure 1H:
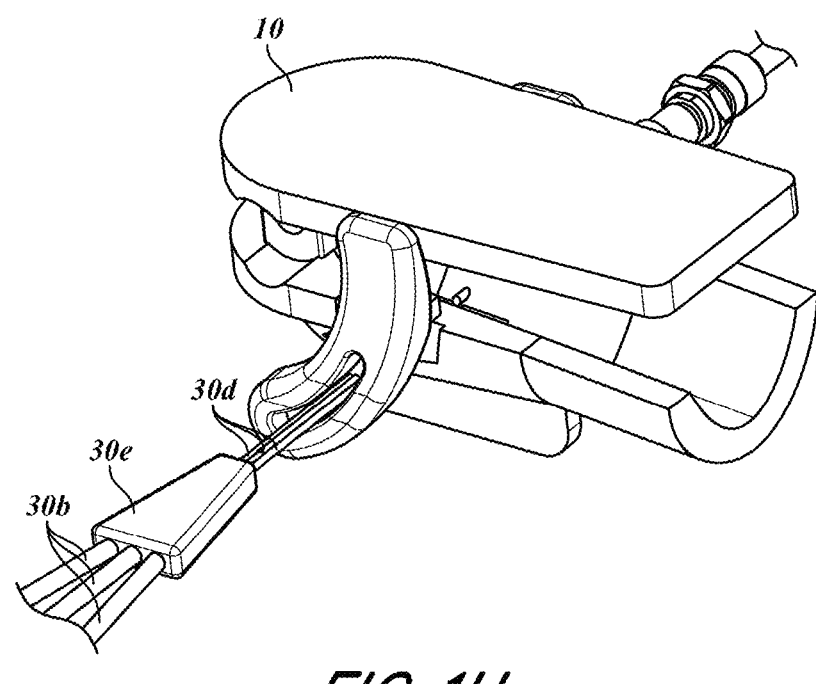
FIGS. 1H-1J illustrate enlarged views of portions of the physiological measurement system of FIG. 1G in accordance with aspects of this disclosure.

FIG. 1G illustrates a physiological measurement system 500' which is the same as physiological measurement system 500 in many respects. For example, physiological measurement system 500' can include emitter package 20a, fiber 20b, $I_0$ detector 20d, fiber 20c, adapter 20f, coupler 20c, and/or fibers 23 and 20g discussed above. Physiological measurement system 500' illustrates a detector assembly 30' that includes multiple detectors 30a coupled to fibers 30b, and an adapter 30e that can secure and/or orient portions of the fibers 30b. FIG. 1H illustrates an enlarged perspective view of the adapter 30e and the fibers 30b entering adapter 30e and also shows fibers 30d exiting adapter 30e. Ends of fibers 30d can be positioned proximate to, aligned with, and/or oriented relative to ends of fibers 30b inside adapter 30e. Adapter 30e can help position, align, and/or orient fibers 30d so as to facilitate engagement and/or interaction with sensor 10 (for example, with fiber guides 300, 300' of sensor 10 which are discussed further below).

With reference to FIGS. 1B, 1C, and 1G, the detectors 30a and/or the $I_0$ detector 4 can be connected to a cable or circuit, such as a flex circuit 33. Flex circuit 33 can transmit signals responsive to the light detected by detectors 30a and/or the $I_0$ detector 4 to a user monitor or other processing device (such as user monitor 420) for further processing and/or analysis.

Figure 1I:
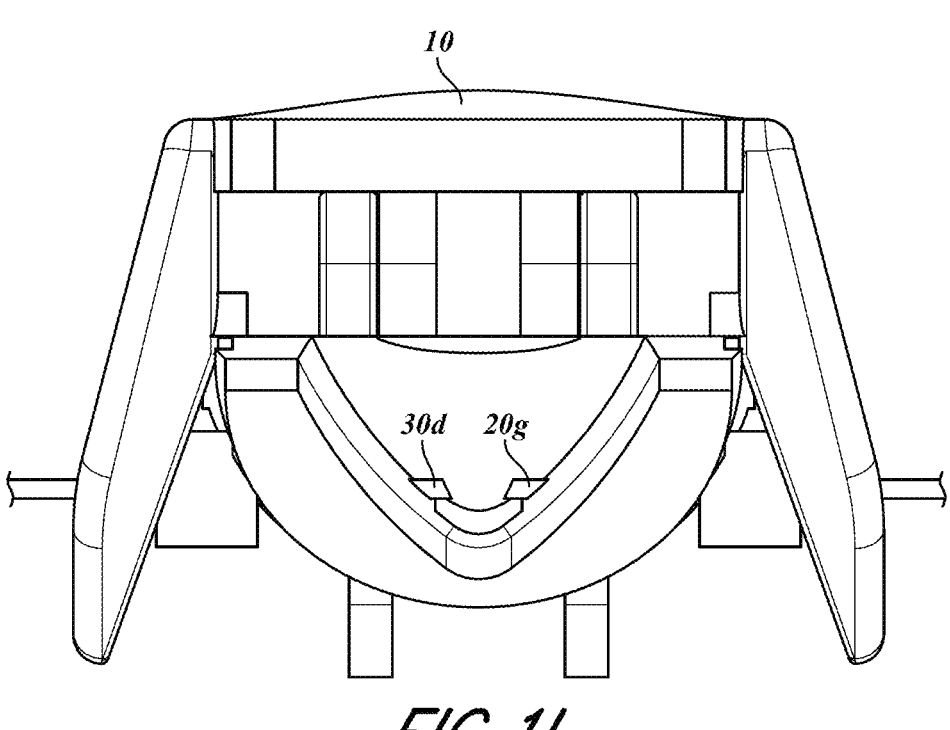
Figure 1J:
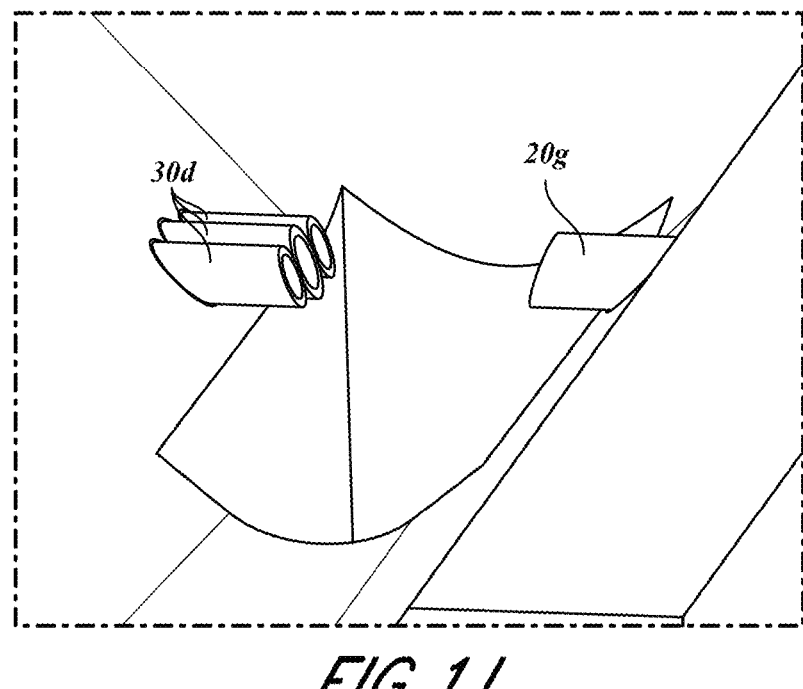
Figure 1K:
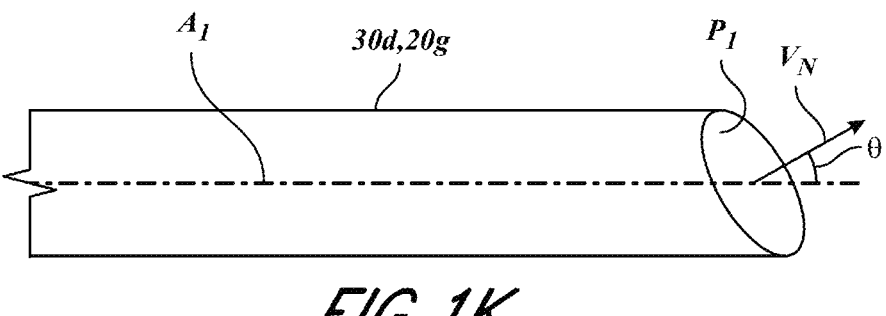
FIG. 1K illustrates an exemplary angled end of a fiber in accordance with aspects of this disclosure.

FIGS. 1I-1J illustrate enlarged views of ends of fibers 30d and fiber 20g. As shown, ends of fibers 30d and/or fiber 20g can be angled with respect to axes extending through the fibers 30d, 20g. For example, with reference to FIG. 1K, ends of fibers 30d and/or fiber 20g can be angled at an angle $\theta$ such that the normal vector $V_N$ extending perpendicular to planes $P_1$ of the ends is angled with respect to axes $A_1$ that extend through a length (or a portion of the length) of fibers 30d, 20g. Such angle $\theta$ can be any angle or range between 0 and 90 degrees. For example, angle 0 can be 5 degrees, 10 degrees, 15 degrees, 20 degrees, 25 degrees, 30 degrees, 35 degrees, 40 degrees, 45 degrees, 50 degrees, 55 degrees, or 60 degrees, or any value or range therebetween, or any range bounded by any combination of these values, although values outside these values or ranges can be used in some cases. Such angles and/or orientation of ends of fibers 30d and/or fiber 20g can advantageously allow the fibers 30d, 20g to press deeper into tissue which can in turn increase the ability for transmitted light to pass more directly through skin layers and blood vessels of the tissue (via fiber 20g) and be attenuated (to fibers 30d). The angles of ends of fibers 30d, 20g can also advantageously better align with and/or conform to surfaces of tissue of a user (for example, skin surfaces on a bottom of a user's finger) which may be angled or curved. In such cases, the angles of the ends of fibers 30d, 20g can be relatively "flush" with such angled or curved tissue surfaces, which can aid the transmission of light into the tissue via fiber 20g and can aid the collection of the attenuated light via fibers 30d. While FIGS. 1I-1J illustrate three fibers 30d having ends having similar or identical angles, each of the ends of fibers 30d can have different angles. Further, while the three fibers 30d are illustrated as being along the same vertical plane, in some embodiments, the three fibers 30d are engaged by the adapter 20e and/or portions of the sensor 10 such that the fibers 30d are not on the same vertical plane. In some embodiments, an end of fiber 20g is angled differently than one or more of the ends of the fibers 30d. Alternatively, in some embodiments, an end of fiber 20g is angled the same as one or more of the ends of the fibers 30d.

Figure 1L:
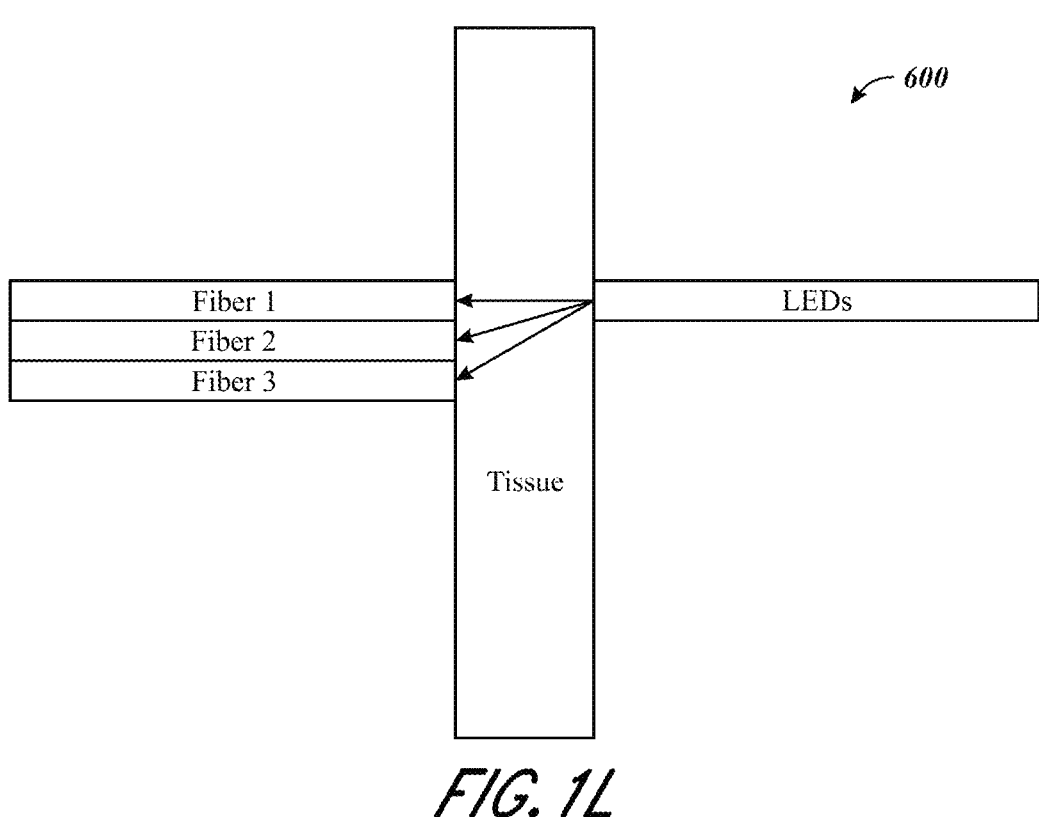
FIGS. 1L-1N illustrate exemplary schematic diagrams of embodiments of physiological measurement systems in accordance with aspects of this disclosure.
Figure 1M:
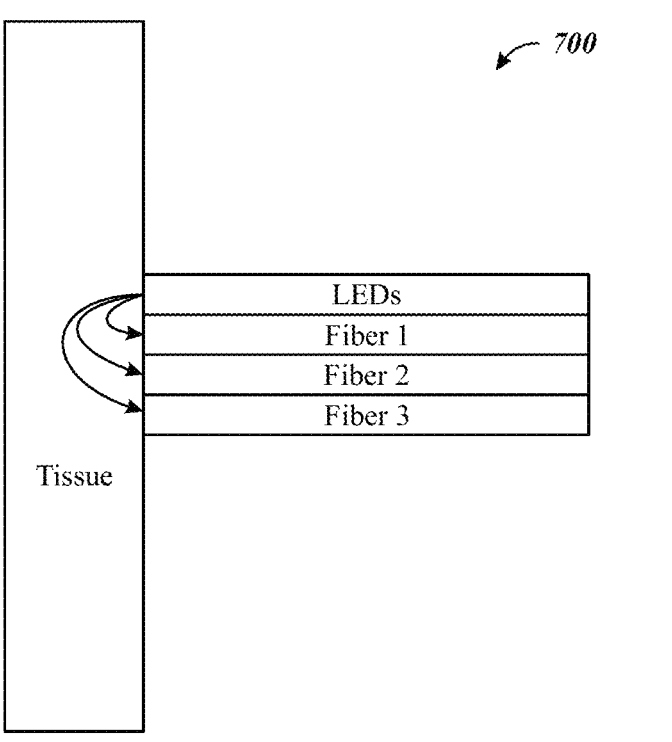
Figure 1N:
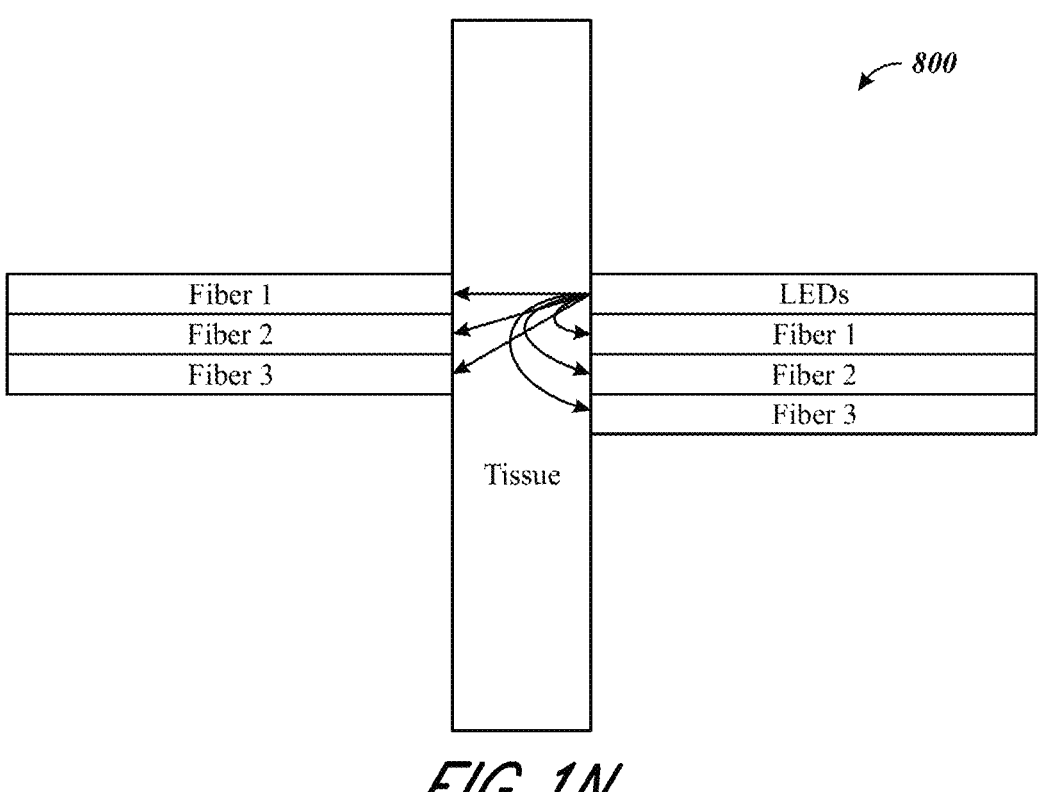
Figure 10:
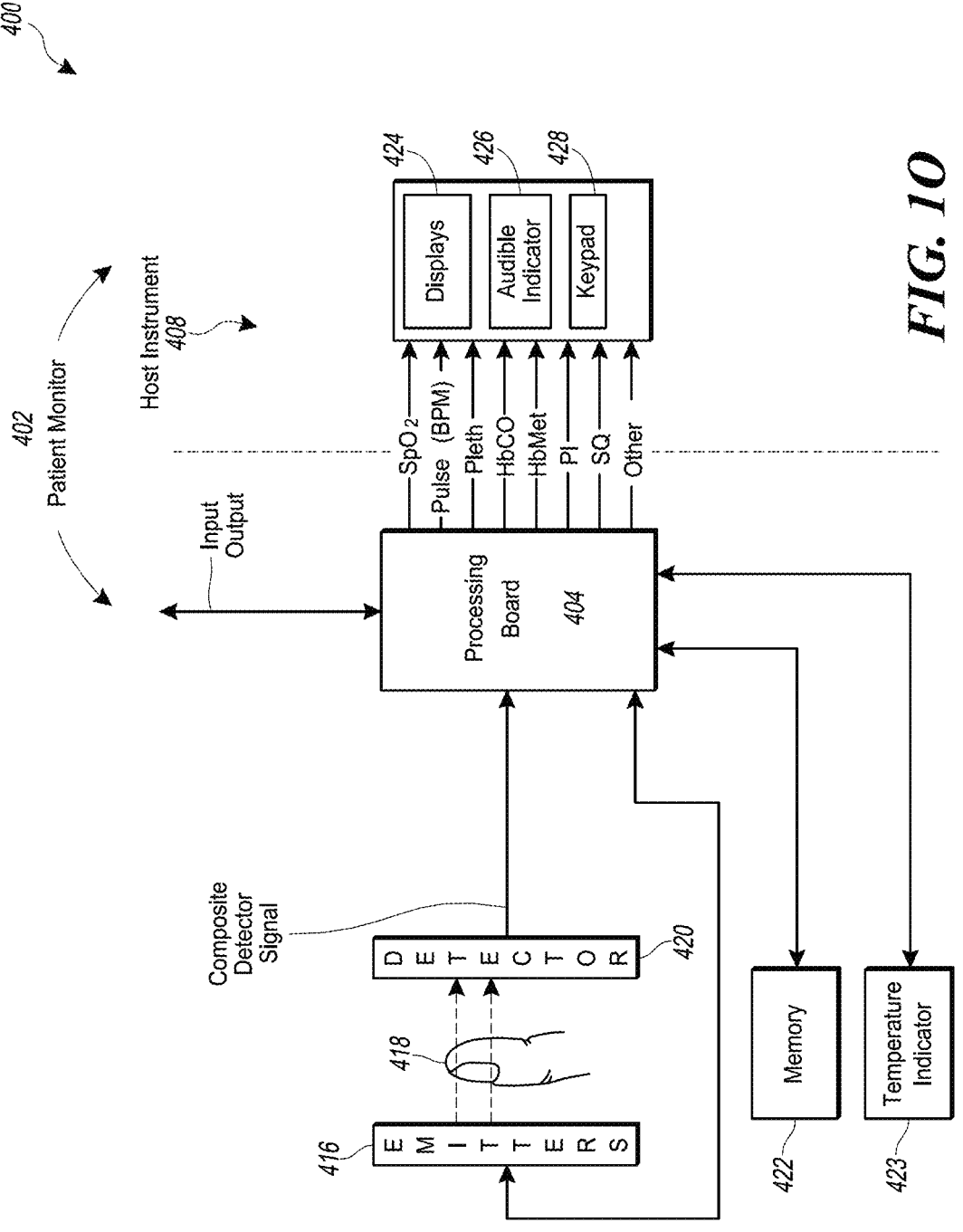

FIG. 1L illustrates a simplified schematic diagram of a physiological measurement system 600 that operates in a transmissive manner—for example, where emitters and corresponding fibers transmit light into tissue and fibers on an opposite side of the tissue collect the attenuated light. Such schematic thus illustrates aspects of the physiological measurement systems discussed elsewhere herein. FIGS. 1M-1N illustrates schematic diagrams of alternative configurations for physiological measurement systems. For example, FIG. 1M illustrates a simplified schematic diagram of a physiological measurement system 700 that operates in a reflective manner—for example, where emitters (and corresponding fibers) transmit light into tissue and fibers on the same side of the tissue collect the attenuated light. FIG. 1N illustrates a simplified schematic diagram of a physiological measurement system 800 that operates in both a transmissive and reflective manner—for example, where emitters (and corresponding fibers) transmit light into tissue and fibers on the same and the opposite side of the tissue collect the light attenuated through the tissue. Thus, while physiological measurement systems 1, 9, 500, 500' are illustrated as being configured to operate in a transmissive configuration, one of skill in the art will recognize that such systems 1, 9, 500, 500' can be modified to operate in the reflective configuration or a dual configuration (transmissive and reflective configuration), such as that shown in FIGS. 1M-1N, without departing from the scope of the present disclosure.

This disclosure describes embodiments of physiological measurement systems and noninvasive physiological measurement devices that can interact with a computing device and enable a user to measure, view, compare, analyze and/or download information relating to the respiratory system, for example, via the computing device, which may contain more advanced functionality than traditional systems and devices. The computing device can be, for instance, a cellphone or smartphone, tablet, laptop, personal digital assistant (PDA), and/or the like.

Generally, the systems and devices described herein can be used to generate information that can be incorporated into user interfaces that may be implemented in a user computing device. The user interfaces can depict displays that may be implemented in any of the user devices described herein. Such user interfaces shown may be implemented in a mobile application such as an application that runs on a mobile operating system such as the Android™ operating system available from Google™ or the iOS™ operating system available from Apple™. Alternatively, or in addition to being a mobile application, the user interfaces can be implemented in a web application that runs in a browser.

The user interfaces are merely examples that illustrate some example embodiments described herein and may be varied in other embodiments. For instance, user interface controls shown may include buttons, touch-selective components and the like which may be altered to include any type of user interface control including, but not limited to, checkboxes, radio buttons, select boxes, dropdown boxes, textboxes or any combination of the same. Likewise, the different user interface controls may be combined or their functionality may be spread apart amongst additional controls while retaining the similar or same functionality as shown and described herein. Although interfaces are shown having displays 424, audible indicator 426, and/or keypad 428, other devices may implement similar user interfaces with other types of user input devices such as a mouse, keyboard, stylus, or the like.

FIG. 1O illustrates a block diagram of an exemplary embodiment of a user monitoring system 400 that can be used alongside the physiological measurement systems 1, 9, 500, 500' and/or noninvasive physiological sensor 10. As shown, the system 400 can include a user monitor 402 including a processor 404 and a host instrument 408. As shown, the system 400 can include an emitter 416, which can be the same as the one or more emitters 2 and/or emitter package 20a, and a detector 420, which can be the same as the one or more detectors 8 and/or detector 30a. The processor 404 can receive one or more intensity signal(s) indicative of one or more parameters of tissue of a user from the detector 420. For example, with reference to FIGS. 1B, 1C, and 1G, signals from the detector(s) 30a and/or $I_o$ detector 4, 20d can be transmitted to processor 404 via cables or circuits such as flex circuits 33. The processor 404 can also communicate with a host instrument 408 to display determined values calculated using the one or more intensity signals. The processor 404 can comprise processing circuitry arranged on one or more printed circuit boards capable of installation into the monitor 402, or capable of being distributed as some or all of one or more OEM components for a wide variety of host instruments monitoring a wide variety of user information. The processor 404 can convert digital control signals into analog drive signals capable of driving emitters and can convert composite analog intensity signal(s) from light sensitive detectors into digital data. The processor 404 can process signals from the detector 420 and transmit the processed signals to, for example, host instrument 408, related to one or more intensity signals representative of the absorption or emission from transmissive or reflective sensor systems of a plurality of wavelengths of emitted light by body tissue.

As shown in FIG. 1O, the system 400 can include a plurality of emitters 416 irradiating the body tissue 418 with differing wavelengths of light, and one or more detectors 420 capable of detecting the light after attenuation by the tissue 418, as discussed above. The system 400 may include other electrical components such as, for example, a memory device 422 comprising an EPROM, EEPROM, ROM, RAM, microcontroller, combinations of the same, or the like. Other components may include an optional temperature indicator 423 or other mechanisms for, for example, determining real-time emission wavelengths of the emitters 416. These mechanisms can include, for example, the $I_o$ detector 4, 20*d* discussed above.

The host instrument 408 can receive signals indicative of the physiological parameter information calculated by the processor 404. The host instrument 408 preferably includes one or more display devices 424 capable of displaying indicia representative of the calculated physiological parameters of the tissue 418 at the measurement site. The host instrument 408 can advantageously include a handheld housing capable of displaying one or more of a pulse rate, plethysmograph data, perfusion quality such as a perfusion quality index ("PI™"), signal or measurement quality ("SQ"), values of blood constituents in body tissue, including for example, SpO2, HbCO, HbMet, HbT, or the like. The host instrument 408 can display values for one or more of HbT, Hb, blood glucose, bilirubin, or the like. The host instrument 408 may be capable of storing or displaying historical or trending data related to one or more of the measured values, combinations of the measured values, plethysmograph data, or the like. The host instrument 408 can also include an audio indicator 426 and user input device 428, such as, for example, a keypad, touch screen, pointing device, voice recognition device, or the like. The host instrument 408 can communicate with computing devices and/or physiological monitoring systems, such as physiological measurement system 1, 9, 500, 500' and/or noninvasive physiological sensor 10, over wireless or wired public or private networks. For example, such communication can be via wireless protocols such as Wi-Fi, Bluetooth, ZigBee, Z-wave, or radio frequency such as near field communication, or other wireless protocols such as cellular telephony infrared, satellite transmission, proprietary protocols, combinations of the same, and the like.

Figure 2A:
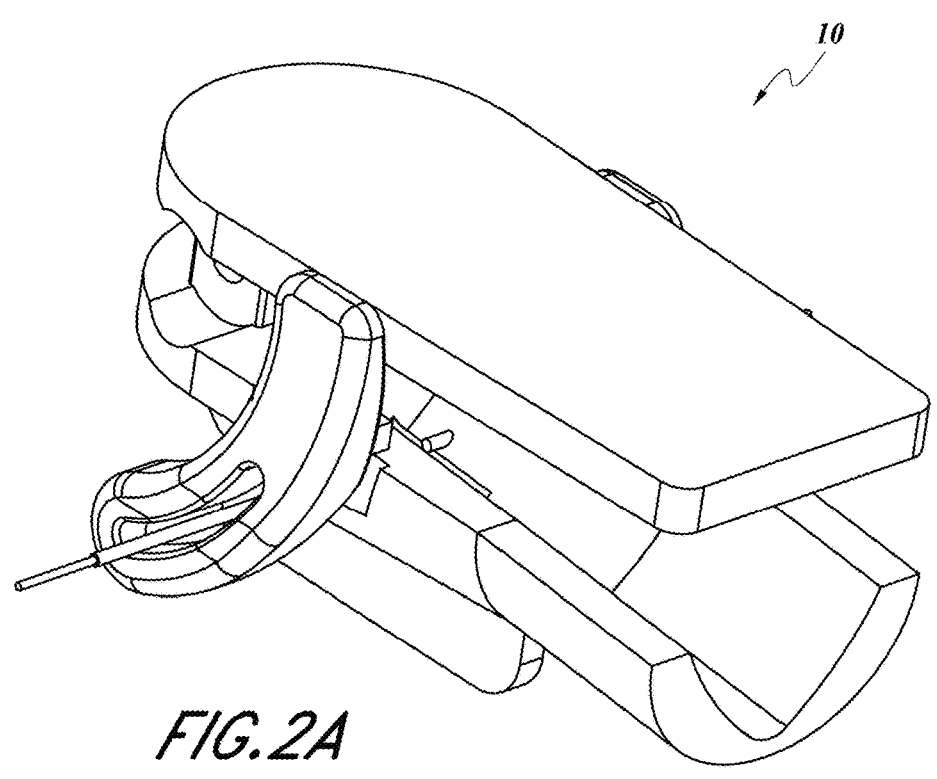
FIG. 2A illustrates a perspective view of the noninvasive physiological sensor of FIGS. 1B, 1C, and 1G.
Figure 2B:
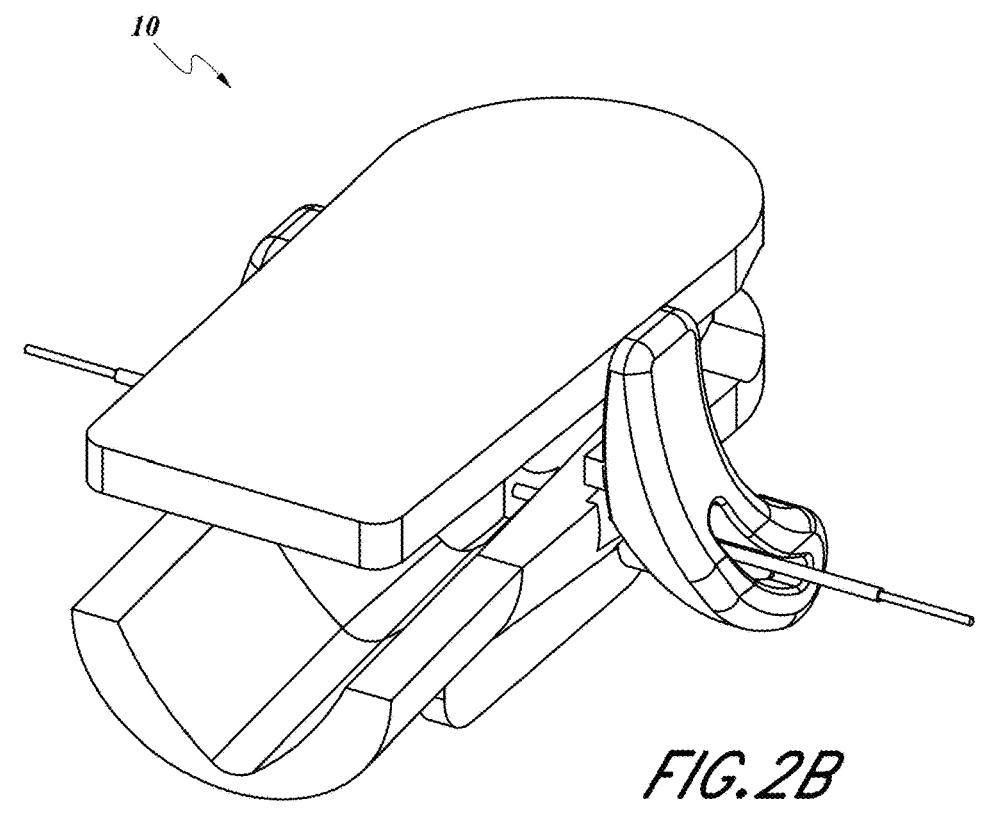
FIG. 2B illustrates another perspective view of the noninvasive physiological sensor of FIG. 2A.
Figure 2C:
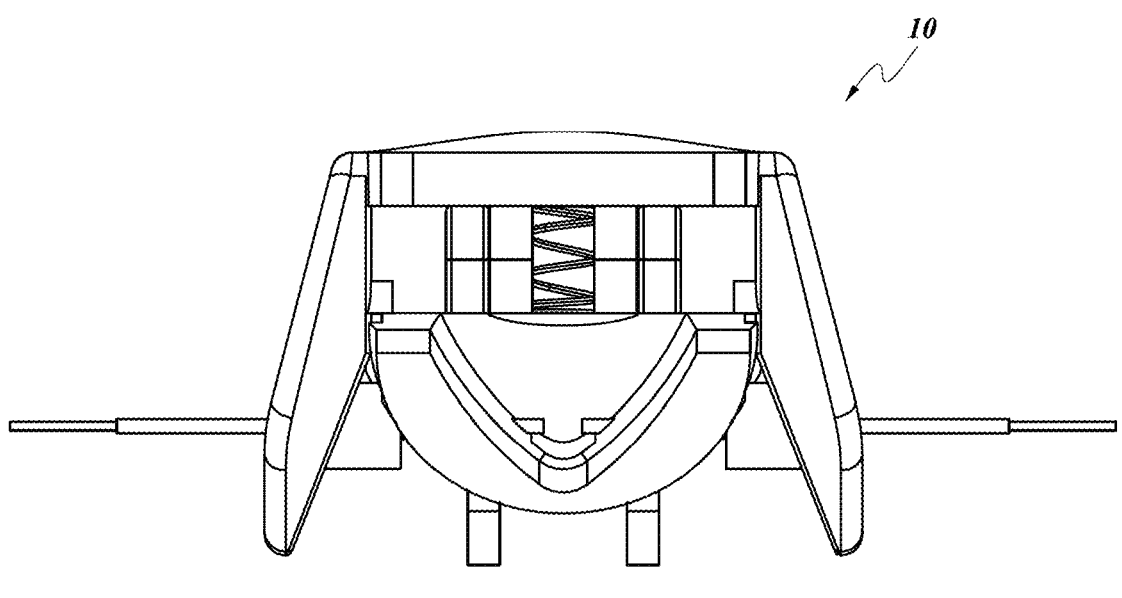
FIG. 2C illustrates a back view of the noninvasive physiological sensor of FIG. 2A.
Figure 2D:
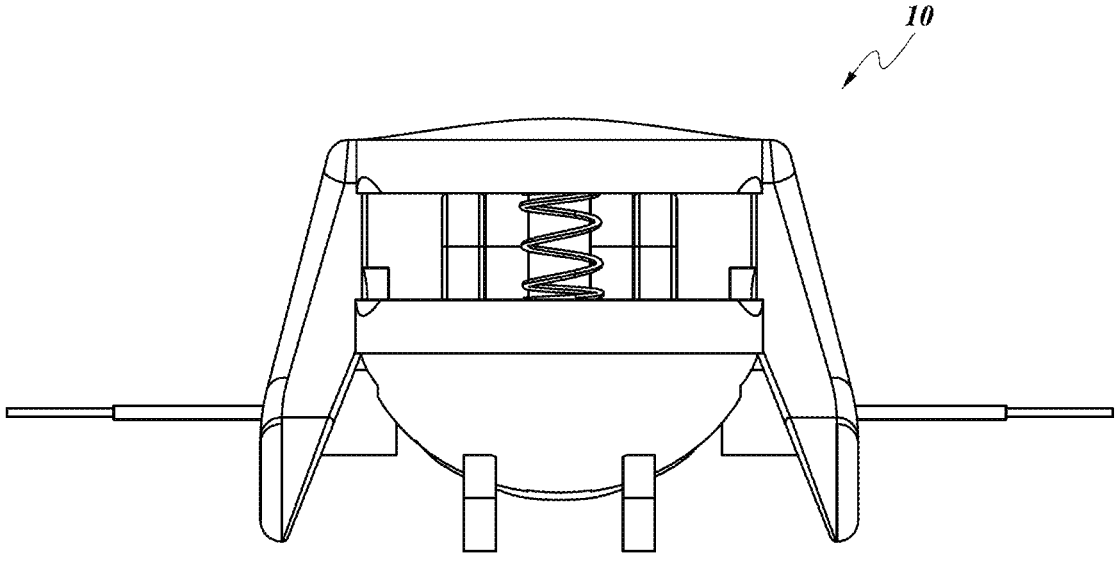
FIG. 2D illustrates a front view of the noninvasive physiological sensor of FIG. 2A.
Figure 2E:
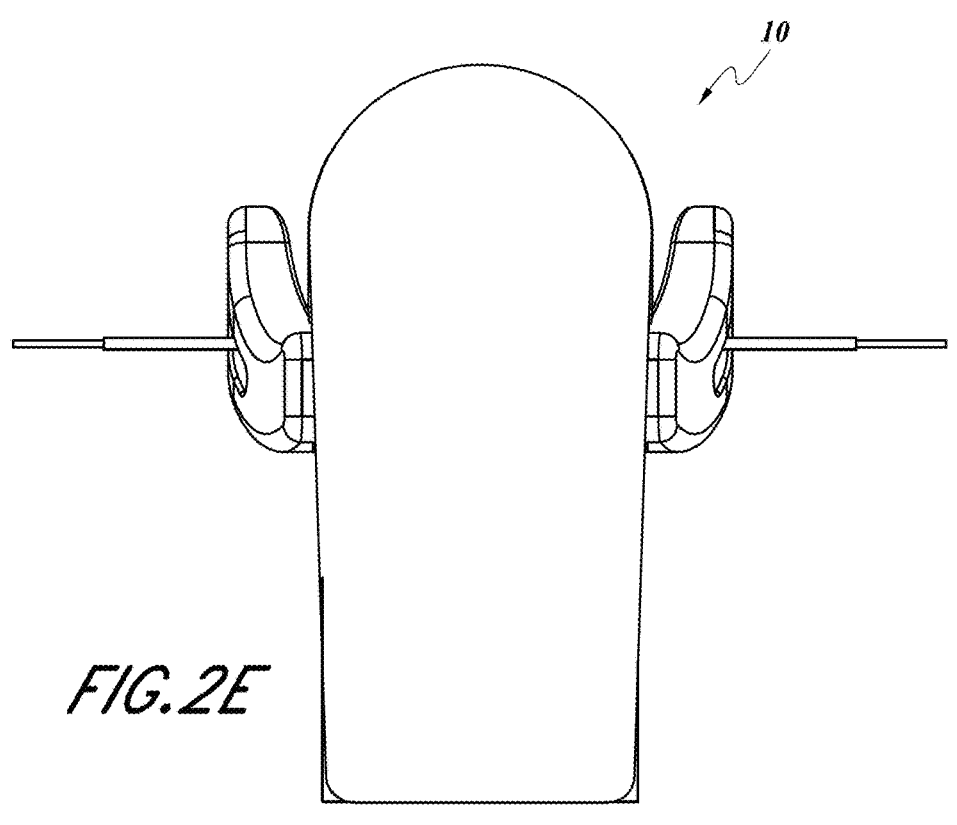
FIG. 2E illustrates a top view of the noninvasive physiological sensor of FIG. 2A.
Figure 2F:
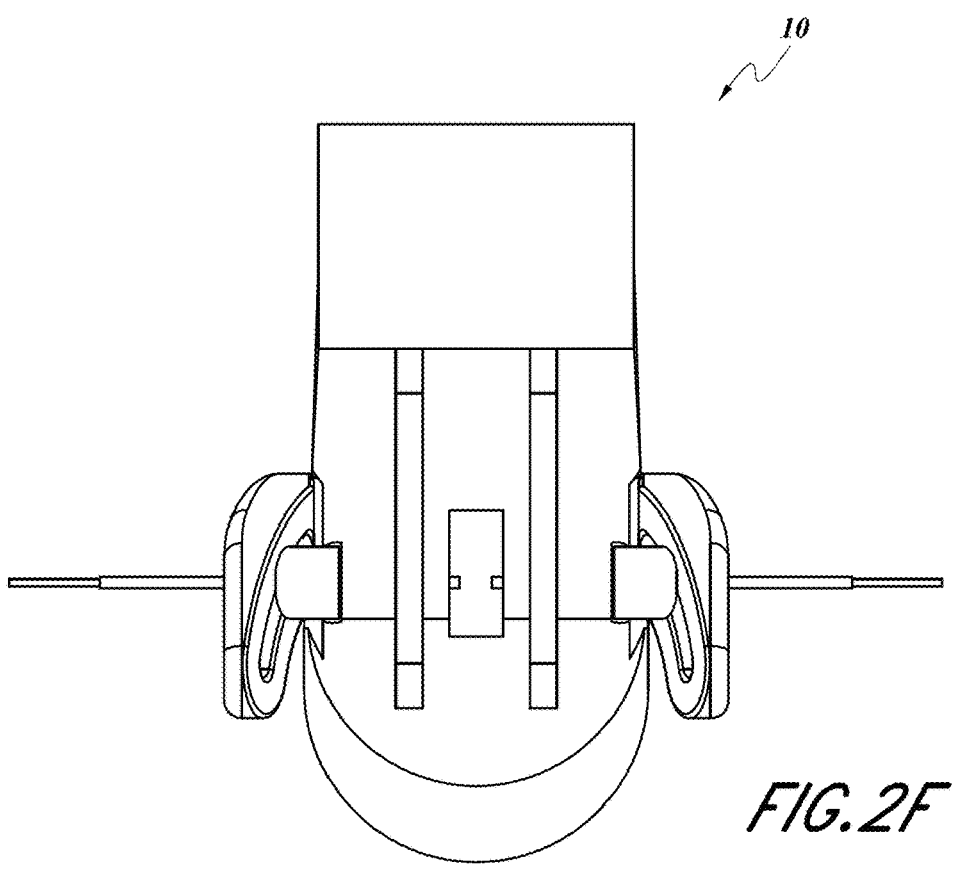
FIG. 2F illustrates a bottom view of the noninvasive physiological sensor of FIG. 2A.

FIGS. 2A-2H illustrate a noninvasive physiological sensor 10 that can be used alongside the physiological measurement systems 1, 9, 500, 500' and/or system 400 discussed above. FIGS. 3A-3B illustrate exploded perspective views of the noninvasive physiological sensor 10. Noninvasive physiological sensor 10 can include an upper sensor body 100 and a lower sensor body 200, as discussed further below. As also discussed further below, the upper sensor body 100 and the lower sensor body 200 can be coupled together via a joint, which can comprise upper sensor body hinges 114 and lower sensor body hinges 214 (see FIGS. 4C and 5B). Noninvasive physiological sensor 10 can include a biasing member 103 (FIGS. 2G-2H and 3A-3B), which can space apart the upper and lower sensor bodies 100, 200 from each other. The biasing member 103 can include a spring, rubber material, and/or a compressible material, for example. Accordingly in a closed position (for example, as illustrated in FIG. 2A), a front portion 113 of the upper sensor body 100 (see FIG. 4A) can be spaced apart from a front portion 213 of the lower sensor body 200 (see FIG. 5A). In such configuration, the front portion 113 of the upper sensor body 100 can be approximately parallel to the front portion 213 of the lower sensor body 200. Noninvasive physiological sensor 10 can include one or more probe guides configured to retain and/or secure (or at least partially retain and/or at least partially secure) one or more probes. For example, the one or more probe guides can be fiber guides 300, 300' discussed further below, such as two fiber guides, which can help secure a portion of one or more probes coupled to one or more emitters and/or one or more detectors. The one or more probes can be used to compress tissue of the user. The one or more probes can have ends which contact and/or compress the tissue of the user. The one or more probes can couple to the one or more emitters and/or one or more detectors and can help at least partially guide light from the one or more emitters to the tissue and/or can help at least partially guide attenuated light after transmission through the tissue of the user. The one or more probes can comprise, for example, fibers, such as optical fibers. For example, the one or more probes can comprise fibers 105 and/or 107 (see FIGS. 3A-3B) which can be the same in many or all respects to fibers 5*a*, 20*g*, and/or 30*d*. As shown in at least FIGS. 3A-3B and as further discussed below, fiber guides 300, 300' can fit in recesses on sides of the lower sensor body 200. As also discussed in further detail below, the fiber guides 300, 300' can have throughholes 314, 314' configured to permit the fibers 105, 107 to pass therethrough, and the fiber guides 300, 300' can fit in the recesses on the sides of the lower sensor body 200 so that the through-holes 314, 314' of the fiber guides 300, 300' align with one or more holes 230 in the lower sensor body 200 (see FIGS. 6B, 7B, and 5F). The fiber guides 300, 300' can at least partially secure the fibers 105, 107 (for example, via the through-holes 314, 314') and/or align the fibers 105, 107 so that they can pass through the one or more holes 230 of the lower sensor body 200. While the figures illustrate recessed portions on the sides of the lower sensor body 200 that are sized and/or shaped to receive a portion of the fiber guides 300, 300' (for example, recessed portions 250 as shown in FIGS. 5A and 5B), the upper sensor body 100 can additionally and/or alternatively include recessed portions on sides thereof which are configured to receive at least a portion of fiber guides 300, 300'.

Noninvasive physiological sensor 10 can be secured to a finger 11 of a user. FIG. 2I illustrates noninvasive physiological sensor 10 with the upper sensor body 100 removed so as to better show the finger 11 when positioned within the noninvasive physiological sensor 10. As discussed further below, the noninvasive physiological sensor 10 (or a portion thereof) can be shaped to conform to the shape of a portion of a user's body. For example, the lower sensor body 200 (or a portion thereof) can be shaped to conform to a finger 11 of the user. As another example, the lower sensor body 200 (or a portion thereof) can be shaped to conform to a skin-side surface of finger 11 of the user. FIGS. 2J-2K illustrate a bottom view of the noninvasive physiological sensor 10 where a finger 11 is shown in phantom lines. FIG. 2J illustrates the noninvasive physiological sensor 10 in an open position and FIG. 2K illustrates the noninvasive physiological sensor 10 in a closed position. As can be seen in FIG. 2K and as is discussed further below, the noninvasive physiological sensor 10 can be configured to move the fibers 105, 107 towards each other within an interior space defined by the noninvasive physiological sensor 10 so that a portion of the user's finger 11 is compressed. As discussed further herein, such compression allows light to be transmitted through and attenuated by a portion of the user's tissue and detected without having to pass through a user's bone. As discussed elsewhere herein, such compression also allows the fibers 105, 107 to more directly transmit light through, and collect attenuated light from, deeper region so the tissue which include the user's blood vessels. This can advantageously increase the accuracy of physiological measurements which rely on transmitting light through such blood vessels.

Figure 4A:
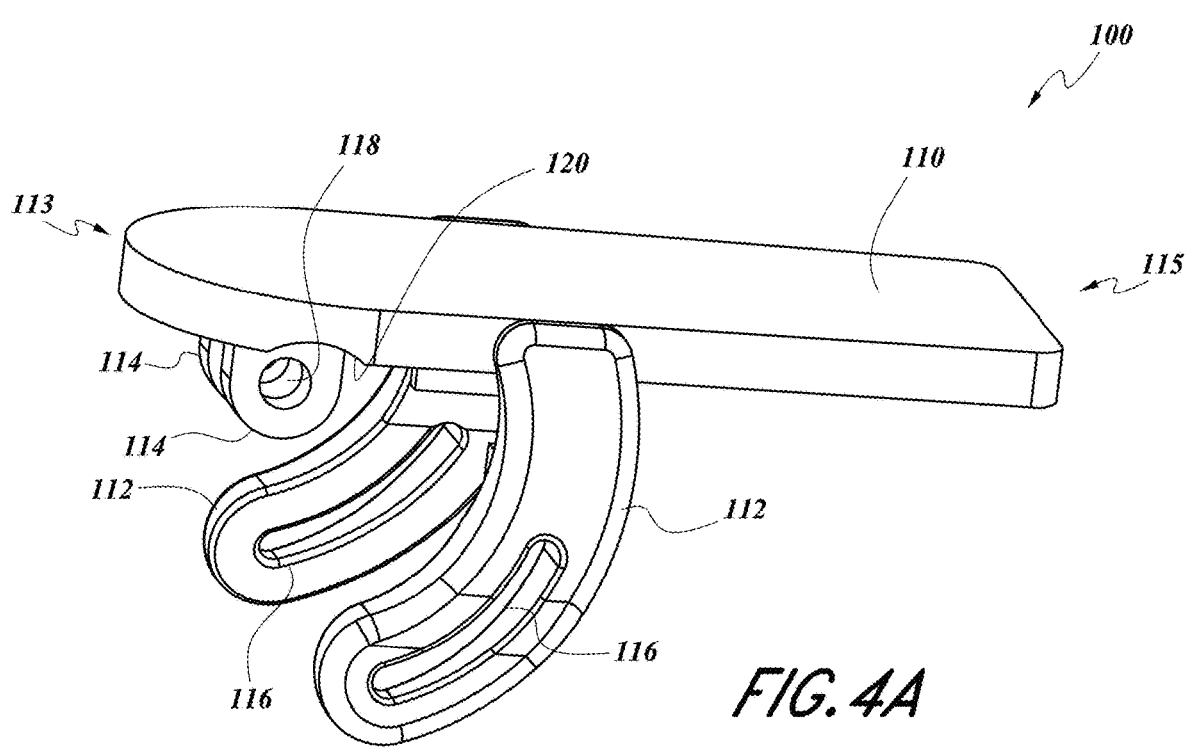
FIG. 4A illustrates a perspective view of an upper sensor body of the noninvasive physiological sensor of FIG. 2A.
Figure 4B:
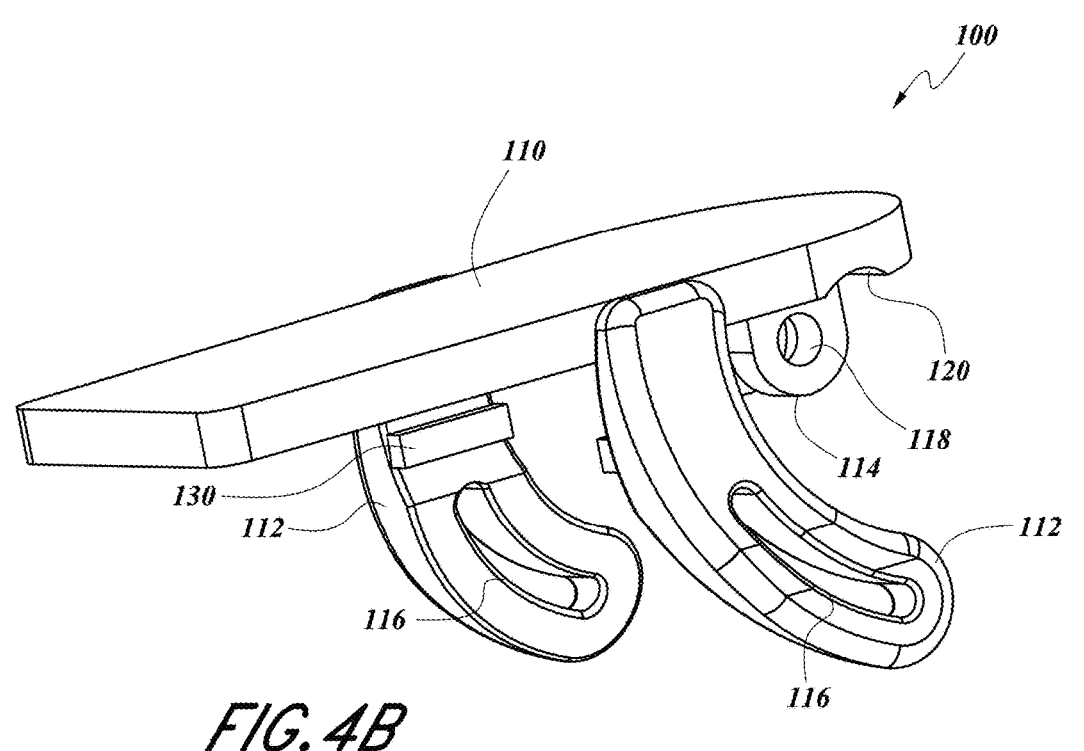
FIG. 4B illustrates another perspective view of the upper sensor body of FIG. 4A.

FIGS. 4A-4I illustrates various views of the upper sensor body 100 of the noninvasive physiological sensor 10. Upper sensor body 100 can include a top surface 110 (see FIGS. 4A-4B) and a bottom surface 111 opposite to the top surface 110 (see FIG. 4C). Upper sensor body 100 can also include a front portion 113 and a back portion 115 (see FIG. 4A). The front portion 113 can be shaped to correspond to the shape of a front portion of the lower sensor body 200 (such as front portion 213). The front portion 113 can be curved and/or rounded, as shown in FIG. 4A.

As described and shown herein, the noninvasive physiological sensor 10 can include a joint configured to rotatably couple the upper sensor body 100 to the lower sensor body 200 and allow the upper sensor body 100 and/or the lower sensor body 200 to rotate with respect to each other. As shown by FIG. 2L, the joint can allow the upper sensor body 100 and/or the lower sensor body 200 to rotate about a transverse axis 52 of the noninvasive physiological sensor 10, which can be perpendicular to a longitudinal axis 50 that extends through a length of the noninvasive physiological sensor 10. The joint can include a first coupling portion that extends from the upper sensor body 100 and a second coupling portion that extends from the lower sensor body 200, whereby the first and second coupling portions couple to each other and allow the upper and lower sensor bodies 100, 200 to be rotatably coupled to one another. For example, the first coupling portion can include one or more hinges 114 (see FIGS. 4A-4E), such as one, two, three, or four or more hinges 114. The first coupling portion can include two hinges 114 that extend from bottom surface 111 of the upper sensor body 100. The hinges 114 can extend from the bottom surface 111 in a direction generally perpendicular to the bottom surface 111. As discussed and shown herein, the hinges 114 can extend from the bottom surface 111 of the upper sensor body 100 towards the lower sensor body 200 when the noninvasive physiological sensor 10 is assembled.

The first coupling portion of the upper sensor body 100 can be sized and/or shaped to fit within a recessed portion of the lower sensor body 200 so as to facilitate rotation of the upper sensor body 100 with respect to the lower sensor body 200. For example, extending or "free" ends of the hinges 114 can be curved and/or rounded so as to fit at least partially within a curved recessed portion 220 on the lower sensor body 200 (see FIGS. 4C and 5A-5B). When the upper sensor body 100 rotates relative to the lower sensor body 200, the corresponding shape of the hinges 114 and the recessed portions 220 can facilitate smooth rotation of the upper sensor body 100 with respect to the lower sensor body 200 with little or no interference from the hinges 114. In a similar fashion, upper sensor body 100 can include a recessed portion 120 that is sized and/or shaped to correspond to the size and/or shape of the second coupling portion extending from the lower sensor body 200 so as to facilitate rotation of the lower sensor body 200 with respect to the upper sensor body 100. For example, the bottom surface 111 of the upper sensor body 100 can have a curved recessed portion 120 that corresponds to a curved and/or rounded shape of hinges 214 of the second coupling portion of the lower sensor body 200. When the lower sensor body 200 rotates relative to the upper sensor body 100, the corresponding shape of the hinges 214 and the recessed portions 120 can facilitate smooth rotation of the lower sensor body 200 with respect to the upper sensor body 100 with little or no interference from the hinges 214. The recessed portions 120, 220 can thus facilitate smooth rotation of hinges 114, 214 and also allow the device 10 to be compact in size. For example, the device 10 can have less vertical height than would otherwise be needed to accommodate spacing and/or rotation of the hinges 114, 214 proximate to the upper and lower sensor bodies 100, 200.

The one or more hinges 114, 214 can include one or more holes 118, 218 extending therethrough sized and/or shaped to allow a pin (not shown) to pass therethrough. The pin can extend through holes 118 of the hinges 114 and also extend through holes 218 on hinges 214 so as to secure and/or couple the hinges 114 to the hinges 214. When the joint of the noninvasive physiological sensor 10 is assembled, hinges 114 can be adjacent to hinges 214 and can be positioned in between hinges 214 (compare, for example, FIG. 4G and FIG. 5D). Alternatively, when the joint is assembled, hinges 214 can be adjacent to hinges 114 and can lay in between hinges 114. In some embodiments, upper sensor body 100 has one hinge 114. Alternatively, in some embodiments, upper sensor body 100 has two or more hinges 114. In some embodiments, lower sensor body 200 has one hinge 214. Alternatively, in some embodiments, lower sensor body 200 has two or more hinges 214.

As shown in at least FIGS. 2G-2H and 3A-3B, the noninvasive physiological sensor 10 can include a biasing member 103. Biasing member 103 can include a compression spring, among other materials described herein. Where the biasing member 103 comprises a compression spring, the spring can comprise various strength and/or stiffness properties, and/or other material properties.

Figure 4C:
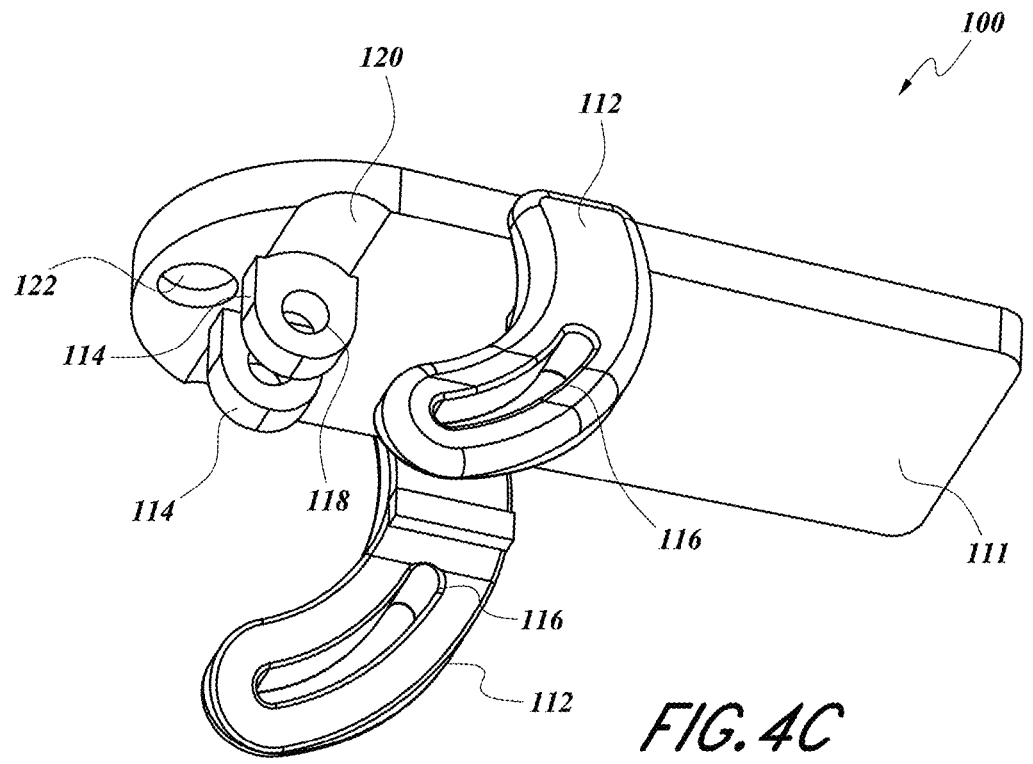
FIG. 4C illustrates another perspective view of the upper sensor body of FIG. 4A.
Figure 4D:
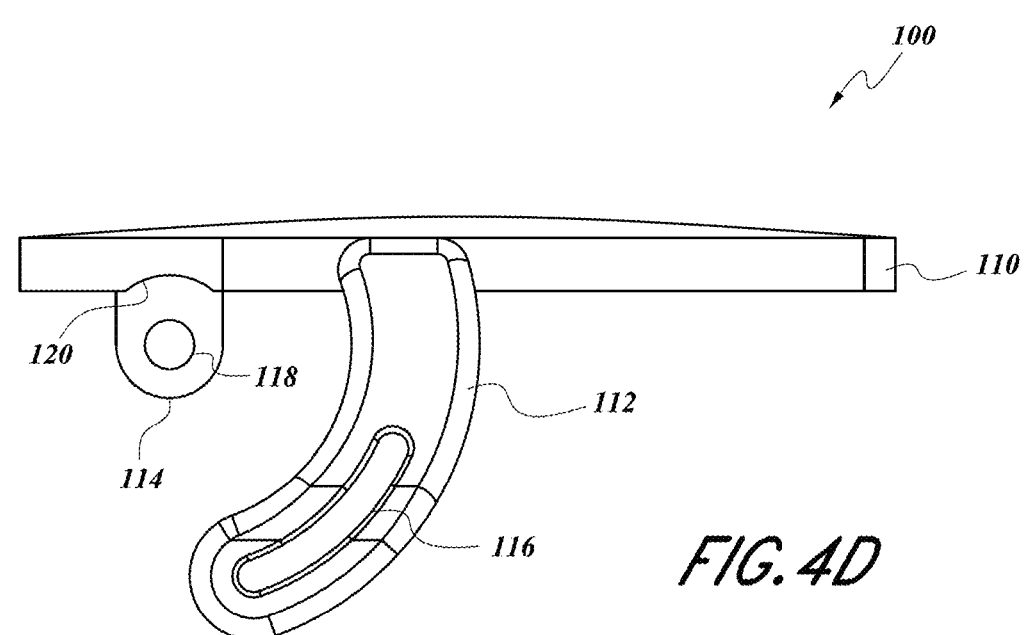
FIG. 4D-4E illustrate side views of the upper sensor body of FIG. 4A.
Figure 4E:
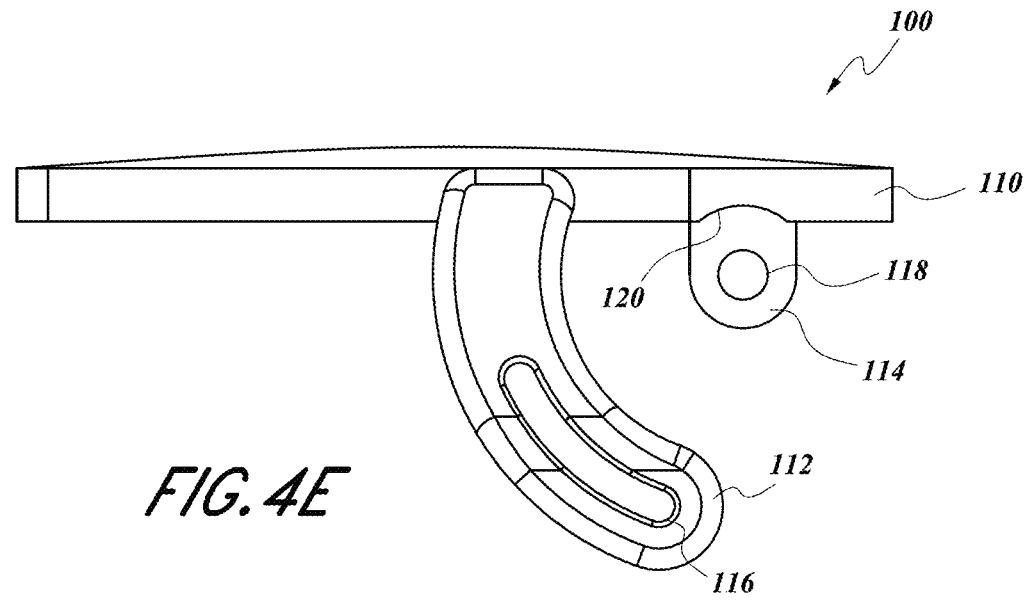
Figure 4F:
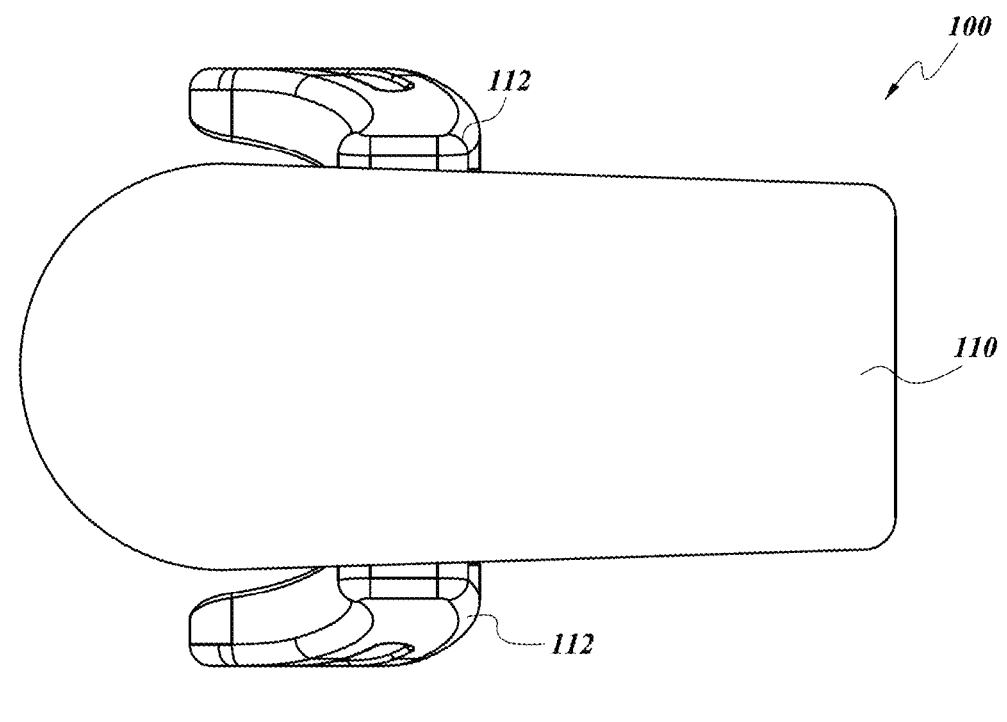
FIG. 4F illustrates a top view of the upper sensor body of FIG. 4A.
Figure 4G:
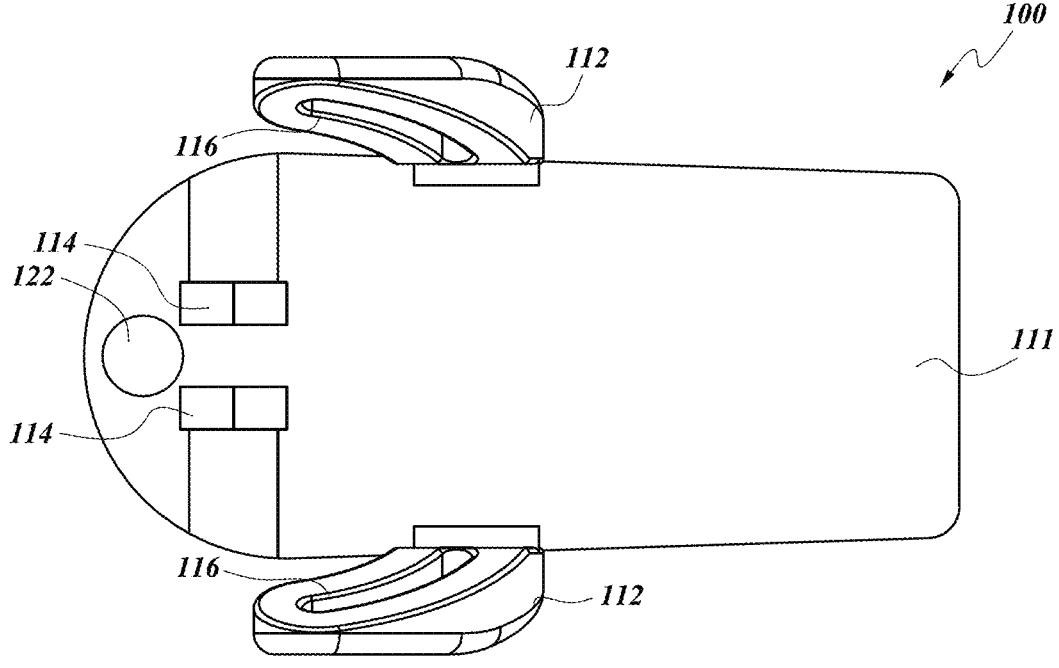
FIG. 4G illustrates a bottom view of the upper sensor body of FIG. 4A.
Figure 5A:
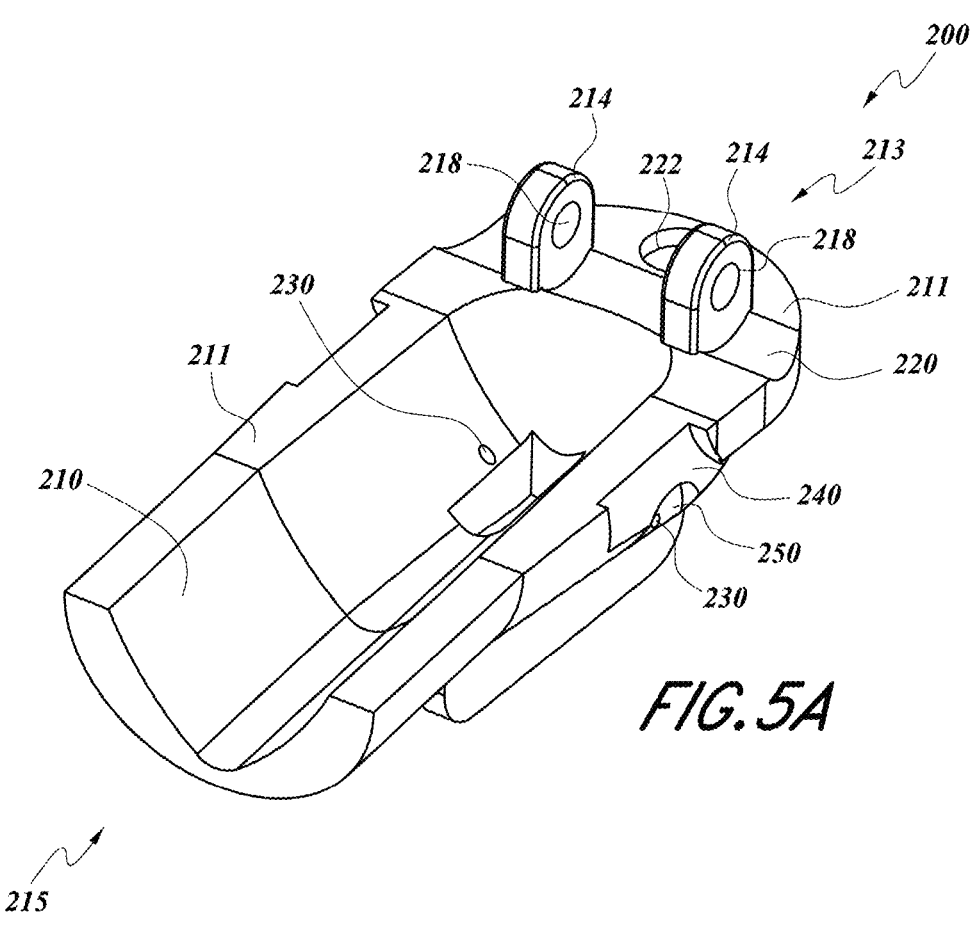
FIG. 5A illustrates a top perspective view of a lower sensor body of the noninvasive physiological sensor FIG. 2A.
Figure 5B:
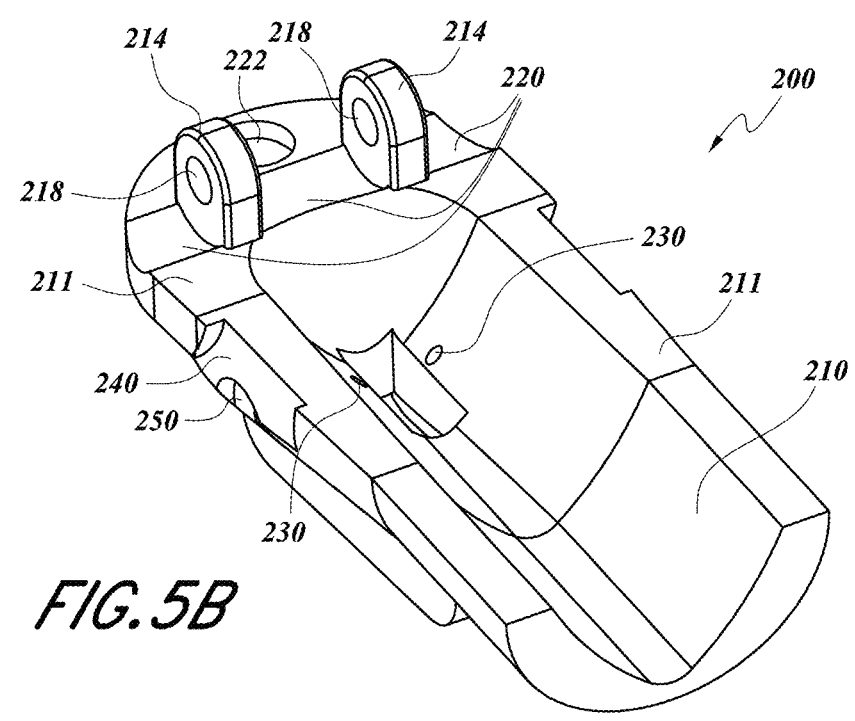
FIG. 5B illustrates another top perspective view of the lower sensor body of FIG. 5A.

Biasing member 103 can be in contact with or be coupled to the upper sensor body 100 and/or the lower sensor body 200. For example, the upper sensor body 100 can include a protrusion and/or recess for receiving one end of the biasing member 103. For example, as shown in FIGS. 4C and 4G, upper sensor body 100 can include a recess 122 on bottom surface 111 that is sized and/or shaped to receive an end of the biasing member 103. Recess 122 can be, for example, a cylindrical recess (see FIG. 4C). The upper sensor body 100 can additionally or alternatively include a skirt wall extending around a perimeter of a portion of the bottom surface 111 of the upper sensor body 100 which can help secure and/or align the biasing member 103 or a portion thereof. Biasing member 103 can be adhered to the bottom surface 111 of the upper sensor body 100. Biasing member 103 can space the upper sensor body 100 from the lower sensor body 200. The lower sensor body 200 can include a protrusion (not shown) and/or recess for receiving one end of the biasing member 103. For example, as shown in at least FIGS. 5A-5B, lower sensor body 200 can include a recess 222 on top surface 211 of the lower sensor body 200 that is sized and/or shaped to receive an end of the biasing member 103. Recess 222 can be, for example, a cylindrical recess 222 (see FIGS. 5A-5B). The lower sensor body 200 can additionally or alternatively include a skirt wall extending around a perimeter of a portion of the top surface 211 of the lower sensor body 200 which can help secure and/or align the biasing member 103. Biasing member 103 can be adhered to the top surface 211 of the lower sensor body 200. Biasing member 103 can be adhered to the top surface 211 of the lower sensor body 200 and the bottom surface 111 of the upper sensor body 100.

Biasing member 103 can be positioned at an approximate center of a width of the noninvasive physiological sensor 10 along transverse axis 52 (see FIG. 2L). Such positioning can advantageously allow the upper sensor body 100 and/or the lower sensor body 200 to be properly balanced and/or positioned when rotated relative to one another and can also ensure that there is a symmetric restoring force to appropriately bias the noninvasive physiological sensor 10.

Figure 2G:
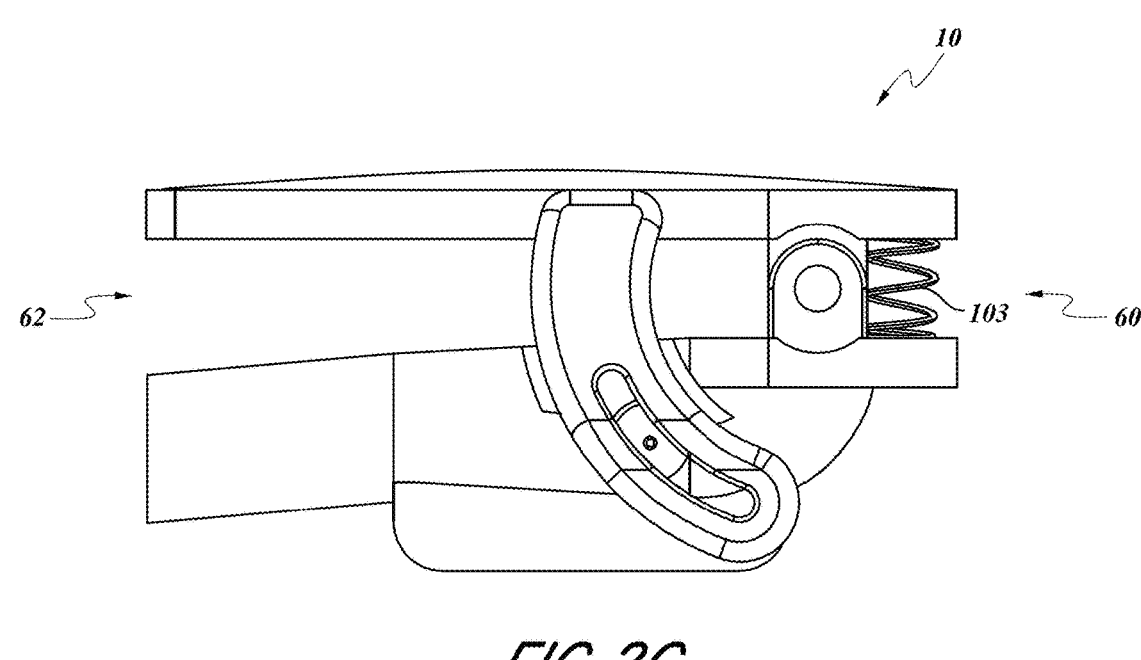
FIG. 2G illustrates a side view of the noninvasive physiological sensor of FIG. 2A.
Figure 2H:
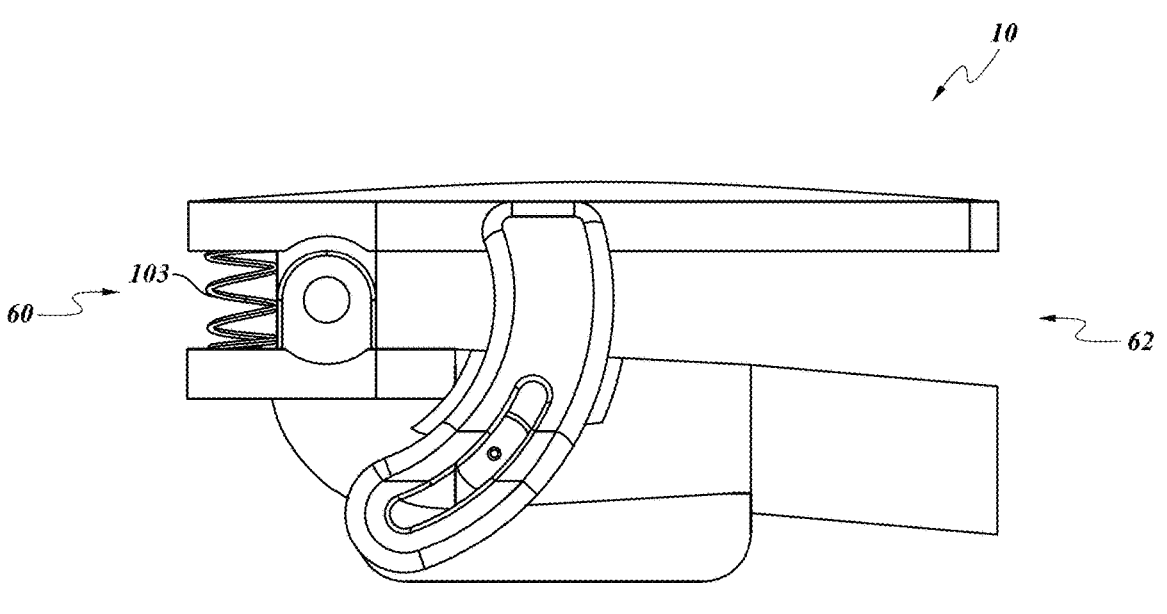
FIG. 2H illustrates another side view of the noninvasive physiological sensor of FIG. 2A.
Figure 21:
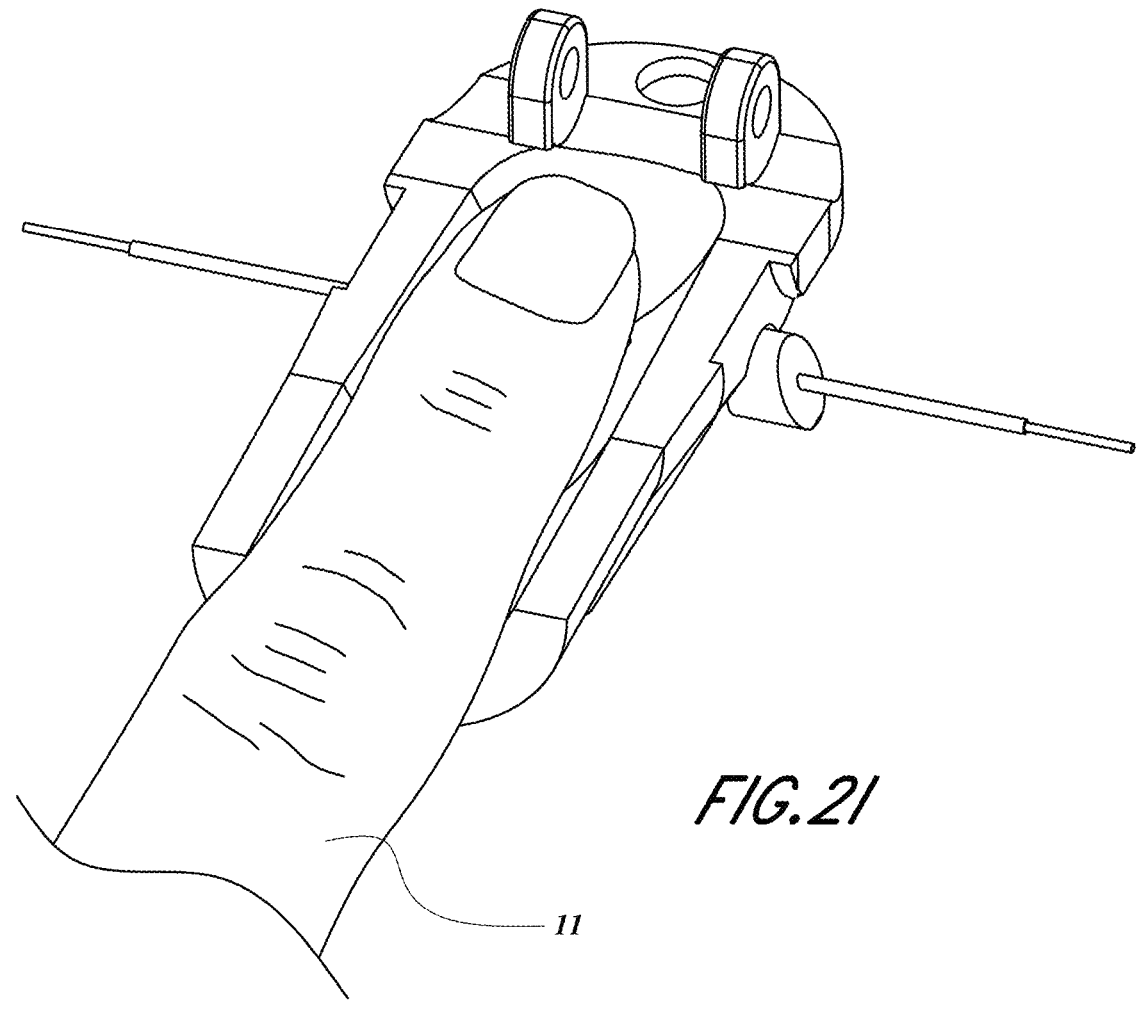
Figures 2J, 2K:
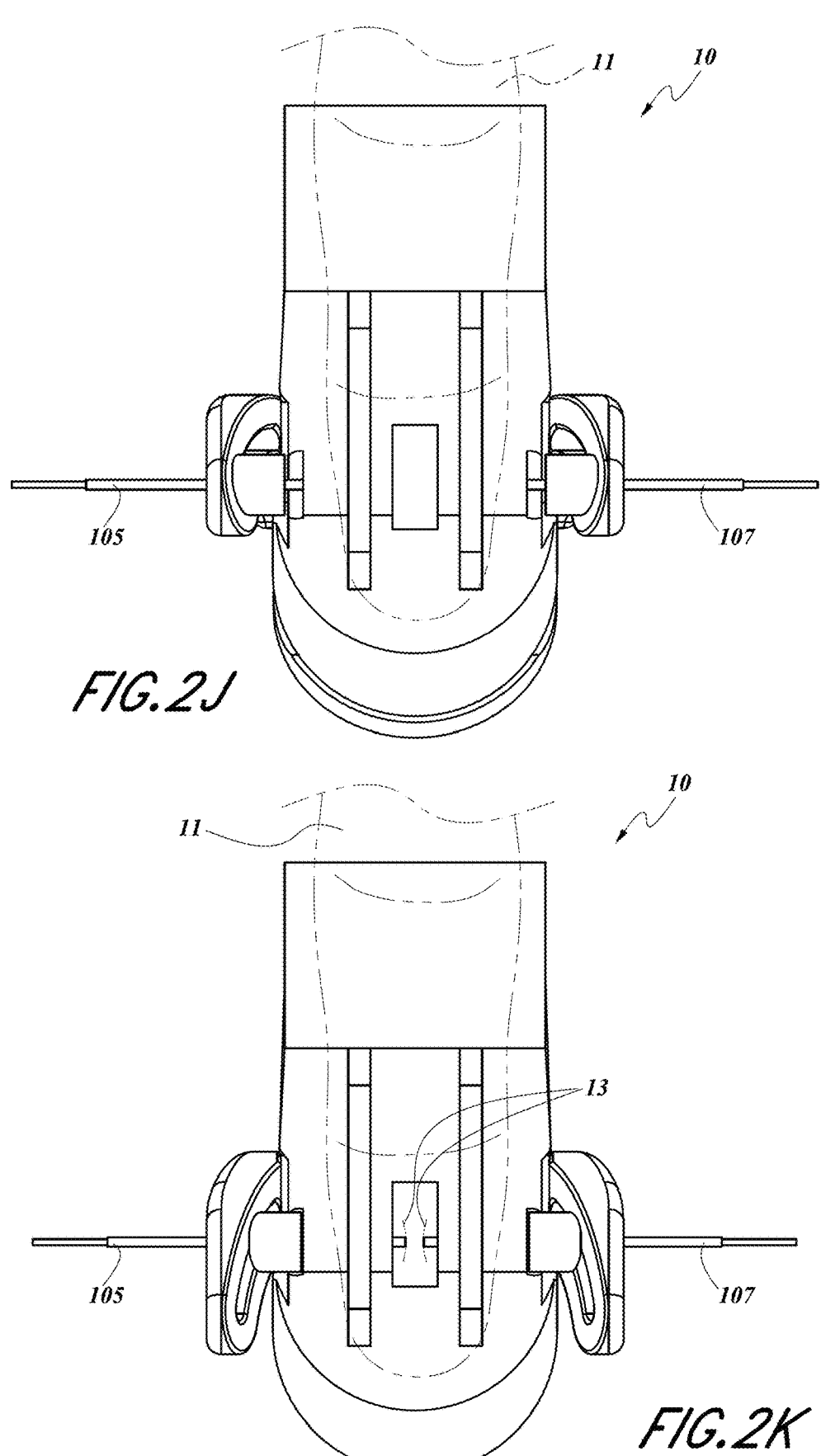
FIG. 2J illustrates a bottom view of the noninvasive physiological sensor of FIG. 2A in an open configuration with a finger positioned therewithin.
FIG. 2K illustrates a bottom view of the noninvasive physiological sensor of FIG. 2A in a closed configuration where a finger positioned therewithin and tissue of the user is compressed by fibers in accordance with aspects of this disclosure.
Figure 2L:
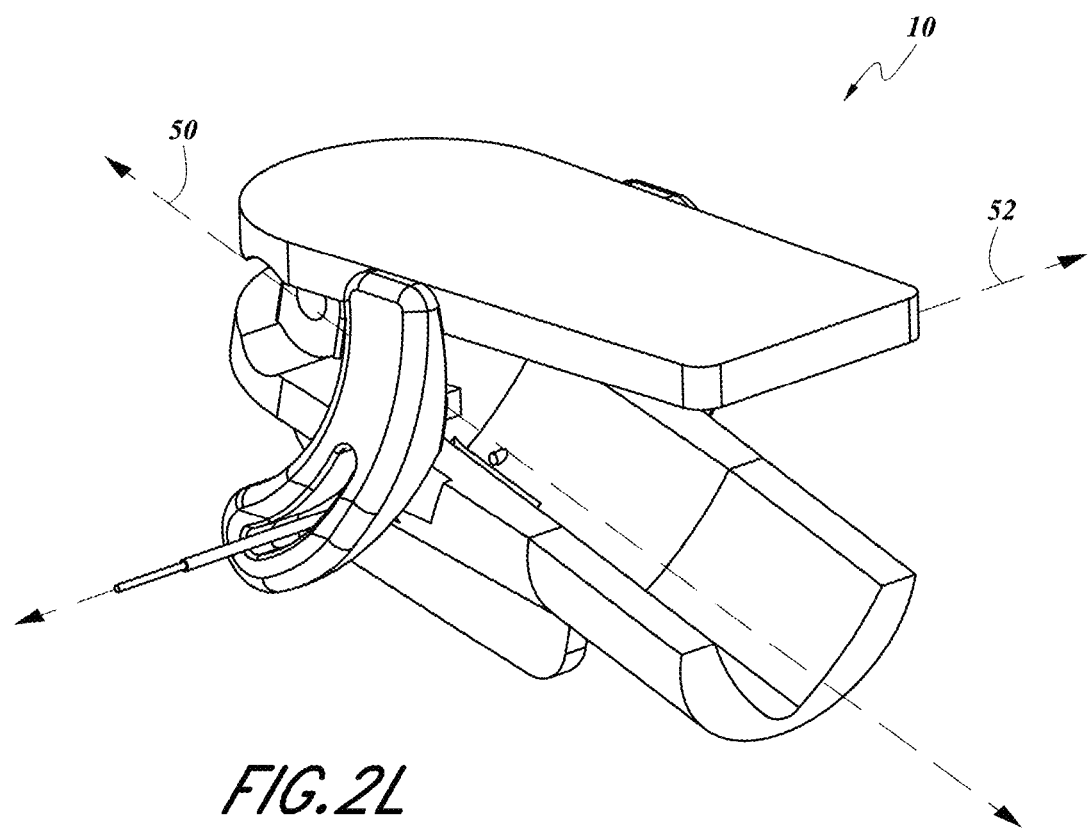
FIG. 2L illustrates another perspective view of the noninvasive physiological sensor of FIG. 2A showing longitudinal and transverse axes of the device.
Figure 3A:
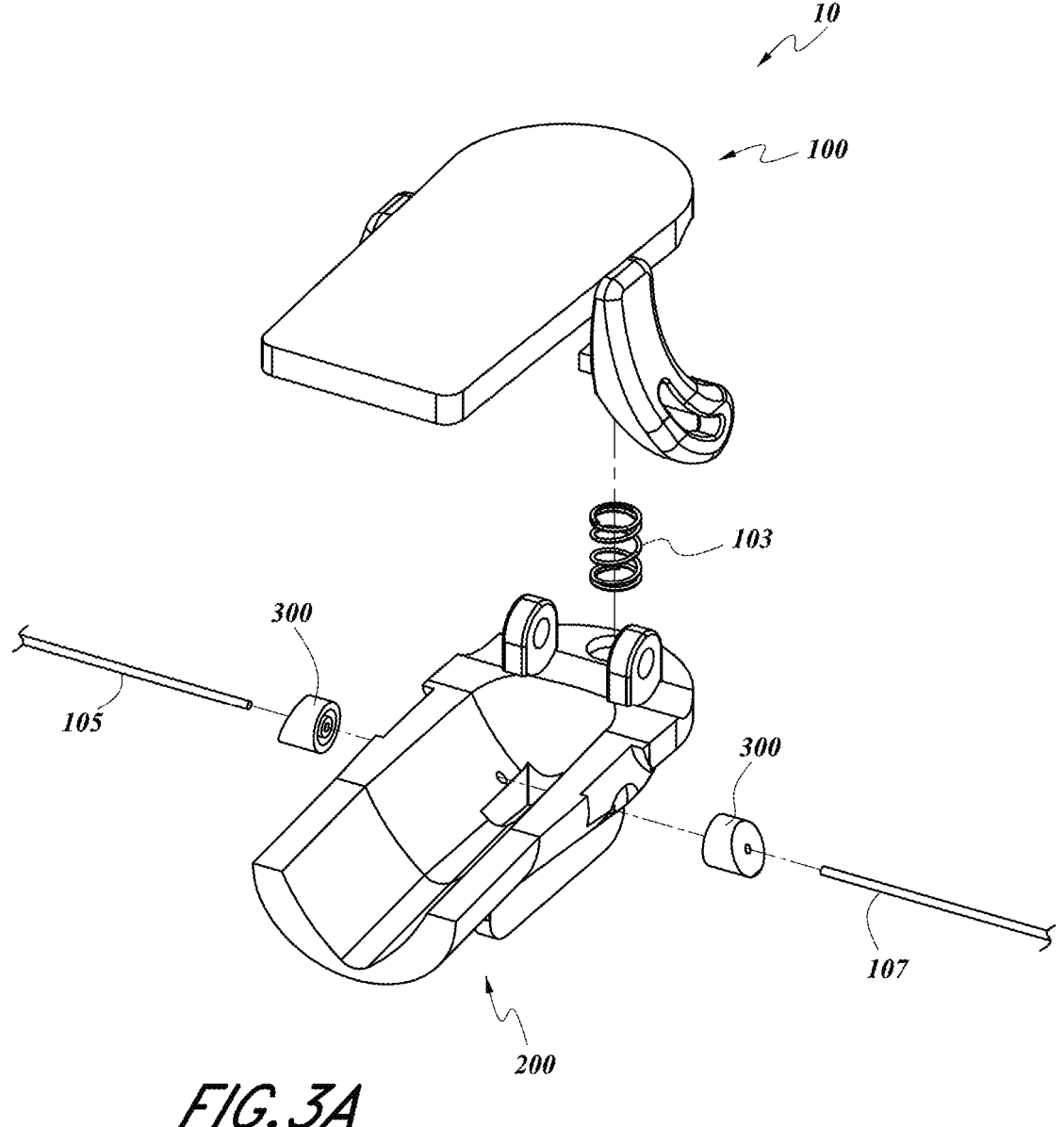
FIG. 3A-3B illustrate exploded views of the noninvasive physiological sensor of FIG. 2A.
Figure 3B:
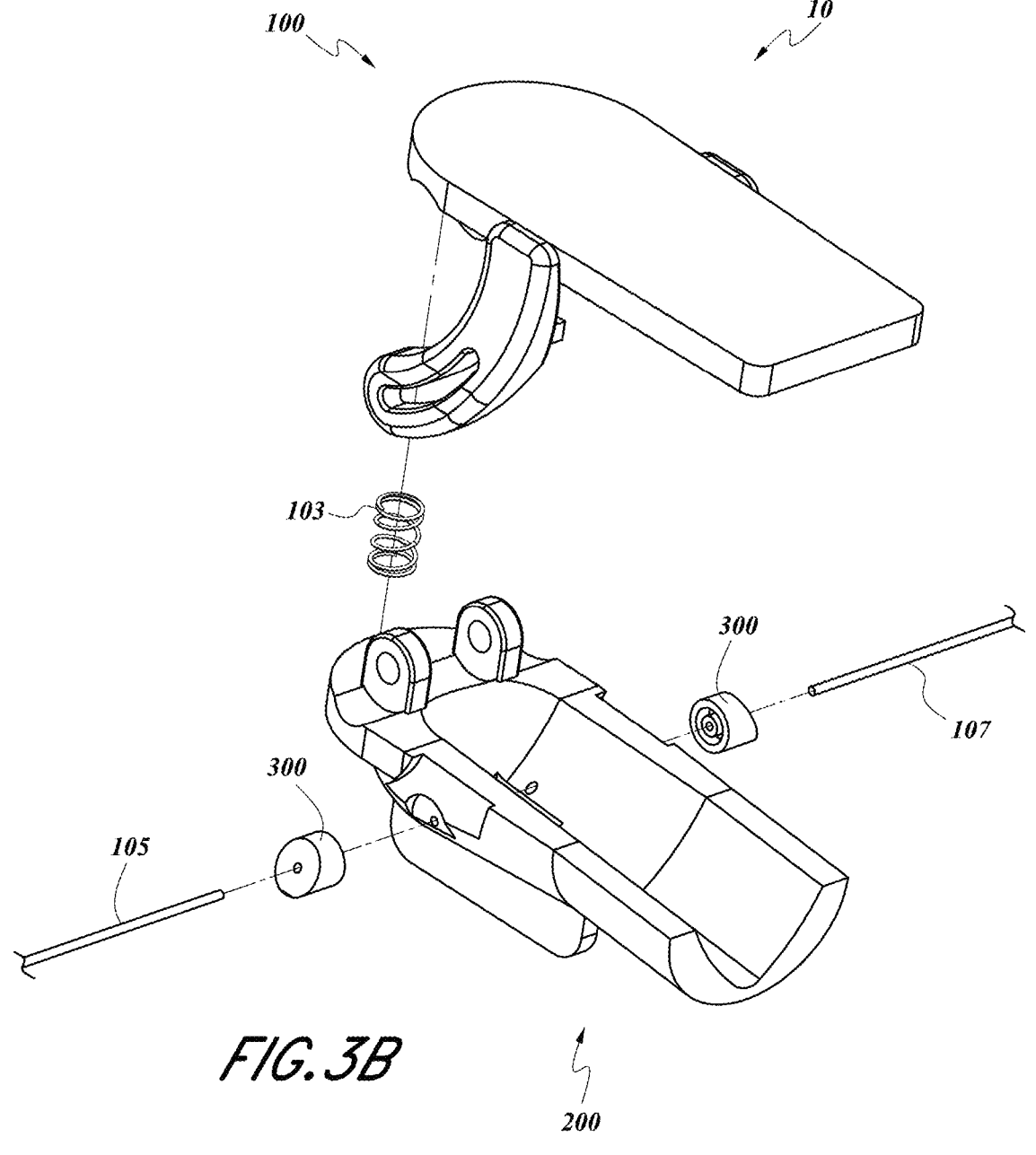

FIGS. 2G-2H illustrate side views of the noninvasive physiological sensor 10 including biasing member 103 at a front portion 60 of the noninvasive physiological sensor 10. The front portion 60 of the noninvasive physiological sensor 10 can rotate about the pin extending through each of the first and second coupling portions of the upper and lower sensor bodies 100, 200 discussed above.

When no or minimal external forces are applied to the noninvasive physiological sensor 10, biasing member 103 can be not compressed or not expanded and/or can be minimally compressed and/or minimally expanded. As shown in FIGS. 2G-2H, 4A, and 5A, in a closed position, a back portion 115 of the upper sensor body 100 can be spaced apart from a back portion 215 of the lower sensor body 200.

When a force is applied to biasing member 103, such as when an external force is applied to the noninvasive physiological sensor 10 which can be a clip-type arrangement, biasing member 103 can allow the upper sensor body 100 to rotate about the pin relative to the lower sensor body 200 and/or the lower sensor body 200 to rotate about the pin relative to the upper sensor body 100. The biasing member 103 can bias the upper sensor body 100 and/or the lower sensor body 200 in a position, in which no and/or minimal external forces are applied. The biasing member 103 can also help close and/or secure the sensor 10 to a user's finger, for example. Thus, the biasing member 103 can allow the noninvasive physiological sensor 10 to comfortably be secured to a user, such as on a finger of a user.

Biasing member 103 can be coupled near the front portion 113, 213 of the upper sensor body 100 and the lower sensor body 200. For example, biasing member 103 can be fit within recesses 122, 222 of the upper and lower sensor bodies 100, 200 near a perimeter edge of the front portions 113, 213. Thus, the biasing member 103 can space the upper sensor body 100 from the lower sensor body 200. As shown in at least FIG. 2L, for example, this can allow a greater range of rotation about the joint. Such configurations can allow for the noninvasive physiological sensor 10 to accommodate a greater variety of shapes and sizes of, for example, fingers of users.

As discussed herein, noninvasive physiological sensor 10 can include fiber guides 300, 300' that secure and/or align fibers 105, 107 and that can fit within recessed portions 250 (see FIGS. 5A-5B) along sides of lower sensor body 200. As also discussed herein, the fibers 105, 107 can be configured to pass through through-holes 314, 314' in fiber guides 300, 300' and pass through holes 230 in the lower sensor body 200 into an interior space defined by the lower sensor body 200. The interior space defined by the lower sensor body 200 can be, for example, a volume defined by the lower sensor body 200 that is sized and/or shaped to conform to a portion of a finger of a user. The fiber guides 300, 300' can be configured such that they move and/or compress when engaged by a swivel mechanism of the noninvasive physiological sensor 10. The swivel mechanism can include arms 112 that extend from upper sensor body 100 (see FIGS. 4A-4B) that are configured to engage fiber guides 300, 300'. Arms 112 can include a top end connected to and extending from sides of the upper sensor body 100 and a bottom end opposite to the top end. As shown in at least FIGS. 4A-4B, the swivel mechanism can comprise first and second arms 112 that extend from sides of the upper sensor body 100. Arms 112 can include slots 116 extending along a portion of a length of the arms 112. As shown in FIGS. 5A-5B, the lower sensor body 200 can include recessed portions 240 on sides of the lower sensor body 200 that are sized, shaped, and/or inclined to correspond with a portion of the arms 112 of the swivel mechanism and/or are sized, shaped, and/or inclined so as to facilitate movement of the arms 112 along the sides of the lower sensor body 200 when the upper and lower sensor bodies 100, 200 are rotated with respect to each other. For example, as shown in FIGS. 5A-5B and 3A-3B, the recessed portions 240 can be recessed from sides of the lower sensor body 200 and inclined inwardly toward an interior portion of the lower sensor body 200 so as to conform to a shape of the arms 112 of the swivel mechanism.

Figure 4H:
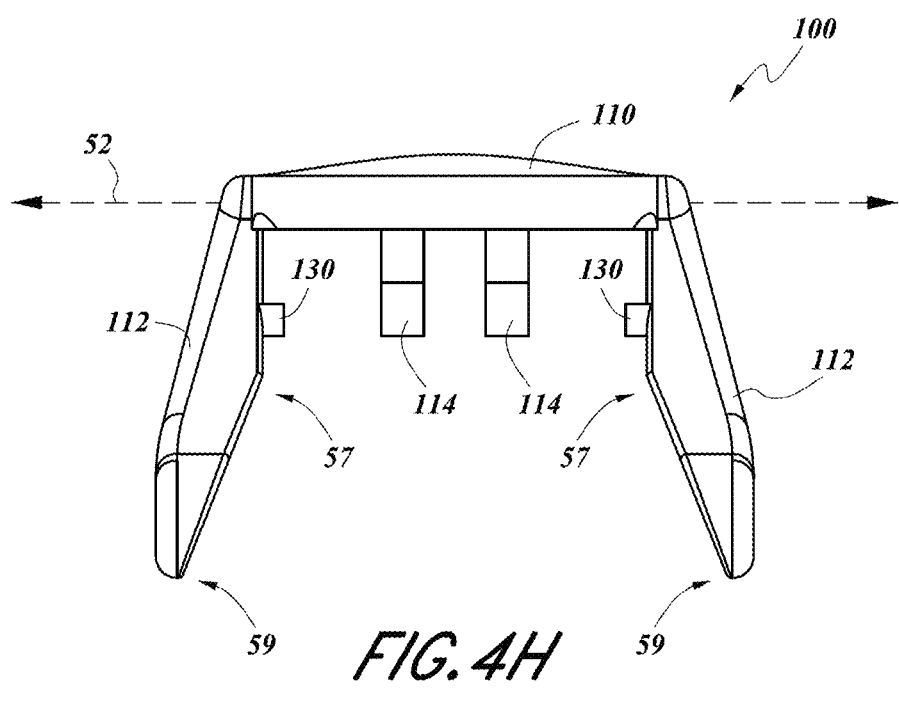
FIG. 4H illustrates a front view of the upper sensor body of FIG. 4A.
Figure 4I:
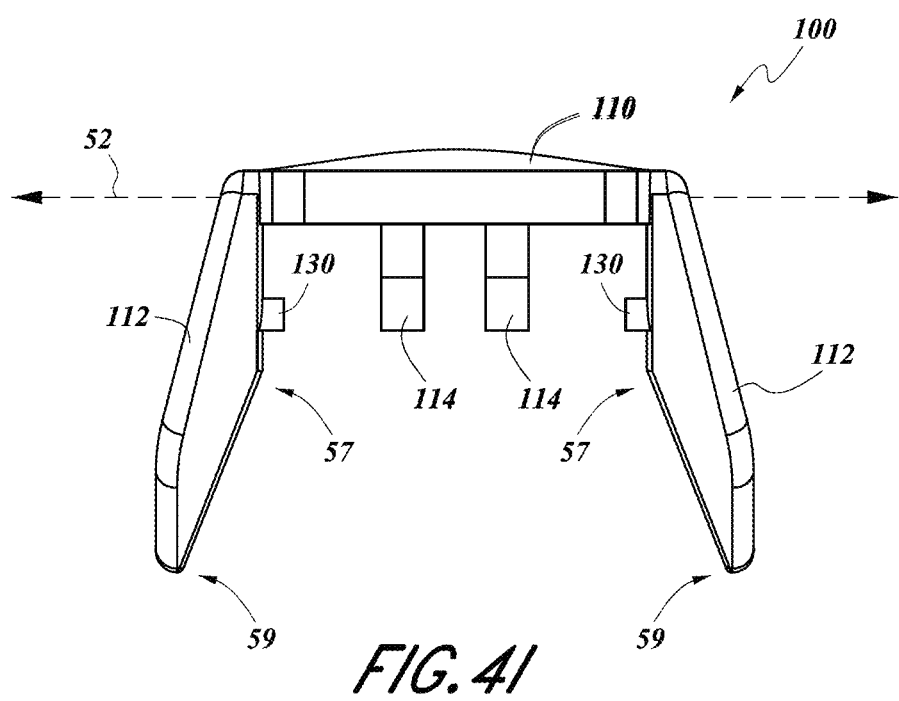
FIG. 4I illustrates a back view of the upper sensor body of FIG. 4A.

As shown by FIGS. 4H-4I, arms 112 of the swivel mechanism of noninvasive physiological sensor 10 can extend from sides of the upper sensor body 100 and flare outward in a direction parallel to transverse axis 52 (see FIGS. 4H-4I). When the upper sensor body 100 and/or the lower sensor body 200 rotate with respect to each other, arms 112 rotate and/or swivel between different positions. Additionally, interior sides of arms 112 (which face an interior of the noninvasive physiological sensor 10 when assembled) can be angled outwards from middle portions 57 of the arms 112 to end portions 59 of the arms 112. As also shown, interior surfaces of arms 112 can be inclined outward from a region between the middle portions 57 to the end portions 59.

As shown in FIGS. 3A-3B, when noninvasive physiological sensor 10 is assembled, fiber guides 300 can secure fibers 105, 107 on sides of the lower sensor body 200 and fit at least partially within recesses 250. Further, when noninvasive physiological sensor 10 is assembled, arms 112 can sit at least partially within recessed portions 240, adjacent to and on an outside of fiber guides 300, such that arms 112 contact sides of fiber guides 300. Slots 116 on arms 112 allow fibers 105, 107 to pass therethrough and couple to emitters and/or detectors as discussed with reference to the systems 1, 9, 500, and 500' above. When the noninvasive physiological sensor 10 is in a closed position (as shown by FIGS. 2A-2B) regions proximate to (for example, below) the middle portions 57 (see FIGS. 4H and 4I) of the arms 112 are in contact with fiber guides 300 (see FIGS. 2C-2D). In this closed position, these contacting regions can apply a force to the fiber guides 300 and move and/or compress the fiber guides 300 inward toward and/or against surfaces of the recessed portions 250. As shown by FIG. 2K, in this closed position, the fibers 105, 107 which are secured and/or coupled with the fiber guides 300, are forced inward toward each other within the interior space defined by the lower sensor body 200. As illustrated by FIG. 2K, when forced inward toward each other in this closed position, the fibers 105, 107 can compress a portion of a tissue of a finger 11 of a user. This compressed portion of tissue is illustrated by dotted lines 13 in FIG. 2K.

Utilizing one or more probes such as fibers 105, 107 (for example, ends of fibers 105, 107) to emit light through, and detect attenuated light from, tissue of a user can advantageously allow a short path length of tissue to be interrogated. As discussed elsewhere herein, the compression of tissue in such manner can allow the fibers 105, 107 to transmit light through, and collect attenuated light from, deeper regions of tissue where blood vessels are present, which can advantageously increase the accuracy and ability of determining physiological measurements. In some cases, the one or more probes (such as fibers 105, 107) can be moved toward one another such that, when they compress the tissue of the user, a distance between the ends of the fibers 105, 107 are between $\frac{1}{12}$ inch (0.21 cm) and $\frac{1}{4}$ inch (0.64 cm). For example, the distance between the ends of the fibers 105, 107 when compressing a portion of the tissue of the user can be less than or equal to $\frac{1}{12}$ inch (0.21 cm), $\frac{1}{11}$ inch (0.23 cm), $\frac{1}{10}$ inch (0.25 cm), $\frac{1}{9}$ inch (0.28 cm), $\frac{1}{8}$ inch (0.32 cm), $\frac{1}{7}$ inch (0.36 cm), $\frac{1}{6}$ inch (0.42 cm), $\frac{1}{5}$ inch (0.51 cm), $\frac{1}{4}$ of inch (0.64 cm), or any value therebetween, or any range bounded by any combination of these values, although values outside these are possible. The one or more probes (such as fibers 105, 107) can be moved toward one another such that, when they compress the tissue of the user, the compressed tissue has a thickness $\frac{1}{12}$ inch (0.21 cm) and $\frac{1}{4}$ inch (0.64 cm), for example. The one or more probes (such as fibers 105, 107) can be moved toward one another such that, when they compress the tissue of the user, the compressed tissue has a thickness less than or equal to $\frac{1}{12}$ inch (0.21 cm), $\frac{1}{11}$ inch (0.23 cm), $\frac{1}{10}$ inch (0.25 cm), $\frac{1}{9}$ inch (0.28 cm), $\frac{1}{8}$ inch (0.32 cm), $\frac{1}{7}$ inch (0.36 cm), $\frac{1}{6}$ inch (0.42 cm), $\frac{1}{5}$ inch (0.51 cm), $\frac{1}{4}$ of inch (0.64 cm), or any value therebetween, or any range bounded by any combination of these values, although values outside these are possible. Interrogating a short path length of tissue allows measurements to be taken through highly absorbing media which enables detection of signals that may normally fall below detectable limits. Additionally, even a capillary bed of tissue can be probed over a very short transmission path length. Such utilization of fibers (such as fibers 105, 107) in such manner thus can provide and/or allow for higher quality measurement and/or analysis as opposed to utilization of typical noninvasive sensor devices that emit and detect light through an entire finger which produces lower quality (for example, due to emission and detection of light through a bone in the finger). For example, fibers 105, 107 can be used to transmit, and receive, light through a portion of tissue of a user without directing or allowing the light or optical radiation to pass through a bone, cartilage, or muscle, and/or without directing light or optical radiation toward a bone, cartilage, or muscle of a user. While the above discussion is made with reference to fibers 105, 107, as mentioned elsewhere herein, such discussion is equally applicable to fibers 30d and 20g discussed previously. Thus, for example, fiber(s) 30d and fiber 20g can be moved towards one another via interaction with noninvasive physiological sensor 10 similarly as discussed with reference to fibers 105 and 107 above.

When the upper and lower sensor bodies 100, 200 are rotated about each other (as discussed above), arms 112 can slide within, along, and/or adjacent to recessed portions 240 of lower sensor body 200. More specifically, a region between middle portions 57 and end portions 59 of arms 112 can slide within, along, and/or adjacent to recessed portions 240. In a closed position, regions proximate to (for example, below) the middle portions 57 are in contact with recessed portions 240. When the upper and lower sensor bodies 100, 200 are rotated about each other, the recessed portions 240 contact a region between the middle portions 57 and end portions 59 of arms 112. When the upper and lower sensor bodies 100, 200 are rotated to a maximum open position, end portions 59 of arms 112 can contact the recessed portions 240 and fiber guides 300. At this maximum open position, the end portions 59 can contact the recessed portions 240 at an end of the slots 116 since fibers 105,107 pass through the slots 116 and through-holes 314 in fiber guides 300. The outward inclination of the interior surfaces of arms 112 (see FIGS. 4H-4I) from middle portions 57 to end portions 59 allows less force to be applied by the arms 112 to the fiber guides 300. This in turn allows the fibers 105, 107 coupled to fiber guides 300 to move away from each other within the interior space defined by the lower sensor body 200, as illustrated by FIG. 2J. Slots 116 in arms 112 allow the arms 112 to follow the movement and/or rotation of the upper and lower sensor bodies 100, 200 with respect to one another while not interfering with the fibers 105, 107 when extending through the through-holes 314 in the fiber guides 300 and the holes 230 in the lower sensor body 200. Such configuration allows the fibers 105, 107 to maintain alignment and a straightened layout which increases the ability of the fibers 105, 107 to transmit and collect light, thus increasing the accuracy of physiological measurements obtained from the noninvasive physiological sensor 10. Slots 116 can have a length corresponding to a desired rotational capacity of the upper sensor body 100 and lower body sensor 200 with respect to one another. For example, where it is desirable to allow the upper and lower sensor bodies 100, 200 to rotate about each other to a large degree, slots 116 can have a length that is a greater percentage of a length of the arms 112. The slots 116 can have a length that is a percentage of a length of the arms 112. For example, the length of the slots 116 can be 20%, 30%, 40%, 50%, 60%, 70%, 80%, or 90% of the length of the side rails 110, or any value or range therebetween, although values outside these ranges can be used in some cases.

As shown by at least FIGS. 4A-4B and 2G-2H, arms 112 can extend from sides of upper sensor body 100 and curve towards front portion 60 of noninvasive physiological sensor 10 and front portion 113 of the upper sensor body 100. The curvature of the arms 122 in this direction can advantageously allow a portion of the interior surface of the arms 112 to maintain contact with the fiber guides 300 when the noninvasive physiological sensor 10 is rotated. For example, when the upper and lower sensor bodies 100, 200 are rotated about each other and/or about the joint (including hinges 114, 214), the interior surfaces of the arms 112 can maintain contact with the fiber guides 300 between the middle portions 57 and the end portions 59 of the arms 112. In such configuration, the arms 112 are curved toward the front portion 60 of the noninvasive physiological sensor 10 so as to correspond with the rotational movement of the upper and lower sensor bodies 100, 200 with respect to one another. Further, maintaining contact between the arms 112 and the fiber guides 300 advantageously allows the fiber guides 300 and coupled fibers 105, 107 to maintain alignment and positioning, while also allowing precise adjustment and movement of the fibers 105, 107 toward and away from each other within the interior space defined by the lower sensor body 200.

As shown by FIG. 4H, noninvasive physiological sensor 10 can include one or more stoppers 130 configured to prevent the upper sensor body 100 from rotating beyond a limit with respect to the lower sensor body 200. For example, noninvasive physiological sensor 10 can include two stoppers 130, each extending inwardly from interior surfaces of the arms 112. Stoppers 130 can be positioned along the interior surface of the arms 112 such that they are in contact with a top surface 211 of the lower sensor body 200 when the noninvasive physiological sensor 10 is in a closed position. For example, as shown in FIGS. 4H-4I and 2C-2D, when the noninvasive physiological sensor 10 is in the closed position, stoppers 130 sit against a top surface 211 of lower sensor body 200. In such configuration, stoppers 130 prevent the upper sensor body 100 from rotating beyond a maximum limit relative to the lower sensor body 200. This advantageously prevents the noninvasive physiological sensor 10 from applying to much force or pressure to a user's tissue (for example, a finger 11) when the tissue is placed therewithin, especially where the noninvasive physiological sensor 10 includes a biasing member 103 which may tend to over-rotate the upper sensor body 100 relative to the lower sensor body 200 in some cases.

FIGS. 5A-5G illustrates various views of lower sensor body 200. Lower sensor body 200 can include a top surface 211 which faces bottom surface 111 of the upper sensor body 100 when noninvasive physiological sensor 10 is assembled and a bottom surface opposite 237 to the top surface 211 of the lower sensor body 200. The top surface 211 of the lower sensor body 200 can include a recessed portion 210. As discussed above, noninvasive physiological sensor 10 or a portion thereof can be shaped to conform to a portion of a user, such as a finger 11 of a user. For example, the recessed portion 210 of the top surface 211 can be shaped to conform to a user's finger. As shown, top surface 211 can be sub-stantially flat and can extend along sides of the lower sensor body 200 and the recessed portion 210 can be curved and/or inclined from interior edges of the substantially flat portion of the top surface 211. The top surface 211 can be flat or substantially flat except for recess 222 (discussed above), recessed portion 220 (discussed above), and/or recessed portion 210. As depicted in FIGS. 5A-5B, recessed portion 210 can be curved and/or inclined along sides thereof, and the sides of the recessed portion 210 can be sized and/or shaped to conform to sides of a user's finger. As also shown, the recessed portion 210 can have a front section that is sized and/or shaped to conform to a tip or front portion of a user's finger. For example, the front of the recessed portion 210 can be curved and/or inclined to conform to a tip of a user's finger, and can resemble a portion of a bowl.

As discussed above, the lower sensor body 200 can have one or more holes 230 configured to allow fibers 105, 107 to pass therethough into an interior space defined by the lower sensor body 200. The interior space defined by the lower sensor body 200 can be the space or volume defined by the recessed portion 210. As shown in at least FIGS. 5D-5E and 5A-5B, lower sensor body 200 can have an opening 270. As discussed above, noninvasive physiological sensor 10, when in a closed position, can compress a portion of tissue of a user, for example, by movement of the fibers 105, 107 toward each other via the interaction of the swivel mechanism and the fiber guides 300. Opening 270 can advantageously permit inspection of the compressed or pinched portion of tissue of the user from underneath. Such inspection can involve, for example, checking to make sure adequate skin tissue has been isolated so that an accurate physiological measurement can take place. Such inspection can also allow a caregiver or a user to ensure that the fibers 105, 107 are aligned and/or extending properly, and/or whether or not a user's tissue is present in the device. Opening 270 can be rectangular, or alternatively, square, circular, among other shapes.

Figure 5C:
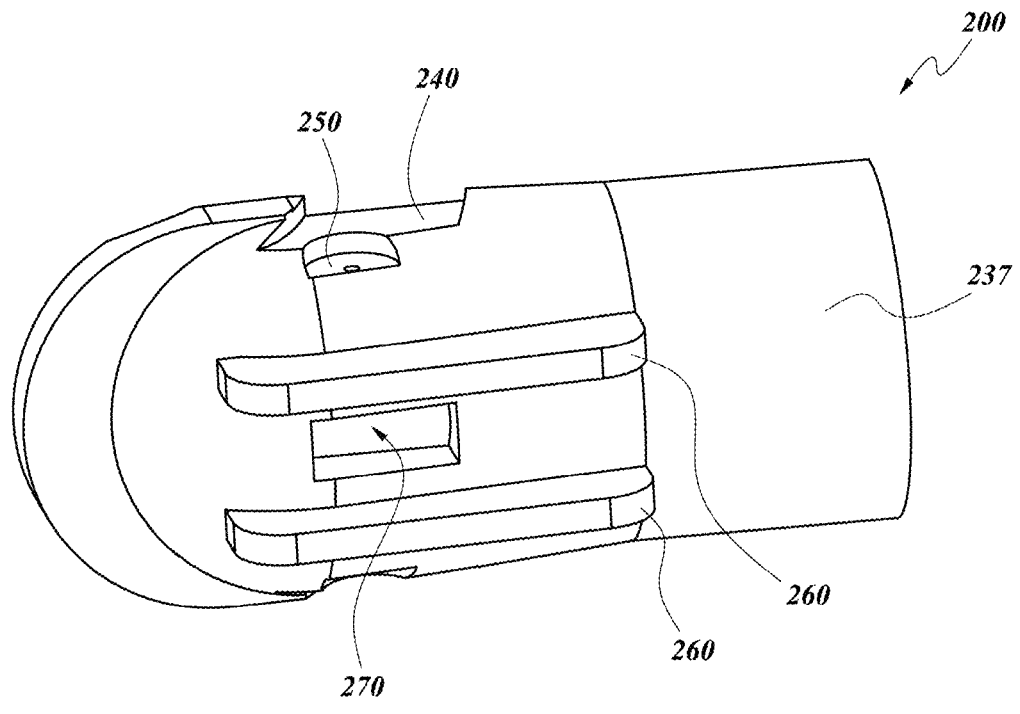
FIG. 5C illustrates a bottom perspective view of the lower sensor body of FIG. 5A.
Figures 5D, 5E:
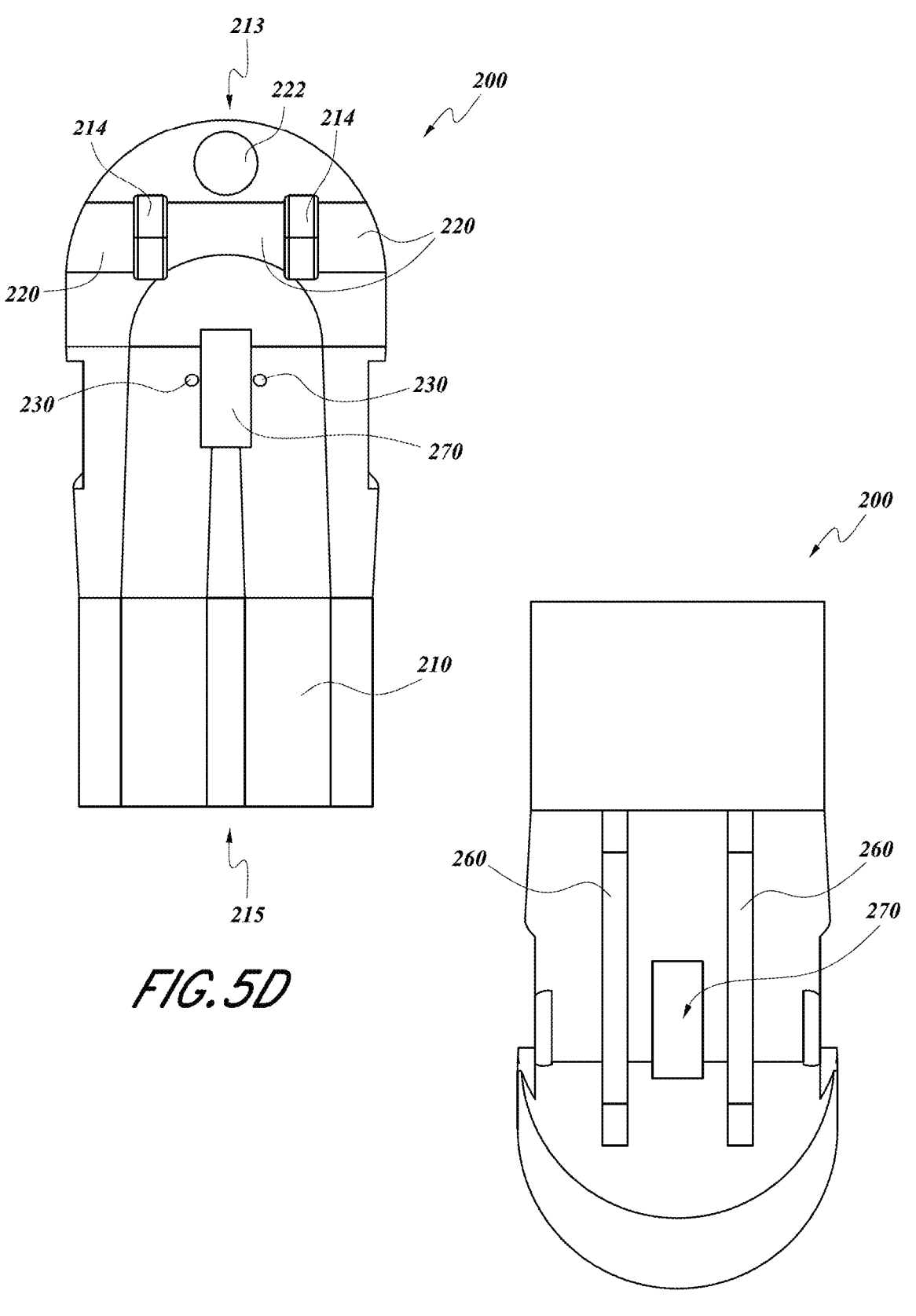
FIG. 5D illustrates a top view of the lower sensor body of FIG. 5A.
FIG. 5E illustrates a bottom view of the lower sensor body of FIG. 5A.

As shown by FIG. 5C, lower sensor body 200 can include legs 260 that extend outward from and along a portion of bottom surface 237 of lower sensor body 200. Legs 260 can allow the lower sensor body 200 and/or the noninvasive physiological sensor 10 to rest atop a surface (such as a flat surface). Where a portion of the bottom surface 237 of lower sensor body 200 is curved (see, for example, FIG. 5C), legs 260 can provide support that allows the sensor 10 to sit on a surface without rocking along longitudinal axis 50 of the sensor 10.

As discussed above, the noninvasive physiological sensor 10 can have a joint including a first coupling portion and a second coupling portion. As also discussed above, the first coupling portion can be one or more hinges 114 positioned on the upper sensor body 100 and the second coupling portion can be one or more hinges 214 positioned on the lower sensor body 200. Hinges 214 can be positioned adjacent to and on the outside of the hinges 114 and can be shaped to correspond with recessed portion 120 on the bottom surface 111 of upper sensor body 100, as discussed above. Recess 222 can be sized to fit an end of biasing member 103 therewithin, as also discussed above. Recessed portion 220 can be shaped to correspond with the shape of hinges 114 so as to facilitate rotation of the hinges 113 with little or no interference with the lower sensor body 200, as discussed above.

Figure 5F:
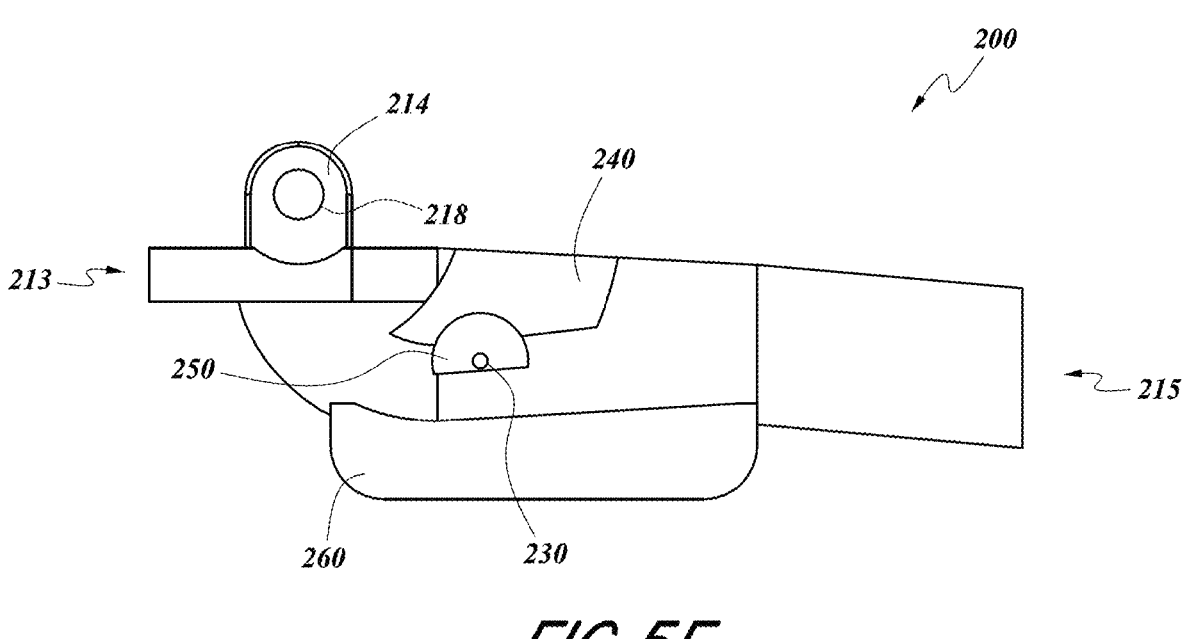
FIG. 5F illustrates a side view of the lower sensor body of FIG. 5A.
Figure 5G:
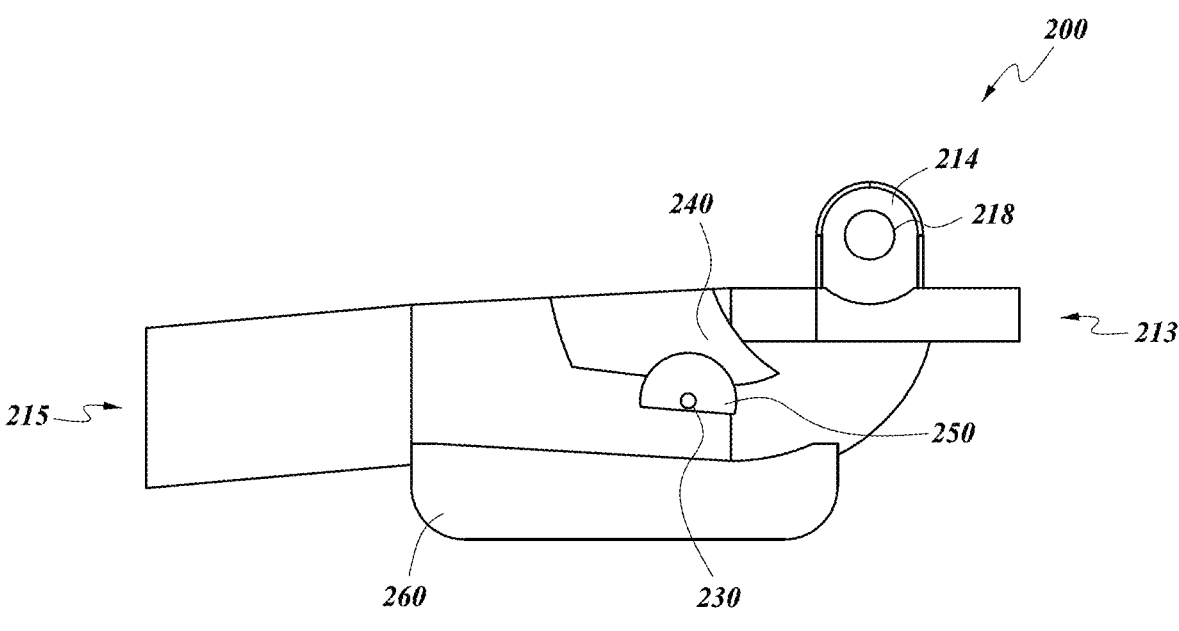
FIG. 5G illustrates another side view of the lower sensor body of FIG. 5A.

FIGS. 5F-5G illustrate side views of the lower sensor body 200. These figures show an exemplary shape of recessed portions 240, 250. As discussed herein, recessed portions 240 can be shaped to accommodate a portion of the arms 112 of the swivel mechanism of the noninvasive physiological sensor 10. The recessed portions 240 can be sized, shaped, and/or oriented to facilitate movement of the arms 112 of the swivel mechanism. For example, the recessed portions 240 can have a width (in a direction parallel to longitudinal axis 50) that is larger than or equal to a width of the arms 112 of the swivel mechanism so as to allow the arms 112 to at least partially fit therewithin. Further, the recessed portions 240 can be oriented so as to conform to the curvature of the arms 112. For example, the recessed portions 240 can be curved toward a front 213 of the lower sensor body 200 similar to the direction of curvature of the arms 112 of the swivel mechanism. Thus, recessed portions 240 can be sized, shaped, and/or oriented so as to facilitate movement of the arms 112 or the swivel mechanism there within and adjacent to sides of the lower sensor body 200, which can, among other things allow the arms 112 to contact the fiber guides 300 as discussed above.

FIGS. 5F-5G also illustrate recesses 250. As discussed above, the recesses 250 can be sized and/or shaped to allow a portion of the fiber guides 300 to fit at least partially there within. For example, the recesses 250 can be sized and/or shaped to allow an end of the fiber guides 300 to fit at least partially within adjacent to sides of the lower sensor body 200.

While FIGS. 5A-5G illustrate the lower sensor body 200 having one hole 230 on each of the sides of the lower sensor body 200, the lower sensor body 200 can have a different number of holes 230 on one or both of the sides of the lower sensor body 200. For example, with reference to FIG. 1J and 5A, lower sensor body 200 can have a plurality of holes 230 (such as three holes 230) on a first side of lower sensor body 200, where each of the plurality of holes 230 are sized and/or shaped to receive fibers 30d. Additionally or alternatively, with reference to the hole 230 appearing on the right side of lower sensor body 200 as shown in FIG. 5B, lower sensor body 200 can have a plurality of holes 230 on such right side of lower sensor body 200 that are sized and/or shaped to receive one or more probes which are coupled to emitters. Thus, lower sensor body 200 can include one or more holes 230 on one of both sides of lower sensor body 200 which allow one or more fibers to move through and/or within the lower sensor body 200 to contact (for example, probe) tissue of a user.

Figure 6A:
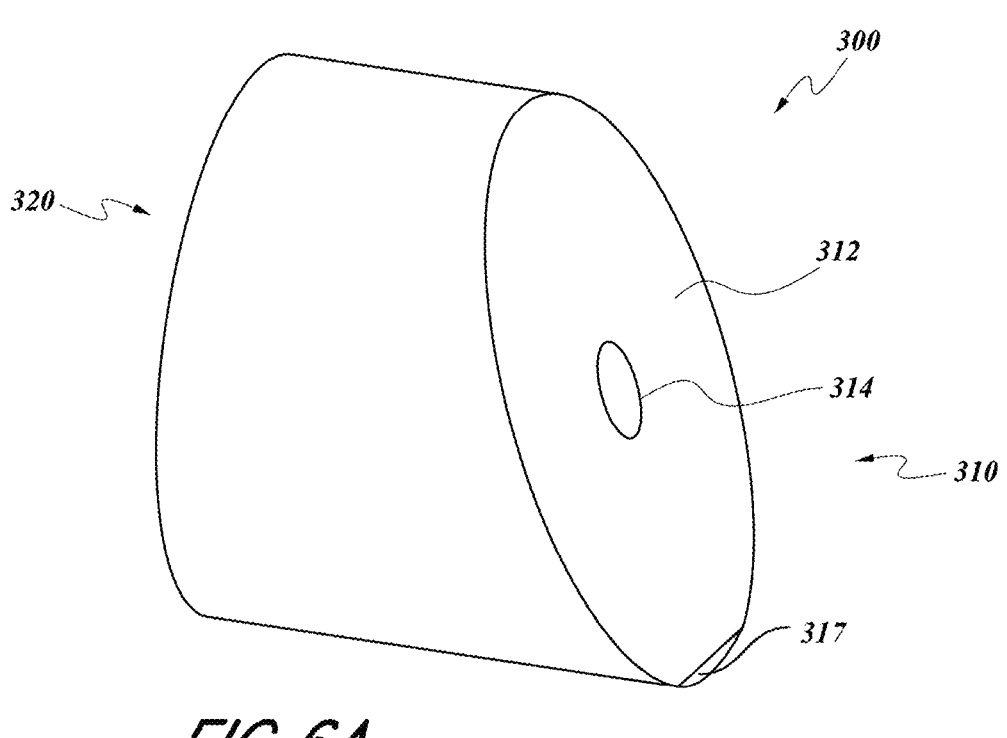
FIG. 6A-6F illustrate various views of an embodiment of a fiber guide in accordance with aspects of this disclosure.
Figure 6B:
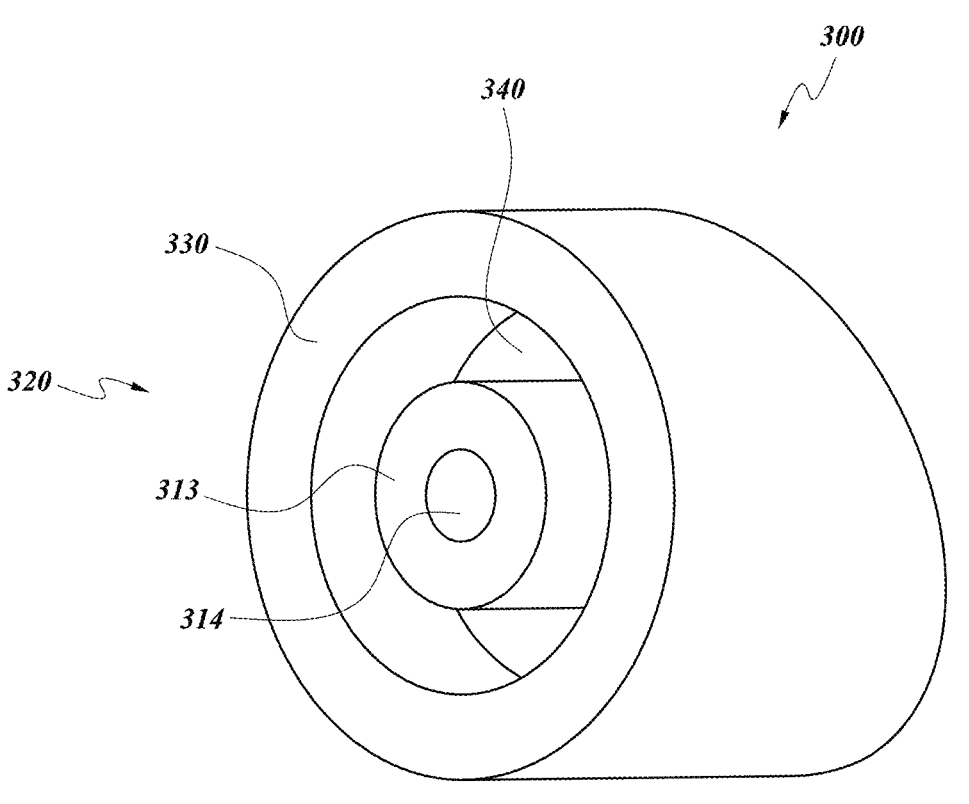
Figure 6C:
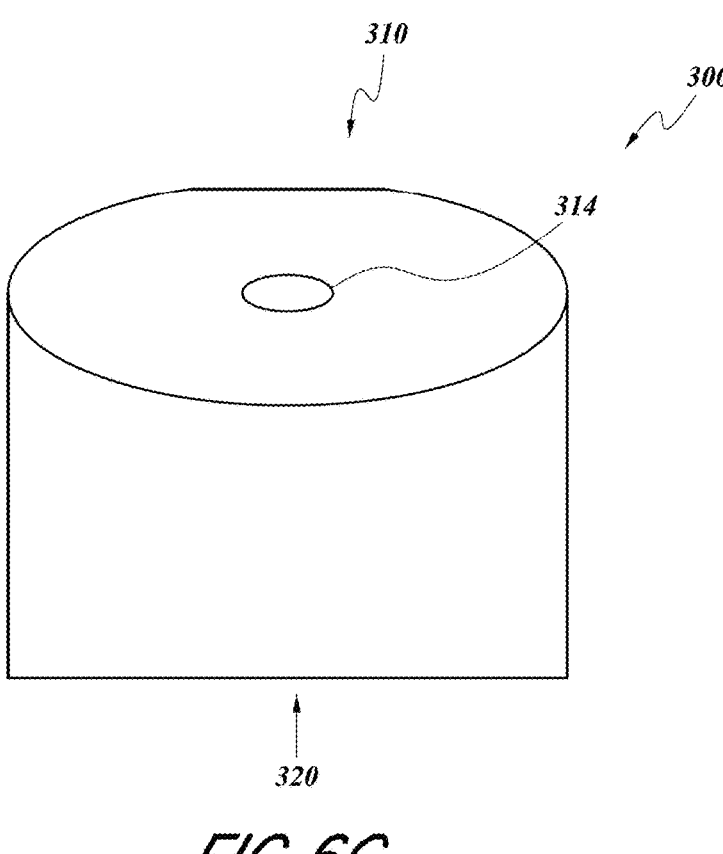
Figure 6D:
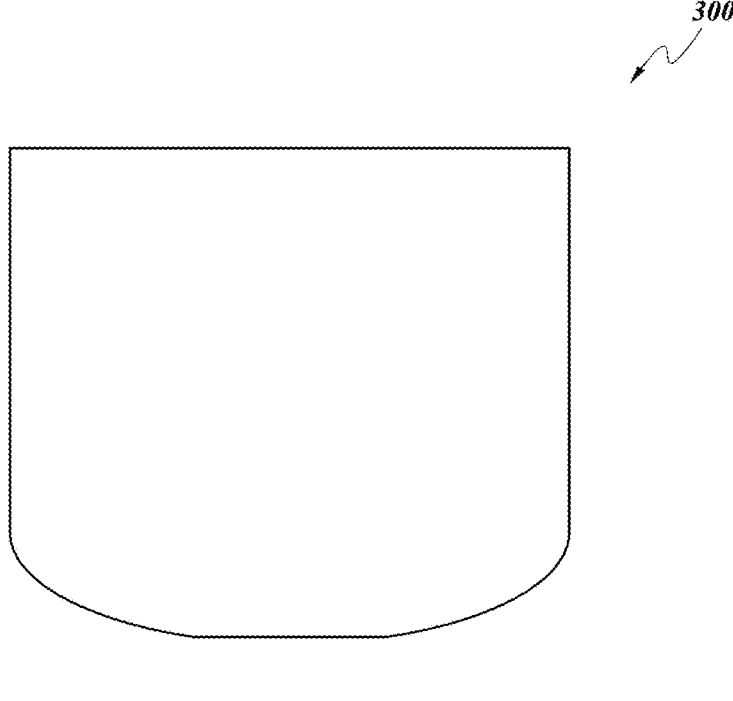
Figures 6E, 6F:
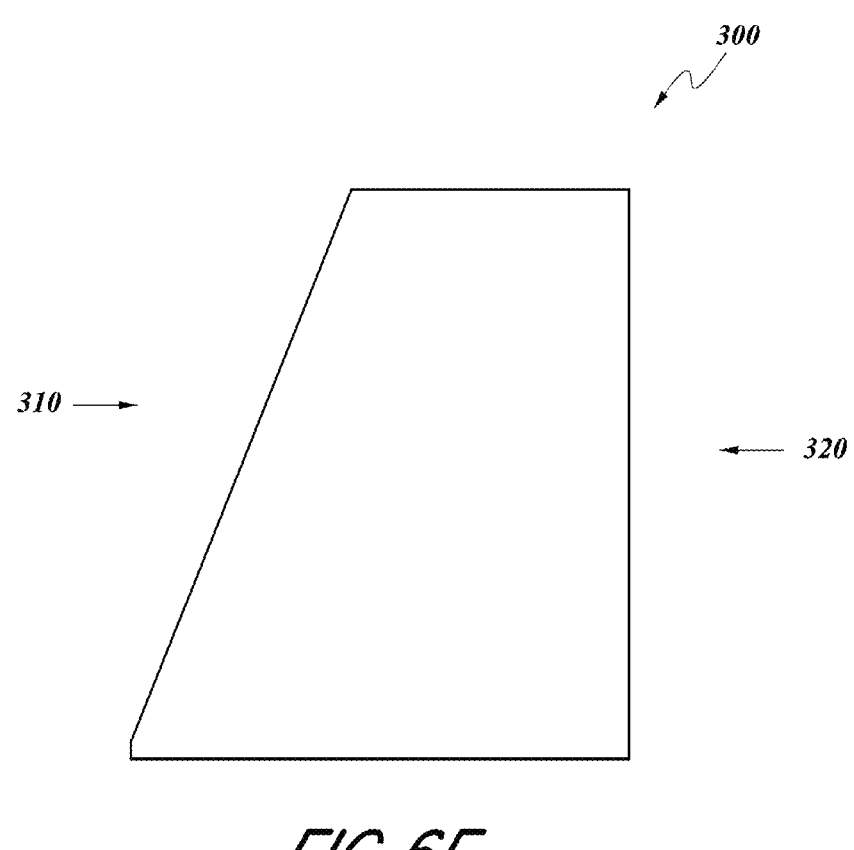

FIGS. 6A-6F illustrate various views of an embodiment of a fiber guide 300 (also referred to herein as "probe guide" and "spacer"). Fiber guide 300 has an interior end 320 configured to contact the recess 250 of the lower sensor body 200 when the noninvasive physiological sensor 10 is assembled and an exterior end 310 configured to contact an interior surface of the arms 112 of the swivel mechanism when the sensor 10 is assembled. As shown, fiber guide 300 can have a through-hole 314 sized and/or shaped to permit fiber 105, 107 (or any of the other fibers discussed herein) to pass therethrough. Through-hole 314 can begin at exterior end 310 and end at interior end 320. Interior end 320 can have an outer portion 330 separated from an inner portion 313 by an intermediate portion 340. The inner portion 313 can surround the through-hole 314. The intermediate portion 340 can be recessed from a plane at the interior end 320. The intermediate portion 340 can be in between the outer portion 330 and the inner portion 313, and can be open, as shown in FIG. 6B. Any of outer portion 330, inner portion 313, and/or intermediate portion 340 can be annular in shape, for example.

As shown by FIG. 6A and as discussed in more detail below, end 310 of the fiber guide 300 can include an inclined portion 312. In some embodiments, the entire end 310 comprises an inclined portion 312. In some embodiments, only a portion of the end 310 comprises an inclined portion 312. In some embodiments, end 310 also includes a non-inclined portion 317. The fiber guide 300 can have a circular or partially circular cross-section. For example, a cross-section of fiber guide 300 near the interior end 320 can be circular, whereas a cross-section near the exterior end 310 can be partially circular due to the inclination of the exterior end 310. The inclination of exterior end 310 of the fiber guide 300 can correspond to the inclination and/or orientation of the arms 112. As discussed above and as shown in FIGS. 4H-4I, interior surfaces of arms 112 can be inclined outward from a region between the middle portions 57 to end portions 59. Such inclination allows more and/or less force to be applied by the arms 112 to the fiber guides 300 when the swivel mechanism is engaged via rotation of the upper sensor body 100 about the lower sensor body 200 (or vice versa). The inclination of exterior end 310 of fiber guide 300 allows the inclined interior surface of the arms 112 to gradually slide along and/or contact the exterior end 310 so that the contact and/or force applied to the fiber guide 300 is more precise. Such precision in contact and/or force, in turn, allows the fibers 105, 107 positioning and/or movement to be more controlled, so that tissue of a user (for example, tissue of a user's finger) can be compressed in a controlled manner. Controlling the compression of the user's tissue within the noninvasive physiological sensor 10 can ensure that the fibers 105, 107 are within a desired alignment so that more accurate physiological measurements can be taken and also reduces discomfort to the user resulting from such compression. As shown in FIG. 6A, end 310 can have a non-inclined portion 317 in some embodiments. The non-inclined portion 317 can help facilitate less contact with the interior surface of arms 112 in combination with the inclined portion 312 so as to vary the contact and/or force applied to the fiber guide 300 via the arms 112.

While fiber guide 300 is illustrated as having one hole 314, fiber guide 300 can include more than one hole 314, such as two, three, four, five, six, or seven holes extending through fiber guide 300. Each of the holes 314 can be sized and shaped to receive a fiber, such as any of the fibers discussed previously. For example, fiber guide 300 can include three holes 314 which can be sized and/or shaped to receive one of the three fibers 30d that are shown and discussed with reference to FIGS. 1G-1J. Such plurality of holes 314 can be positioned through the fiber guide 300 in various locations, for example, along a single vertical plane to match the layout of the fibers 30d as shown in FIG. 1J, or in other locations and/or positions.

Figure 7A:
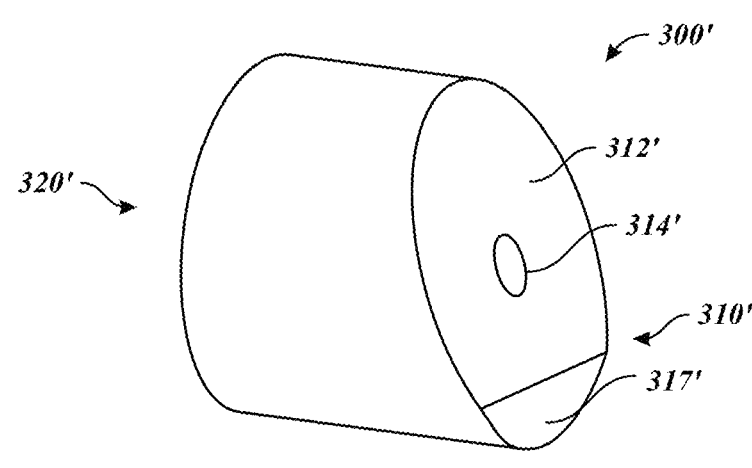
FIGS. 7A-7F illustrate various views of another embodiment of a fiber guide in accordance with aspects of this disclosure.
Figure 7B:
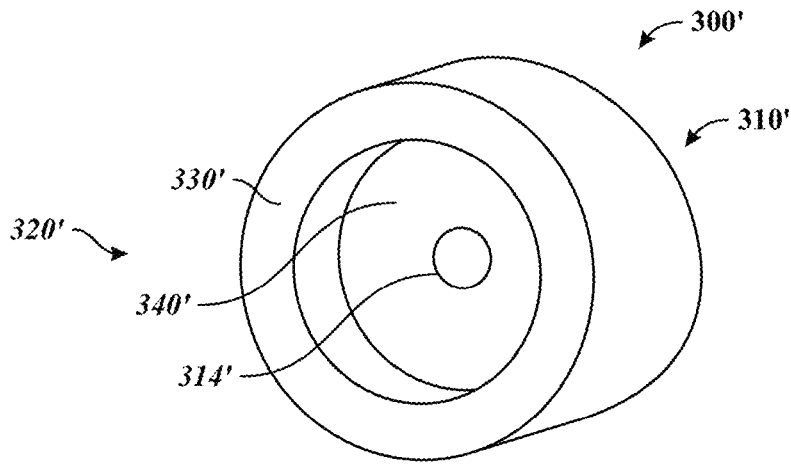
Figure 7C:
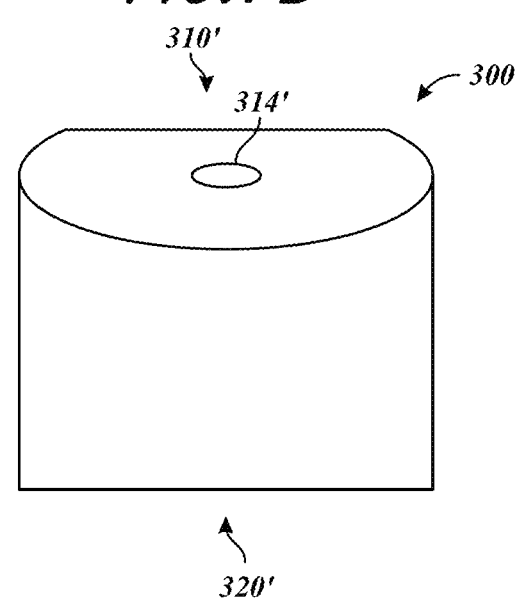
Figure 7D:
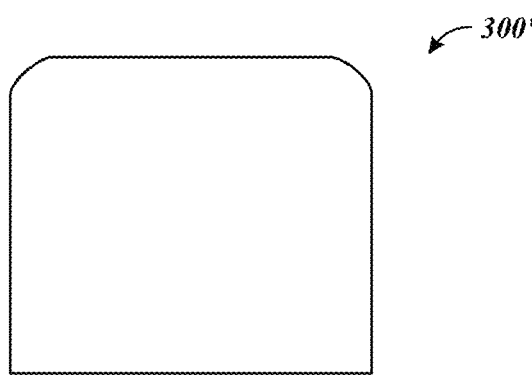
Figure 7E:
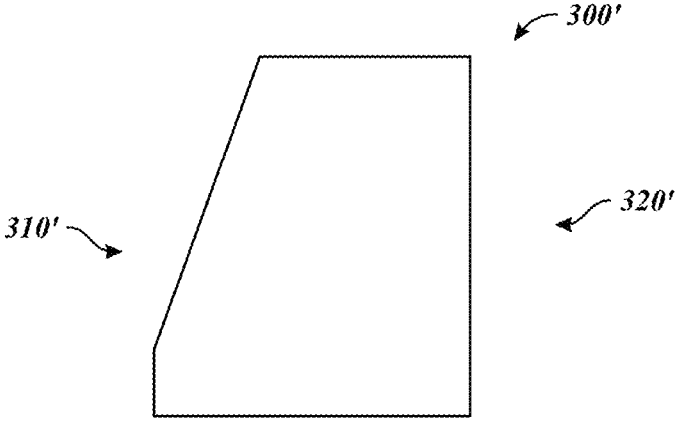
Figure 7F:
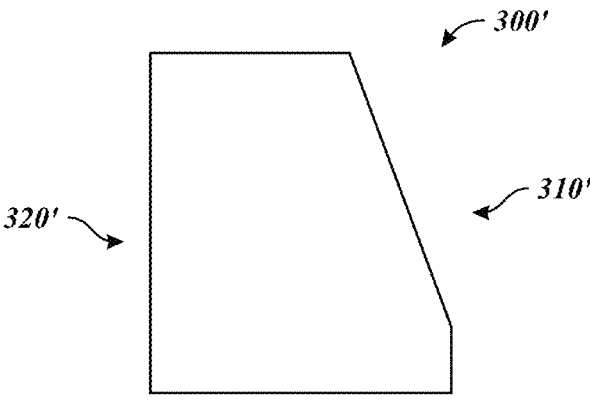

FIGS. 7A-7F illustrate various views of another embodiment of a fiber guide 300' (also referred to herein as "probe guide" and "spacer"). While much of the previous discussion with respect to the noninvasive physiological sensor 10 and FIGS. 2A-5G was made with reference to fiber guide 300, fiber guide 300' can be incorporated into noninvasive physiological sensor 10 alongside or in place of fiber guide 300 and any of the other components of noninvasive physiological sensor 10 described previously. Fiber guide 300' has an interior end 320' configured to contact the recess 250 of the lower sensor body 200 when the noninvasive physiological sensor 10 is assembled and an exterior end 310' configured to contact an interior surface of the arms 112 of the swivel mechanism when the sensor 10 is assembled. As shown, fiber guide 300' can have a through-hole 314' sized and/or shaped to permit fiber 105, 107 (or any of the other fibers discussed herein) to pass therethrough. Through-hole 314' can begin at exterior end 310' and can extend through a portion of fiber guide 300'. Interior end 320' can have an outer portion 330' and an open cavity 340' defined within the outer portion 330'. The cavity 340' can have a surface that is parallel to a plane of the end 320', and through-hole 314' can extend from end 310' through an interior of the fiber guide 300' to the surface of cavity 340'. As shown by FIG. 7A and as discussed in more detail below, end 310' of the fiber guide 300' can include an inclined portion 312'. In some embodiments, only a portion of the end 310' comprises an inclined portion 312', as illustrated in at least FIGS. 7A and 7E-7F. In some embodiments, end 310' also includes a non-inclined portion 317'. FIGS. 7E-7F show side views of fiber guide 300' and show the inclined portion 312' and the non-inclined portion 317' of the end 310'. The fiber guide 300' can have a circular or partially circular cross-section. For example, a cross-section of fiber guide 300' near the interior end 320' can be circular, whereas a cross-section near the exterior end 310' can be partially circular due to the inclination of the exterior end 310'. The inclination of exterior end 310' of the fiber guide 300' can correspond to the inclination and/or orientation of the arms 112. As discussed above and as shown in FIGS. 4H-4I, interior surfaces of arms 112 can be inclined outward from a region between the middle portions 57 to end portions 59. Such inclination allows more and/or less force to be applied by the arms 112 to the fiber guides 300' when the swivel mechanism is engaged via rotation of the upper sensor body 100 about the lower sensor body 200 (or vice versa). The inclination of exterior end 310' of fiber guide 300' allows the inclined interior surface of the arms 112 to gradually slide along and/or contact the exterior end 310' so that the contact and/or force applied to the fiber guide 300' is more precise. Such precision in contact and/or force, in turn, allows the fibers 105, 107 (or any of the other fibers discussed herein) positioning and/or movement to be more controlled, so that tissue of a user (for example, tissue of a user's finger) can be compressed in a controlled manner. Controlling the compression of the user's tissue within the noninvasive physiological sensor 10 can ensure that the fibers 105, 107 (or any of the other fibers discussed herein) are within a desired alignment so that more accurate physiological measurements can be taken and also reduces discomfort to the user resulting from such compression. As discussed above, end 310' can have a non-inclined portion 317' in some embodiments. The non-inclined portion 317' can help facilitate less contact with the interior surface of arms 112 in combination with the inclined portion 312' so as to vary the contact and/or force applied to the fiber guide 300' via the arms 112.

While fiber guide 300' is illustrated as having one hole 314', fiber guide 300' can include more than one hole 314', such as two, three, four, five, six, or seven holes extending through fiber guide 300'. Each of the holes 314' can be sized and shaped to receive a fiber, such as any of the fibers discussed previously. For example, fiber guide 300' can include three holes 314' which can be sized and/or shaped to receive one of the three fibers 30d that are shown and discussed with reference to FIGS. 1G-1J. Such plurality of holes 314' can be positioned through the fiber guide 300' in various locations, for example, along a single vertical plane to match the layout of the fibers 30*d* as shown in FIG. 1J, or in other locations and/or positions.

Although the present disclosure may describe the upper sensor body 100 as being oriented vertically above the lower sensor body 200 when the noninvasive physiological sensor 10 is assembled and/or in use, the use of the term "upper" and "lower" should not be construed to mean that such orientation is required or necessary. For example, the lower sensor body 200 can be oriented vertically above the upper sensor body 100 when the noninvasive physiological sensor 10 is assembled and/or in use. In such configuration, FIGS. 2J and 2K thus can illustrate a top view of the noninvasive physiological sensor 10 when in use and/or when a portion of a user's body (such as a finger or a toe) is placed within. Further, in such configuration as shown in FIGS. 2J and 2K, the opening 270 in the lower sensor body 200 can allow a user to inspect tissue pinched and/or compressed by ends of fibers 105, 107 (as illustrated by the compressed portion 13 of the tissue in FIG. 2K). Furthermore, even though it is mentioned that a pin may be used to join the upper sensor body 100 with the lower sensor body 200, a plurality of pins can be used to join the upper sensor body 100 with the lower sensor body 200 and/or other methods of joining the upper sensor body 100 and the lower sensor body 200 may be used.

Although this disclosure has been disclosed in the context of certain preferred embodiments and examples, it will be understood by those skilled in the art that the present disclosure extends beyond the specifically disclosed embodiments to other alternative embodiments and/or uses of the disclosure and obvious modifications and equivalents thereof. In addition, while a number of variations of the disclosure have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. Accordingly, it should be understood that various features and aspects of the disclosed embodiments can be combined with or substituted for one another in order to form varying modes of the disclosed.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. Additionally, as used herein, "gradually" has its ordinary meaning (e.g., differs from a non-continuous, such as a step-like, change).

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A noninvasive physiological sensor comprising:
a first optical probe configured to direct optical radiation emitted from one or more emitters toward a tissue sample,
a second optical probe coupled to one or more detectors, the second optical probe configured to detect light corresponding to the emitted optical radiation after being attenuated through pulsatile blood flowing through the tissue sample;
a first sensor body and a second sensor body configured to rotate with respect to each other about a joint, the first sensor body comprising:
a first elongated slot configured to movably couple the first optical probe to the first sensor body; and
the second sensor body comprising:
a second elongated slot configured to movably couple the second optical probe to the second sensor body;
wherein, when the first sensor body or second sensor body are rotated about the joint to a first position, the first sensor body and second sensor body compress the tissue sample between the first optical probe and second optical probe, wherein in the first position the first optical probe and second optical probe are optically aligned through the tissue sample to facilitate optical communication.

2. The noninvasive physiological sensor of claim 1, wherein a first axis of the first elongated slot and a second axis of the second elongated slot are substantially aligned such that, when an end of the first optical probe passes through the first elongated slot into an interior space defined by the first sensor body and second sensor body and an end of the second optical probe passes through the second elongated slot into the interior space, the ends of the first optical probe and second optical probe oppose one another and compress the tissue sample.

3. The noninvasive physiological sensor of claim 1, wherein the first sensor body and second sensor body comprise one or more stoppers, and wherein the stoppers are configured to set a minimum distance between an end of the first optical probe and an end of the second optical probe.

4. The noninvasive physiological sensor of claim 1, wherein, when the first sensor body and second sensor are rotated about the joint to a second position, an end of the first optical probe and an end of the second optical probe are configured to move further away from one another.

5. The noninvasive physiological sensor of claim 1, wherein the joint further comprises one or more hinges configured to facilitate a rotation of the first sensor body and second sensor body about the joint.

6. The noninvasive physiological sensor of claim 5, wherein the first sensor body comprises one or more recessed areas, and wherein each of the one or more hinges is coupled to one of the one or more recessed areas.

7. The noninvasive physiological sensor of claim 5, wherein the second sensor body comprises one or more recessed areas, and wherein each of the one or more hinges is coupled to one of the one or more recessed areas.

8. The noninvasive physiological sensor of claim 1, wherein the joint comprises a first hinge extending from the first sensor body, a second hinge extending from the second sensor body, and a pin configured to extend through holes in the first and second hinges and couple the first and second hinges to one another.

9. The noninvasive physiological sensor of claim 1, wherein at least one of an end of the first optical probe or an end of the second optical probe is angled.

10. The noninvasive physiological sensor of claim 9, wherein the end of the first optical probe is angled with respect to a first axis and the end of the second optical probe is angled with respect to a second axis.

11. A method of measuring a physiological parameter of a user, the method comprising:
obtaining a sensor, wherein the sensor comprises:
a first optical probe configured to direct optical radiation emitted from one or more emitters toward a tissue sample,
a second optical probe coupled to one or more detectors, the second optical probe configured to detect light corresponding to the emitted optical radiation attenuated through pulsatile blood flowing through the tissue sample;
a first sensor body and a second sensor body configured to rotate with respect to each other about a joint, the first sensor body comprising:
a first elongated slot configured to movably couple the first optical probe to the first sensor body; and
the second sensor body comprising:
a second elongated slot configured to movably couple the second optical probe to the second sensor body;
rotating the first sensor body and the second sensor body about the joint to a first position, wherein in the first position, the first sensor body and second sensor body compress the tissue sample between the first optical probe and second optical probe, and wherein in the first position the first optical probe and second optical probe are optically aligned through the tissue sample to facilitate optical communication;
emitting optical radiation from the first optical probe into the compressed tissue of the user with the first optical probe;
detecting light corresponding to the emitted optical radiation after attenuation by pulsatile blood flowing in the compressed tissue with the second optical probe;
determining the physiological parameter based on the optical radiation detected by the detector.

12. The method of claim 11, wherein the joint comprises a first hinge extending from the first sensor body, a second hinge extending from the second sensor body, and a pin configured to extend through holes in the first and second hinges and couple the first and second hinges to one another.

13. The method of claim 11, further comprising:
rotating the first sensor body and the second sensor body about the joint to a second position, wherein in the second position, the first sensor body and second sensor body release the tissue sample between the first optical probe and second optical probe.

14. The method of claim 11, wherein the first sensor body and second sensor body comprise one or more stoppers, and wherein the stoppers are configured to set a minimum distance between an end of the first optical probe and an end of the second optical probe.

15. The method of claim 11, wherein an end of the first optical probe is angled with respect to a first axis and an end of the second optical probe is angled with respect to a second axis.

* * * * *